United States Patent
Mallone et al.

(10) Patent No.: US 12,098,179 B2
(45) Date of Patent: Sep. 24, 2024

(54) ANTIGENIC PEPTIDES DERIVING FROM UROCORTIN 3 AND USES THEREOF FOR THE DIAGNOSIS AND TREATMENT OF TYPE 1 DIABETES

(71) Applicants: INSERM (INSTITUT NATIONAL DE LA SANTÉ ET DE LA RECHERCHE MÉDICALE), Paris (FR); UNIVERSITE DE PARIS, Paris (FR); CENTRE NATIONAL DE LA RECHERCHE SCIENTIFIQUE (CNRS), Paris (FR); ECOLE SUPERIEURE DE PHYSIQUE ET DE CHIMIE INDUSTRIELLES DE LA VILLE DE PARIS, Paris (FR)

(72) Inventors: Roberto Mallone, Paris (FR); Sergio Gonzalez-Duque, Paris (FR); Yann Verdier, Paris (FR); Marie-Eliane Azoury, Paris (FR); Georgia Afonso, Paris (FR); Joëlle Vinh, Paris (FR)

(73) Assignees: INSERM (INSTITUT NATIONAL DE LA SANTE ET DE LA RECHERCHE MEDICALE), Paris (FR); UNIVERSITE DE PARIS, Paris (FR); CENTRE NATIONAL DE LA RECHERCHE SCIENTIFIQUE (CNRS), Paris (FR); ECOLE SUPERIEURE DE PHYSIQUE ET DE CHIMIE INDUSTRIELLES DE LA VILLE DE PARIS, Paris (FR)

( * ) Notice: Subject to any disclaimer, the term of this patent is extended or adjusted under 35 U.S.C. 154(b) by 998 days.

(21) Appl. No.: 16/981,474

(22) PCT Filed: Mar. 15, 2019

(86) PCT No.: PCT/EP2019/056543
§ 371 (c)(1),
(2) Date: Sep. 16, 2020

(87) PCT Pub. No.: WO2019/175384
PCT Pub. Date: Sep. 19, 2019

(65) Prior Publication Data
US 2021/0024603 A1    Jan. 28, 2021

(30) Foreign Application Priority Data

Mar. 16, 2018    (EP) .................................... 18305288

(51) Int. Cl.
| | | |
|---|---|---|
| *C07K 14/575* | (2006.01) |
| *C07K 14/74* | (2006.01) |
| *C07K 16/26* | (2006.01) |
| *C12N 15/115* | (2010.01) |

(52) U.S. Cl.
CPC .. *C07K 14/57509* (2013.01); *C07K 14/70539* (2013.01); *C07K 16/26* (2013.01); *C12N 15/115* (2013.01); *C12N 2310/16* (2013.01)

(58) Field of Classification Search
CPC ........ C07K 14/57509; C07K 14/70539; C07K 16/26; C07K 2319/00
See application file for complete search history.

(56) References Cited

FOREIGN PATENT DOCUMENTS

| WO | 2016/146751 A1 | 9/2016 | |
|---|---|---|---|
| WO | WO2017150681 | * 9/2017 | ............... C07K 7/00 |

* cited by examiner

*Primary Examiner* — Elly-Gerald Stoica
(74) *Attorney, Agent, or Firm* — WC&F IP

(57) ABSTRACT

Despite the notion that human CD8$^+$ T cells are the final mediators of autoimmune β-cell destruction in type 1 diabetes (T1D), none of their target epitopes has been demonstrated to be naturally processed and presented by β cells. The inventors therefore performed an epitope discovery study combining HLA Class I peptidomics and transcriptomics strategies. Inflammatory cytokines increased β-cell peptide presentation in vitro, paralleling upregulation of HLA Class I expression. Peptide sources included known β-cell antigens and several insulin granule proteins. Urocortin 3 was identified as a novel β-cell antigen, which was processed into HLA-A2- and HLA-A3-restricted epitopes recognized by circulating naive CD8$^+$ T cells in type 1 diabetic and healthy donors. Accordingly, the present invention relates to antigenic peptides derived from urocortin-3 and uses thereof for the diagnosis and treatment of T1D.

7 Claims, No Drawings

Specification includes a Sequence Listing.

ANTIGENIC PEPTIDES DERIVING FROM UROCORTIN 3 AND USES THEREOF FOR THE DIAGNOSIS AND TREATMENT OF TYPE 1 DIABETES

FIELD OF THE INVENTION

The present invention relates to antigenic peptides and uses thereof for the diagnosis and treatment of type 1 diabetes.

BACKGROUND OF THE INVENTION

The autoimmune β-cell destruction that leads to type 1 diabetes (T1D) is driven by CD8⁺ T cells, which dominate the immune infiltrates in the human pancreas (Coppieters et al., 2012). CD8⁺ T cells recognize surface peptide-Human Leukocyte Antigen (pHLA) Class I complexes, leading to β-cell lysis mediated by cytotoxic granules (Culina et al., 2018). The identification of these peptides is therefore critical for developing tolerogenic vaccination strategies and immune staging tools based on the detection of islet-reactive CD8⁺ T cells.

Most islet antigens (Ags), namely insulin (INS) and its precursor preproinsulin (PPI), 65 kD glutamic acid decarboxylase (GAD65/GAD2), islet Ag (IA)-2 (PTPRN) (Mallone et al., 2007; Martinuzzi et al., 2008), and zinc transporter 8 (ZnT8/SLC30A8) (Scotto et al., 2012), have been identified based on their targeting by auto-antibodies, which are easier to measure. Other Ags such as islet-specific glucose-6-phosphatase catalytic subunit-related protein (IGRP) (Mallone et al., 2007), chromogranin A (CHGA) (Li et al., 2015) and islet amyloid polypeptide (IAPP) (Standifer et al., 2006) have been identified based on studies in the non-obese diabetic mouse and/or their islet-enriched expression. A systematic discovery effort for islet Ags is missing, and the available catalogue may be biased by the lack of information about the peptides that are naturally processed and presented by β cells.

Recent reports showed that mutated sequences in tumor proteins become preferential CD8⁺ T-cell target epitopes (Gubin et al., 2014; Khodadoust et al., 2017; Yadav et al., 2014), possibly because they are regarded as non-self and therefore not efficiently tolerized. Other processes in β cells may similarly facilitate tolerance escape. These include post-translational modifications (PTMs) (McGinty et al., 2014; Rondas et al., 2015), transpeptidation products generated by the splicing and fusion of non-contiguous peptide fragments from the same protein or from different ones (Babon et al., 2016; Delong et al., 2016) and the use of alternative transcription start sites (Kracht et al., 2017). These studies have mostly focused on β-cell-reactive CD4⁺ T cells, which are stimulated by pHLA Class II complexes presented by professional Ag-presenting cells that uptake β-cell apoptotic material or secretory vesicles (Vomund et al., 2015). However, these indirect Ag processing pathways do not reflect those that are specific to β cells. Indeed, several arguments suggest an active role of β cells in their own demise (Eizirik et al., 2009). First, we recently showed that some T1D susceptibility gene variants modulate islet inflammation (Marroqui et al., 2015; Marroqui et al., 2014; Moore et al., 2009), suggesting that the β-cell response to inflammatory cues is genetically modulated (Op de Beeck and Eizirik, 2016). This response triggers cytokine/chemokine release, endoplasmic reticulum (ER) stress and HLA Class I upregulation (Eizirik et al., 2009; Marroqui et al., 2017), which facilitate a productive autoimmune response. The alternative mRNA splicing signature induced by β-cell inflammation (Cnop et al., 2014; Eizirik et al., 2012; Ortis et al., 2010) has received less attention, but may similarly generate neo-sequences not translated in the thymus and regarded as non-self. Second, our recent studies highlighted a circulating islet-reactive CD8⁺ T-cell repertoire that is predominantly naïve and largely overlapping between T1D and healthy subjects (Culina et al., 2018). These findings reveal a general leakiness of central tolerance irrespective of T1D status, begging the question of what determines T1D progression versus the maintenance of a 'benign' state of autoimmunity. One hypothesis is that the target β cell and its response to inflammation may be critical in the progression toward T1D in the face of similar autoimmune T-cell repertoires across individuals.

In this context, it is crucial to understand the 'image' that human β cells deliver to CD8⁺ T cells through pHLA complexes.

SUMMARY OF THE INVENTION

The present invention relates to antigenic peptides and uses thereof for the diagnosis and treatment of type 1 diabetes. In particular, the present invention is defined by the claims.

DETAILED DESCRIPTION OF THE INVENTION

Despite the notion that human CD8⁺ T cells are the final mediators of autoimmune β-cell destruction in type 1 diabetes (T1D), none of their target epitopes has been demonstrated to be naturally processed and presented by β cells. The inventors therefore performed an epitope discovery study combining HLA Class I peptidomics and transcriptomics strategies. Inflammatory cytokines increased human β-cell peptide presentation in vitro, paralleling upregulation of HLA Class I expression. Peptide sources included known β-cell antigens and several insulin granule proteins. Preproinsulin yielded multiple HLA-A2-restricted epitopes previously described. Urocortin 3 was identified as a novel β-cell antigen, which was processed into HLA-A2-restricted epitopes recognized by circulating naïve CD8⁺ T cells in type 1 diabetic and healthy donors. This first description of the β-cell HLA peptidome may lead to new hypotheses about the antigen processing pathways employed by β cells and provide a valuable tool for developing T-cell biomarkers and tolerogenic vaccination strategies.

Accordingly, the first object of the present invention relates to an isolated peptide derived from urocortin 3 comprising:
  at least 8 consecutive amino acids in the sequence ranging from the amino acid residue at position 1 to the amino acid residue at position 21 in SEQ ID NO:1 (UCN3), or
  at least 8 consecutive amino acids in the sequence ranging from the amino acid residue at position 22 to the amino acid residue at position 71 in SEQ ID NO:1 (UCN3), or
  at least 8 consecutive amino acids in the sequence ranging from the amino acid residue at position 119 to the amino acid residue at position 162 in SEQ ID NO:1 (UCN3)

A used herein the term "urocortin 3" or "UCN3" refers to a hormone that is an endogenous ligand for corticotropin-releasing factor receptor 2 and may regulate insulin secretion in response to plasma glucose levels. UCN3 is encoded by the UCN3 gene (Gene ID: 114131). The term is also known as SCP; SPC; or UCNIII. The native variant of UCN3 is represented by SEQ ID NO:1.

```
(UNIPROT ref. Q969E3)
                                     SEQ ID NO: 1
   10         20         30         40
MLMPVHFLLL LLLLLGGPRT GLPHKFYKAK PIFSCLNTAL 50         60         70         80
SEAEKGQWED ASLLSKRSFH YLRSRDASSG EEEEGKEKKT 90        100        110        120
FPISGARGGA RGTRYRYVSQ AQPRGKPRQD TAKSPHRTKF 130        140        150        160
TLSLDVPTNI MNLLFNIAKA KNLRAQAAAN AHLMAQIGRK K
```

In some embodiments, the peptide of the present invention is an epitope. As used herein, the term "epitope" has its general meaning in the art and a fragment of at least 8 amino acids that is recognized by an immune response component. As used herein, the term "immune response component" include, but is not limited to, at least a part of a macrophage, a lymphocyte, a T-lymphocyte, a killer T-lymphocyte, an immune response modulator, a helper T-lymphocyte, an antigen receptor, an antigen presenting cell, a cytotoxic T-lymphocyte, a T-8 lymphocyte, a CD1 molecule, a B lymphocyte, an antibody, a recombinant antibody, a genetically engineered antibody, a chimeric antibody, a monospecific antibody, a bispecific antibody, a multispecific antibody, a diabody, a chimeric antibody, a humanized antibody, a human antibody, a heteroantibody, a monoclonal antibody, a polyclonal antibody, an antibody fragment, and/or synthetic antibody. The term "epitope" may be used interchangeably with antigen, paratope binding site, antigenic determinant, and/or determinant.

In some embodiments, the peptide of the present invention is a HLA-restricted epitope. As used herein, the term "human leukocyte antigen system" or "HLA" has its general meaning in the art and refers to the major histocompatibility complex (MHC) in humans. The locus contains many genes that encode cell-surface antigen-presenting proteins. The proteins encoded by certain genes are also known as antigens. The major HLA antigens are HLA class I antigens (A, B and C) and HLA class II antigens (DR, DP and DQ). HLA class I antigens present peptides (8-12 amino acids) from inside the cell, and attract CD8 cytotoxic T cells that destroy cells. HLA class II antigens present peptides from outside cells to CD4 T-helper-lymphocytes, which stimulate B-cells and other immune cells.

In some embodiments, the peptide of the present invention is a HLA class I restricted epitope. In some embodiments, the peptide of the present invention is a HLA-A*0101 restricted epitope. In some embodiments, the peptide of the present invention is a HLA-A*0201 restricted epitope. In some embodiments, the peptide of the present invention is a HLA-A*0301 restricted epitope. In some embodiments, the peptide of the present invention is a HLA-A*2402 restricted epitope. In some embodiments, the peptide of the present invention is a HLA-B*0801 restricted epitope. In some embodiments, the peptide of the present invention is a HLA-B*4001 restricted epitope.

In some embodiments, the peptide of the present invention is a HLA class II restricted epitope. In some embodiments, the peptide of the present invention is a HLA-DQA1*0101 or DQB1*0201 restricted epitope. In some embodiments, the peptide of the present invention is a HLA-DQA1*0301 or DQB1*0302 restricted epitope. In some embodiments, the peptide of the present invention is a HLA-DRB1*0101 epitope. In some embodiments, the peptide of the present invention is a HLA-DRB1*0301 restricted epitope. In some embodiments, the peptide of the present invention is a HLA-DRB1*0401 restricted epitope.

In some embodiments, the peptide of the present invention is an antibody epitope. As used herein, the term "antibody epitope" refers to peptide, which can be recognized by a specific antibody, or which induces the formation of specific antibodies.

In some embodiments, the peptide of the present invention is selected in Table A depicted in the EXAMPLE.

In some embodiments, the peptide consists of the amino acid sequence as set forth in (MLMPVHFL), SEQ ID NO: 2

(MLMPVHFLL), SEQ ID NO: 3

(MLMPVHFLLL), SEQ ID NO: 4

(MLMPVHFLLLL), SEQ ID NO: 5

(FLLLLLLLL), SEQ ID NO: 6

(LMPVHFLL), SEQ ID NO: 7

(LMPVHFLLL), SEQ ID NO: 8

(LMPVHFLLLL), SEQ ID NO: 9

(HFLLLLLLLL), SEQ ID NO: 10

(FLLLLLLL), SEQ ID NO: 11

(FLLLLLLLLG), SEQ ID NO: 12

(LLLGGPRTGL), SEQ ID NO: 13

(PRTGLPHKFYK), SEQ ID NO: 14

(RTGLPHKFYK), SEQ ID NO: 15

(GLPHKFYKAK), SEQ ID NO: 16

(MLMPVHFL), SEQ ID NO: 17

(MLMPVHFLL), SEQ ID NO: 18

(MLMPVHFLLL), SEQ ID NO: 19

(MPVHFLLL), SEQ ID NO: 20

(FLLLLLLLLGGPRTG), SEQ ID NO: 21

(LLLLLLLLGGPRTGL), SEQ ID NO: 22

-continued (LLLLLLLGGPRTGLP), (LLLLLLGGPRTGLPH), (GLPHKFYKAKPIFSC), (LPHKFYKAKPIFSCL), (GLPHKFYKAKPIFSC), (LPHKFYKAKPIFSCL), (PRTGLPHKFY), (GQWEDASLL), (SLLSKRSFHYL), (LLSKRSFHYL), (GQWEDASLLSK), (SLLSKRSFHY), (LLSKRSFHY), (RSFHYLRSR), (KFYKAKPIF), (YKAKPIFSCL), (SLLSKRSF), (LLSKRSFHYL), (YLRSRDASS), (PHKFYKAKPIFSCLN), (HKFYKAKPIFSCLNT), (KFYKAKPIFSCLNTA), (LSKRSFHYLRSRDAS), (SKRSFHYLRSRDASS), (KRSFHYLRSRDASSG), (RSFHYLRSRDASSGE), (SFHYLRSRDASSGEE),

SEQ ID NO: 23

SEQ ID NO: 24

SEQ ID NO: 25

SEQ ID NO: 26

SEQ ID NO: 27

SEQ ID NO: 28

SEQ ID NO: 29

SEQ ID NO: 30

SEQ ID NO: 31

SEQ ID NO: 32

SEQ ID NO: 33

SEQ ID NO: 34

SEQ ID NO: 35

SEQ ID NO: 36

SEQ ID NO: 37

SEQ ID NO: 38

SEQ ID NO: 39

SEQ ID NO: 40

SEQ ID NO: 41

SEQ ID NO: 42

SEQ ID NO: 43

SEQ ID NO: 44

SEQ ID NO: 45

SEQ ID NO: 46

SEQ ID NO: 47

SEQ ID NO: 48

SEQ ID NO: 49

-continued (EDASLLSKRSFHYLR), (DASLLSKRSFHYLRS), (ASLLSKRSFHYLRSR), (PHKFYKAKPIFSCLN), (HKFYKAKPIFSCLNT), (YKAKPIFSCLNTALS), (KAKPIFSCLNTALSE), (AKPIFSCLNTALSEA), (KPIFSCLNTALSEAE), (PIFSCLNTALSEAEK), (LSKRSFHYLRSRDAS), (SKRSFHYLRSRDASS), (KRSFHYLRSRDASSG), (RSFHYLRSRDASSGE), (SFHYLRSRDASSGEE), (PRTGLPHKFY), (LSEAEKGQWEDASL), (SRDASSGEEEEGKEKKTFPISGARGGARGTRYRYVSQAQPRGKPRQDTAKSPHRTK), (TLSLDVPTNI), (TNIMNLLFNI), (NIMNLLFNI), (IMNLLFNI), (IMNLLFNIAK), (MNLLFNIAKAK), (NLLFNIAKAK), (LLFNIAKAK),

SEQ ID NO: 50

SEQ ID NO: 51

SEQ ID NO: 52

SEQ ID NO: 53

SEQ ID NO: 54

SEQ ID NO: 55

SEQ ID NO: 56

SEQ ID NO: 57

SEQ ID NO: 58

SEQ ID NO: 59

SEQ ID NO: 60

SEQ ID NO: 61

SEQ ID NO: 62

SEQ ID NO: 63

SEQ ID NO: 64

SEQ ID NO: 65

SEQ ID NO: 66

SEQ ID NO: 67

SEQ ID NO: 68

SEQ ID NO: 69

SEQ ID NO: 70

SEQ ID NO: 71

SEQ ID NO: 72

SEQ ID NO: 73

SEQ ID NO: 74

SEQ ID NO: 75

(AHLMAQIGRK), SEQ ID NO: 76

(HLMAQIGRK), SEQ ID NO: 77

(HLMAQIGRKK), SEQ ID NO: 78

(LMAQIGRKK), SEQ ID NO: 79

(IMNLLFNIAKAKNLR), SEQ ID NO: 80

(MNLLFNIAKAKNLRA), SEQ ID NO: 81

(NLLFNIAKAKNLRAQ), SEQ ID NO: 82

(LLFNIAKAKNLRAQA), SEQ ID NO: 83

(LFNIAKAKNLRAQAA), SEQ ID NO: 84

(AKAKNLRAQAAANAH), SEQ ID NO: 85

(KAKNLRAQAAANAHL), SEQ ID NO: 86

(AKNLRAQAAANAHLM), SEQ ID NO: 87

(KNLRAQAAANAHLMA), SEQ ID NO: 88

(FTLSLDVPTNIMNLL), SEQ ID NO: 89

(TLSLDVPTNIMNLLF), SEQ ID NO: 90

(IMNLLFNIAKAKNLR), SEQ ID NO: 91

(MNLLFNIAKAKNLRA), SEQ ID NO: 92

(NLLFNIAKAKNLRAQ), SEQ ID NO: 93

(LLFNIAKAKNLRAQA), SEQ ID NO: 94

(LFNIAKAKNLRAQAA), SEQ ID NO: 95

(MNLLFNIAKAKNLRA), SEQ ID NO: 96

(NLLFNIAKAKNLRAQ), SEQ ID NO: 97

(LLFNIAKAKNLRAQA), SEQ ID NO: 98

(LFNIAKAKNLRAQAA), SEQ ID NO: 99

(KAKNLRAQAAANAHL), SEQ ID NO: 100

(AKNLRAQAAANAHLM), SEQ ID NO: 101

(KNLRAQAAANAHLMA), SEQ ID NO: 102 or (NLRAQAAA). SEQ ID NO: 103

In some embodiments, the peptide of the present invention is fused to a heterologous polypeptide to form a fusion protein. As used herein, a "fusion protein" comprises all or part (typically biologically active) of a peptide of the present invention operably linked to a heterologous polypeptide (i.e., a polypeptide which does not derive from the same protein). Within the fusion protein, the term "operably linked" is intended to indicate that the peptide of the present invention and the heterologous polypeptide are fused in-frame to each other. The heterologous polypeptide can be fused to the N-terminus or C-terminus of the peptide of the present invention.

In some embodiments, the peptide of the present invention is fused either directly or via a linker to the heterologous polypeptide. As used herein, the term "directly" means that the (first or last) amino acid at the terminal end (N or C-terminal end) of the peptide of the present invention is fused to the (first or last) amino acid at the terminal end (N or C-terminal end) of heterologous polypeptide. This direct fusion can occur naturally as described in (Vigneron et al., Science 2004, PMID 15001714), (Warren et al., Science 2006, PMID 16960008), (Berkers et al., J. Immunol. 2015a, PMID 26401000), (Berkers et al., J. Immunol. 2015b, PMID 26401003), (Delong et al., Science 2016, PMID 26912858) (Liepe et al., Science 2016, PMID 27846572), (Babon et al., Nat. Med. 2016, PMID 27798614). In this case, a sequence stretch shorter than 8 amino acids of the peptide of the present invention can be fused with a heterologous peptide. As used herein, the term "linker" refers to a sequence of at least one amino acid that links the peptide of the present invention with the heterologous polypeptide. Linkers are well known to one of ordinary skill in the art and typically comprises 1, 2, 3, 4, 5, 6, 7, 8, 9, 10, 11, 12, 13, 14, 15, 16, 17, 18, 19, 20 or more amino acids.

In some embodiments, the heterologous polypeptide comprises at least one redox motif C-(X)2-[CST] or [CST]-(X)2-C. In some embodiments, the C-(X)2-[CST] or [CST]-(X)2-C motif is positioned N-terminally of the peptide of the present invention. In some embodiments, the fusion protein of the invention contains the sequence motif C-X(2)-[CS] or [CS]-X(2)-C. In some embodiments the fusion protein of the invention contain the sequence motif C-X(2)-S, S-X(2)-C or C-X(2)-C. C-(X)2-[CST] or [CST]-(X)2-C motif.

As used herein, the symbol X is used for a position where any amino acid is accepted. Alternatives are indicated by listing the acceptable amino acids for a given position, between square brackets ('[ ]'). For example: [CST] stands for an amino acid selected from Cys, Ser or Thr. The different elements in a motif are separated from each other by a hyphen "-". Repetition of an identical element within a motif can be indicated by placing behind that element a numerical value or a numerical range between parentheses. For example: X(2) corresponds to X-X, X(2, 4) corresponds to X-X or X-X-X or X-X-X-X, A(3) corresponds to A-A-A.

In some embodiments, C represents either cysteine or another amino acid with a thiol group such as mercaptovaline, homocysteine or other natural or non-natural amino acids with a thiol function. In order to have reducing activity, the cysteines present in the redox motif should not occur as part of a cysteine disulfide bridge. Nevertheless, the redox motif may comprise modified cysteines such as methylated cysteine, which is converted into cysteine with free thiol groups in vivo.

In some embodiments, each of the amino acids X in the C-(X)2-[CST] or [CST]-(X)2-C motif can be any natural amino acid, including S, C, or T or can be a non-natural amino acid, whereby the two amino acids X are either the same or different. In some embodiments X is an amino acid with a small side chain such as Gly, Ala, Ser or Thr. In some embodiments, X is not an amino acid with a bulky side chain such as Tyr. In some embodiments at least one X in the [CST]-X(2)-[CST] motif is His or Pro.

In some embodiments, the redox motif is placed either immediately adjacent to the peptide sequence within the fusion protein, or is separated from the peptide by a linker as defined herein. In some embodiments, the linker comprises an amino acid sequence of 7 amino acids or less. In some embodiments, the linker comprises 1, 2, 3, or 4 amino acids. In some embodiments, a linker may comprise 6, 8 or 10 amino acids. Typical amino acids used in linkers are serine and threonine. Example of peptides with linkers in accordance with the present invention are CXXC-G-peptide, CXXC-GG-peptide, CXXC-SSS-e peptide, CXXC-SGSG-peptide and the like.

In some embodiments, the redox motif occurs several times (1, 2, 3, 4 or even more times) in the fusion protein, for example as repeats of the redox motif which can be spaced from each other by one or more amino acids (e.g. CXXC X CXXC X CXXC), as repeats which are adjacent to each other (e.g. CXXC CXXC CXXC) or as repeats which overlap with each other (e.g. CXXCXXCXXC or CXCCXCCXCC). In some embodiments, one or more motifs are provided at both the N and the C terminus of the peptide of the present invention. Other variations envisaged for the fusion proteins of the present invention include fusion proteins containing repeats of a peptide of the present invention wherein each peptide is preceded and/or followed by the redox motif (e.g. repeats of "motif-peptide" or repeats of "motif-peptide-motif"). Herein the redox motifs can all have the same sequence, but this is not obligatory.

In some embodiments, the fusion protein of the invention further comprises an amino acid sequence facilitating uptake of the peptide into (late) endosomes for processing and presentation. The late endosome targeting is mediated by signals present in the cytoplasmic tail of proteins and correspond to well-identified peptide motifs such as the dileucine-based [DE]XXXL[LI] or DXXLL motif (e.g. DXXXLL), the tyrosine-based YXXØ motif or the so-called acidic cluster motif. The symbol Ø represents amino acid residues with a bulky hydrophobic side chains such as Phe, Tyr and Trp. The late endosome targeting sequences allow for processing and efficient presentation of the peptide of the present invention by antigen presenting cells (APCs). Such endosomal targeting sequences are contained, for example, within the gp75 protein (Vijayasaradhi et al. (1995) J Cell Biol 130, 807-820), the human CD3 gamma protein, the HLA-DM β (Copier et al. (1996) J. Immunol. 157, 1017-1027), the cytoplasmic tail of the DEC205 receptor (Mahnke et al. (2000) J Cell Biol 151, 673-683). Other examples of peptides which function as sorting signals to the endosome are disclosed in the review of Bonifacio and Traub (2003) Annu. Rev. Biochem. 72, 395-447. In some embodiments, the sequence can be that of a subdominant or minor T cell epitope from a protein, which facilitates uptake in late endosome without overcoming the T cell response towards the alloantigen-derived T cell epitope.

In some embodiments, the fusion protein of the present invention comprises an amino acid sequence consisting of a portion of an Fc region fused to the amino acid sequence of the peptide of the present invention.

As used herein, the term "Fc region" includes amino acid sequences derived from the constant region of an antibody heavy chain. The Fc region is the portion of a heavy chain constant region of an antibody beginning at the N-terminal of the hinge region at the papain cleavage site, at about position 216 according to the EU index and including the hinge, CH2, and CH3 domains. Exemplary Fc regions or portions thereof that may be used in the practice of the invention are well known in the art.

In some embodiments, the Fc region is an Fc region that confers binding to FcRn. As used herein, the term "neonatal Fc receptor" or "FcRn" has its general meaning in the art and refers to the neonatal Fc receptor which is an Fc receptor. Unlike FcγRs which belong to the Immunoglobulin superfamily, human FcRns structurally resemble polypeptides of Major Histocompatibility Complex (MHC) Class I. FcRn is typically expressed as a heterodimer consisting of a transmembrane α or heavy chain in complex with a soluble β or light chain (β2 microglobulin). FcRn shares 22-29% sequence identity with Class I MHC molecules has a non-functional version of the MHC peptide binding groove. Like MHC, the α chain of FcRn consists of three extracellular domains (α1, α2, α3) and a short cytoplasmic tail that anchors the protein to the cell surface. The α1 and α2 domains interact with FcR binding sites in the Fc region of antibodies.

Accordingly, in some embodiments, the Fc region is the Fc region of an IgG antibody, preferably of an IgG1 or IgG4 antibody, even more preferably of an IgG1 antibody, or a portion of the Fc that is sufficient to permit to FcRn.

In some embodiments, the Fc region of the fusion protein includes substantially the entire Fc region of an antibody, beginning in the hinge region just upstream of the papain cleavage site which defines IgG Fc chemically (about residue 216 EU numbering, taking the first residue of heavy chain constant region to be 114) and ending at its C-terminus. The precise site at which the fusion is made is not critical; particular sites are well known and may be selected in order to optimize the biological activity, secretion, or binding characteristics of the molecule. Methods for making fusion proteins are known in the art. As used herein, the term "hinge region" includes the portion of a heavy chain molecule that joins the CH1 domain to the CH2 domain, e.g. from about position 216-230 according to the EU number system. This hinge region comprises approximately 25 residues and is flexible, thus allowing the two N-terminal antigen binding regions to move independently. Hinge regions can be subdivided into three distinct domains: upper, middle, and lower hinge domains. As used herein, the term "CH2 domain" includes the portion of a heavy chain molecule that extends, e.g., from about EU positions 231-340. The CH2 domain is unique in that it is not closely paired with another domain. Rather, two N-linked branched carbohydrate chains are interposed between the two CH2 domains of an intact native IgG molecule. As used herein, the term "CH3 domain" includes the portion of a heavy chain molecule that extends approximately 110 residues from N-terminus of the CH2 domain, e.g., from about residue 341-446, EU numbering system). The CH3 domain typically forms the C-terminal portion of the antibody. In some immunoglobulins, however, additional domains may extend from CH3 domain to form the C-terminal portion of the molecule (e.g. the CH4 domain in the chain of IgM and the E chain of IgE).

In some embodiments, the Fc region of the fusion protein does not include the hinge region but comprises the CH2 and CH3 domains that is fused to the amino acid sequence that comprises the antigenic portion of the antigen.

Further methods of reducing the size of the constructs may also be employed, such as those described in US patent applications 2002/0155537, 2007/0014794, and 2010/0254986 (each to Carter et al.), and 2014/0294821 (Dumont et al.). For example, Fc-Fc and antigen-Fc/antigen-Fc dimer formation may be prevented. In some embodiments, the Fc region may be mutated in order to increase the binding affinity or specificity for the FcRn. Examples of such mutations include, but are not limited to, H435A, N434A and M428L modifications. In some embodiments, the Fc region may be mutated in order to limit enzymatic degradation, e.g. from pepsin.

The peptides and fusion proteins of the invention may be produced by any technique known per se in the art, such as, without limitation, any chemical, biological, genetic or enzymatic technique, either alone or in combination. Knowing the amino acid sequence of the desired sequence, one skilled in the art can readily produce said polypeptides, by standard techniques for production of polypeptides. For instance, they can be synthesized using well-known solid phase method, preferably using a commercially available peptide synthesis apparatus (such as that made by Applied Biosystems, Foster City, California) and following the manufacturer's instructions. Alternatively, the polypeptides and fusions proteins of the invention can be synthesized by recombinant DNA techniques as is now well-known in the art. For example, these fragments can be obtained as DNA expression products after incorporation of DNA sequences encoding the desired (poly) peptide into expression vectors and introduction of such vectors into suitable eukaryotic or prokaryotic hosts that will express the desired polypeptide, from which they can be later isolated using well-known techniques.

In some embodiments, the peptide of the present invention is fused or conjugated to an antibody for forming an "immunoconjugate".

As used herein, the term "antibody" is thus used to refer to any antibody-like molecule that has an antigen binding region, and this term includes antibody fragments that comprise an antigen binding domain such as Fab', Fab, F(ab')2, single domain antibodies (DABs or VHH), TandAbs dimer, Fv, scFv (single chain Fv), dsFv, ds-scFv, Fd, linear antibodies, minibodies, diabodies, bispecific antibody fragments, bibody, tribody (scFv-Fab fusions, bispecific or trispecific, respectively); sc-diabody; kappa(lambda) bodies (scFv-CL fusions); DVD-Ig (dual variable domain antibody, bispecific format); SIP (small immunoprotein, a kind of minibody); SMIP ("small modular immunopharmaceutical" scFv-Fc dimer; DART (ds-stabilized diabody "Dual Affinity ReTargeting"); small antibody mimetics comprising one or more CDRs and the like. In some embodiments, the antibody is a chimeric antibody, a humanized antibody or a human antibody. The techniques for preparing and using various antibody-based constructs and fragments are well known in the art. Significantly, as is well-known in the art, only a small portion of an antibody molecule, the paratope, is involved in the binding of the antibody to its epitope (see, in general, Clark, W. R. (1986) The Experimental Foundations of Modern Immunology Wiley & Sons, Inc., New York; Roitt, I. (1991) Essential Immunology, 7th Ed., Blackwell Scientific Publications, Oxford). The Fc' and Fc regions, for example, are effectors of the complement cascade but are not involved in antigen binding. An antibody from which the pFc' region has been enzymatically cleaved, or which has been produced without the pFc' region, designated an F(ab')2 fragment, retains both of the antigen binding sites of an intact antibody. Similarly, an antibody from which the Fc region has been enzymatically cleaved, or which has been produced without the Fc region, designated a Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinants of antibody specificity (a single Fd fragment may be associated with up to ten different light chains without altering antibody specificity) and Fd fragments retain epitope-binding ability in isolation. Thus, as will be apparent to one of ordinary skill in the art, the present invention also provides for F(ab') 2 Fab, Fv and Fd fragments. Antibodies can be indeed fragmented using conventional techniques. For example, F(ab')2 fragments can be generated by treating the antibody with pepsin. The resulting F(ab')2 fragment can be treated to reduce disulfide bridges to produce Fab' fragments. Papain digestion can lead to the formation of Fab fragments. Fab, Fab' and F(ab')2, scFv, Fv, dsFv, Fd, dAbs, TandAbs, ds-scFv, dimers, minibodies, diabodies, bispecific antibody fragments and other fragments can also be synthesized by recombinant techniques or can be chemically synthesized. Techniques for producing antibody fragments are well known and described in the art. For example, each of Beckman et al., 2006; Holliger & Hudson, 2005; Le Gall et al., 2004; Reff & Heard, 2001; Reiter et al., 1996; and Young et al., 1995 further describe and enable the production of effective antibody fragments. The various antibody molecules and fragments may derive from any of the commonly known immunoglobulin classes, including but not limited to IgA, secretory IgA, IgE, IgG and IgM. IgG subclasses are also well known to those in the art and include but are not limited to human IgG1, IgG2, IgG3 and IgG4. The present invention also includes so-called single chain antibodies. The term "single domain antibody" (sdAb) or "VHH" refers to the single heavy chain variable domain of antibodies of the type that can be found in Camelid mammals which are naturally devoid of light chains. Such VHH are also called "Nanobody®". According to the invention, sdAb can particularly be llama sdAb.

Typically, the antibody is directed against a surface antigen of an APC so that the peptide of the present invention is targeted to said cell to elicit an immune response (e.g. tolerance). As used herein the term "APCs" or "Antigen Presenting Cells" denotes cells that are capable of activating T-cells, and include, but are not limited to, certain macrophages, B cells and dendritic cells. In some embodiments, the antibody is directed against a surface antigen of a dendritic cell. "Dendritic cells" (DCs) refer to any member of a diverse population of morphologically similar cell types found in lymphoid or non-lymphoid tissues. These cells are characterized by their distinctive morphology, high levels of surface MHC-class II expression (Steinman, et al., Ann. Rev. Immunol. 9:271 (1991); incorporated herein by reference for its description of such cells). These cells can be isolated from a number of tissue sources, and conveniently, from peripheral blood, as described herein. Accordingly, the antibody is selected from an antibody that specifically binds to DC immunoreceptor (DCIR), MHC class I, MHC class II, CD1, CD2, CD3, CD4, CD8, CD1 1b, CD14, CD15, CD16, CD19, CD20, CD29, CD31, CD40, CD43, CD44, CD45, CD54, CD56, CD57, CD58, CD83, CD86, CMRF-44, CMRF-56, DCIR, DC-ASPGR, CLEC-6, CD40, BDCA-2, MARCO, DEC-205, mannose receptor, Langerin, DECTIN-1, B7-1, B7-2, IFN-γ receptor and IL-2 receptor, ICAM-1, Fey receptor, LOX-1, and ASPGR. In some embodiments, the antibody is specific for a cell surface marker of a professional APC. Preferably, the antibody is specific for a cell surface marker of a DC, for example, CD83, CMRF-44 or CMRF-56. The antibody may be specific for a cell surface marker of another professional APC, such as a B cell or a macrophage. CD40 is expressed on both DCs, B cells, and other APCs so that a larger number of APCs would be recruited.

Techniques for conjugating molecule to antibodies, are well-known in the art (See, e.g., Arnon et al., "Monoclonal Antibodies For Immunotargeting Of Drugs In Cancer Therapy," in Monoclonal Antibodies And Cancer Therapy (Reisfeld et al. eds., Alan R. Liss, Inc., 1985); Hellstrom et al., "Antibodies For Drug Delivery," in Controlled Drug Delivery (Robinson et al. eds., Marcel Deiker, Inc., 2nd ed. 1987); Thorpe, "Antibody Carriers Of Cytotoxic Agents In Cancer Therapy: A Review," in Monoclonal Antibodies '84: Biological And Clinical Applications (Pinchera et al. eds., 1985); "Analysis, Results, and Future Prospective of the Therapeutic Use of Radio labeled Antibody In Cancer Therapy," in Monoclonal Antibodies For Cancer Detection And Therapy (Baldwin et al. eds., Academic Press, 1985); and Thorpe et al., 1982, Immunol. Rev. 62:119-58; see also, e.g., PCT publication WO 89/12624.) Typically, the peptide is covalently attached to lysine or cysteine residues on the antibody, through N-hydroxysuccinimide ester or maleimide functionality respectively. Methods of conjugation using engineered cysteines or incorporation of unnatural amino acids have been reported to improve the homogeneity of the conjugate (Axup, J. Y., Bajjuri, K. M., Ritland, M., Hutchins, B. M., Kim, C. H., Kazane, S. A., Halder, R., Forsyth, J. S., Santidrian, A. F., Stafin, K., et al. (2012). Synthesis of site-specific antibody-drug conjugates using unnatural amino acids. Proc. Natl. Acad. Sci. USA 109, 16101-16106.; Junutula, J. R., Flagella, K. M., Graham, R. A., Parsons, K. L., Ha, E., Raab, H., Bhakta, S., Nguyen, T., Dugger, D. L., Li, G., et al. (2010). Engineered thiotrastuzumab-DM1 conjugate with an improved therapeutic index to target human epidermal growth factor receptor 2-positive breast cancer. Clin. Cancer Res. 16, 4769-4778). Junutula et al. (Nat Biotechnol. 2008; 26:925-32) developed cysteine-based site-specific conjugation called "THIO-MABs" (TDCs) that are claimed to display an improved therapeutic index as compared to conventional conjugation methods. Conjugation to unnatural amino acids that have been incorporated into the antibody is also being explored for ADCs; however, the generality of this approach is yet to be established (Axup et al., 2012). In particular the one skilled in the art can also envisage Fc-containing polypeptide engineered with an acyl donor glutamine-containing tag (e.g., Gin-containing peptide tags or Q-tags) or an endogenous glutamine that are made reactive by polypeptide engineering (e.g., via amino acid deletion, insertion, substitution, or mutation on the polypeptide). Then a transglutaminase can covalently crosslink with an amine donor agent (e.g., a small molecule comprising or attached to a reactive amine) to form a stable and homogenous population of an engineered Fc-containing polypeptide conjugate with the amine donor agent being site-specifically conjugated to the Fc-containing polypeptide through the acyl donor glutamine-containing tag or the accessible/exposed/reactive endogenous glutamine (WO 2012059882).

The peptide, fusion protein and the immunoconjugate as described herein may be administered as part of one or more pharmaceutical compositions. The term "pharmaceutical composition" refers to a composition described herein, or pharmaceutically acceptable salts thereof, with other agents such as carriers and/or excipients. The pharmaceutical compositions as provided herewith typically include a pharmaceutically acceptable carrier. The term "pharmaceutically acceptable carrier" includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical-Sciences, Sixteenth Edition, E. W. Martin (Mack Publishing Co., Easton, Pa., 1980) discloses various carriers used in formulating pharmaceutical compositions and known techniques for the preparation thereof. Except insofar as any conventional carrier medium is incompatible with the peptides of the present invention, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatine; talc; excipients such as cocoa butter and suppository waxes; oils such as peanut oil, cottonseed oil; safflower oil, sesame oil; olive oil; corn oil and soybean oil; glycols; such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

In particular, the peptide, fusion protein and the immunoconjugate as described herein are particularly suitable for preparing vaccine composition. For the purpose of the present invention, the term "vaccine composition" is intended to mean a composition which can be administered to humans or to animals in order to induce an immune system response; this immune system response can result in the activation of certain cells, in particular APCs, T lymphocytes and B lymphocytes. Accordingly, in some embodiments, the vaccine composition of the present invention comprises an adjuvant. The term "adjuvant" can be a compound that lacks significant activity administered alone but can potentiate the activity of another therapeutic agent. In some embodiments, the adjuvant is alum. In some embodiments, the adjuvant is Incomplete Freund's adjuvant (IFA) or other oil based adjuvant that is present between 30-70%, preferably between 40-60%, more preferably between 45-55% proportion weight by weight (w/w). In some embodiments, the vaccine composition of the present invention comprises at least one Toll-Like Receptor (TLR) agonist which is selected from the group consisting of TLR1, TLR2, TLR3, TLR4, TLR5, TLR6, TLR7, and TLR8 agonists.

The peptide, fusion protein, immunoconjugate or pharmaceutical composition of the present invention is particularly suitable for inducing immune tolerance. As used herein, the term "immune tolerance" refers to a state of unresponsiveness of the immune system to substances or tissues that have the capacity to elicit an immune response. Peptides of the invention are thus useful for achieving tolerance or partial tolerance. As used herein, a "partial tolerance" results in a reduced immune response. As used herein, the term "immune response" includes T cell mediated and/or B cell mediated immune responses. Exemplary immune responses include T cell responses, e.g., cytokine production and cellular cytotoxicity. In addition, the term immune response includes immune responses that are indirectly affected by T cell activation, e.g., antibody production (humoral responses) and activation of cytokine responsive cells, e.g., macrophages. Immune cells involved in the immune response include lymphocytes, such as B cells and T cells (CD4+, CD8+, Treg, Tr1, Th1, Th2, Th3 and Th17 cells); APCs (e.g. professional APCs such as DCs); natural killer cells; myeloid cells, such as macrophages, eosinophils, mast cells, basophils, and granulocytes.

The peptide, fusion protein, immunoconjugate or pharmaceutical composition of the present invention may be administered to the subject by any route of administration and in particular by oral, nasal, rectal, topical, buccal (e.g., sub-lingual), parenteral (e.g., subcutaneous, intramuscular, intradermal, or intravenous) and transdermal administration, although the most suitable route in any given case will depend on the nature and severity of the condition being treated and on the nature of the particular active agent which is being used.

Accordingly, the peptide, fusion protein or immunoconjugate of the present invention is particularly suitable for the treatment of type 1 diabetes (T1DM) in a subject in need thereof.

As used herein, the term "type 1 diabetes", "insulin-dependent diabetes mellitus," "IDDM," "type 1 diabetes mellitus," and "T1DM," refer to diseases characterized by the autoimmune destruction of the β cells in the pancreatic islets of Langerhans. Such diseases can be diagnosed during their clinical phase characterized by the onset of dysglycemia or hyperglycemia (a dysregulated glucose metabolism) or during their preclinical phase characterized by the presence of active β-cell autoimmunity with positivity for islet autoantibodies, such as those targeting insulin, glutamic acid decarboxylase (GAD), islet-associated antigen (IA)-2 and zinc transporter (ZnT)8.

In some embodiments, the subject is diagnosed as being at risk for developing T1DM. The means of assessing this risk are known to the experts in the field, e.g. when the subject presents a family history of T1DM and/or harbours the genetic background associated with T1DM, including, but not limited to, susceptible HLA Class II alleles such as HLA-DR3, HLA-DR4, HLA-DQ2, HLA-DQ8.

In some embodiments, the subject is diagnosed in the preclinical phase of T1DM and is said to present asymptomatic islet autoimmunity. This condition is associated with the presence of islet autoantibodies such as those against insulin, GAD, IA-2 and ZnT8, which is not accompanied by detectable alternations in glucose metabolism.

In some embodiments, the subject is diagnosed in the early clinical phase of T1D. This phase is associated with blood glucose level which is still normal, while the capacity of β cells to secrete insulin starts to be compromised. This compromised capacity can be evaluated with glucose challenge tests known to the experts in the field, e.g. using an oral glucose tolerance test (OGTT), a mixed meal tolerance test (MMTT) or a glucagon-stimulated insulin release test.

In some embodiments, the subject has been recently diagnosed with clinical T1DM. When used herein, the expression "recent diagnosis of T1DM" or "recently diagnosed T1DM" refers to the patient in whom T1DM has either been recently or newly diagnosed, e.g. wherein the patient has been diagnosed with T1DM within about 3 months of initial treatment, and/or wherein the patient's T1DM is in early stages or is not advanced, e.g. wherein the patient is determined to have functioning β cells, for instance as determined by a blood test such as C-peptide in which a detectable level of C-peptide (e.g. >0.03 nmol/L in the fasting state of >0.2 nmol/L when stimulated by a caloric load such as an MMTT).

As used herein, the term "treatment" or "treating a subject" is defined as the application or administration of a therapeutic agent to a patient or at-risk subject, or application or administration of a therapeutic agent to an isolated tissue or cell line from a patient or at-risk subject, who has a disease, a symptom of disease or a predisposition toward a disease. Treatment can slow, cure, heal, alleviate, relieve, alter, remedy, ameliorate, improve or affect the disease, the symptoms of disease or the predisposition toward disease. For example, treatment of a subject, e.g., a human subject, with a composition described herein, can slow, improve, or stop the ongoing autoimmunity, e.g., a reaction against pancreatic β cells, in a subject before, during, or after the clinical onset of T1DM. Therefore, the method of the invention can prevent T1DM, or prevent or delay loss of residual β-cell mass, providing a longer remission period reducing short term complications and/or delaying the onset of diabetes-related complications at a later stage in life. The onset of T1DM may be delayed by the method as described herein such that insulin is not needed by the subject for a longer length of time. Alternatively or in addition, the present method may extend the "honeymoon phase" in an already diabetic subject. The honeymoon phase is where insulin is secreted by the pancreas, causing high blood sugar levels to subside, and resulting in normal or near-normal glucose levels due to responses to insulin injections and treatment. The method of the present invention is also used to arrest the autoimmune destruction of tissue, e.g., pancreatic β-cells. The method of the present invention is suitable to arrest the autoimmune destruction, even at a late stage at the time of clinical onset of T1DM or after clinical onset. For example, at the time of clinical onset of T1DM, significant number of insulin producing β cells is destroyed. If the autoimmune process can be arrested even in this late stage or as far as residual secretion can be restored, these cells can be preserved. The β cells have some limited capacity to replicate and precursors may form new β cells. The phrase "delaying the progression", as used herein in the context of delaying the progression of T1DM, means that the loss of functional residual β-cell mass, after the clinical onset of T1DM is delayed. The delayed progression of T1DM can be assessed, for example, by measuring C-peptide production.

Typically, the active ingredient of the present invention (i.e. peptide, fusion protein and the immunoconjugate as described herein) is administered to the subject at a therapeutically effective amount. By a "therapeutically effective amount" is meant a sufficient amount of the active ingredient of the present invention to induce tolerance at a reasonable benefit/risk ratio applicable to any medical treatment. It will be understood that the total daily usage of the compounds and compositions of the present invention will be decided by the attending physician within the scope of sound medical judgment. The specific therapeutically effective dose level for any particular subject will depend upon a variety of factors including the disorder being treated and the severity of the disorder; the activity of the specific compound employed; the specific composition employed, the age, body weight, general health, sex and diet of the subject; the time of administration, route of administration, and rate of excretion of the specific compound employed; the duration of the treatment; drugs used in combination or coincidental with the specific polypeptide employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. In particular, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, in particular from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

In some embodiments, the peptides, fusions proteins and immunoconjugates as herein described are used in combination with, for example, any known therapeutic agent or method for treating T1DM. Non-limiting examples of such known therapeutics for treating T1DM include insulin, insulin analogs, islet transplantation, stem cell therapy including PROCHYMAL®, non-insulin therapies such as IL-113 inhibitors (Canakinumab, Anakinra, Kineret®), Diamyd GAD65, Alefacept (Ameviv®), anti-CD3 antibodies such as Otelixizumab and Teplizumab, DiaPep277 (Hsp60-derived peptide), α-1-antitrypsin, Prednisone, Azathioprine, Ciclosporin, El-INT (an injectable islet neogenesis therapy comprising an epidermal growth factor analog and a gastrin analog), statins including Zocor®, Simlup®, Simcard®, Simvacor®, Sitagliptin (dipeptidyl peptidase (DPP-4) inhibitor), anti-CD20 mAb (e.g, rituximab). In some embodiments, the peptides, fusions proteins and immunoconjugates as herein described are used in combination with a GABA agonist. Illustrative GABA receptor agonists include, but are not limited to, certain barbiturates (e.g., thiopental, thiamylal, pentobarbital, secobarbital, hexobarbital, butobarbital, amobarbital, barbital, mephobarbital, phenobarbital, primidone, and the like), certain benzodiazepines (e.g., midazolam, triazolam, lometazepam, flutazolam, nitrazepam, fluritrazepam, nimetazepam, diazepam, medazepam, oxazolam, prazeam, tofisopam, rilmazafonoe, lorazepam, temazepam, oxazepam, fluidazepam, chlordizaepoxide, cloxazolam, flutoprazepam, alprazolam, estazolam, bromazepam, flurazepam, clorazepate potassium, haloxazolam, ethyl loflazepate, qazepam, clonazepam, mexazolam, and the like), certain thienodiazepiens (e.g., etizolam, brotizolam, clotiazepam, and the like), certain dialkylphenols (e.g., propofol, fospropofol, and the like), certain non-benzodiazepines (e.g., Zolpidem, zopiclone, exzopiclone), and the like. In some embodiments, the peptides, fusion proteins or immunoconjugates as described herein are used in combination with a CTLA-4 molecule. As used herein, a "CTLA-4 molecule" is a molecule comprising a cytotoxic T-lymphocyte-associated antigen 4 (CTLA-4) extracellular domain. In some embodiments, the extracellular domain of CTLA-4 comprises a portion of the CTLA-4 protein that recognizes and binds to at least one B7 (CD80/86) antigen such as a B7 antigen expressed on B cells and on APCs. The B cells and APCs may be activated. The extracellular domain may also include fragments or derivatives of CTLA-4 that bind a B7 antigen. The CTLA-4 extracellular domain can also recognize and bind CD80 and/or CD86. The extracellular domain may also include fragments or derivatives of CTLA-4 that bind a binds CD80 and/or CD86. The CTLA-4 molecule may be a fusion protein, where a fusion protein is defined as one or more amino acid sequences joined together using methods well known in the art. The joined amino acid sequences thereby form one fusion protein. In some embodiments, the CTLA-4 molecule contains at least a portion of an immunoglobulin, such as the Fc portion of an immunoglobulin. In some embodiments, the CTLA-4 molecule is an isolated and purified CTLA-4 molecule. In some embodiments, the CTLA-4 molecule is a protein containing at least a portion of an immunoglobulin, such as the Fc portion of an immunoglobulin. In some embodiments, the CTLA-4 molecule is an isolated and purified CTLA-4 molecule. In some preferred embodiments, the CTLA-4 molecule is abatacept. Abatacept is a soluble fusion protein that consists of the extracellular domain of human CTLA-4 linked to the modified Fc (hinge, CH2, and CH3 domains) portion of human immunoglobulin G1 (IgG1). Abatacept is produced by recombinant DNA technology in a mammalian cell expression system. The apparent molecular weight of abatacept is 92 kilodaltons. Abatacept was developed by Bristol-Myers Squibb and is disclosed, for example, in U.S. Pat. Nos. 5,851,795, 7,455, 835, and U.S. Pat. Pub. 20011/311529.

A further object of the present invention relates to a nucleic acid molecule that encodes for a peptide or fusion protein of the present invention. Typically, said nucleic acid molecule is a DNA or RNA molecule, which may be included in any suitable vector, such as a plasmid, cosmid, episome, artificial chromosome, phage or a viral vector.

The nucleic acid molecule of the present invention is particularly suitable for the treatment of TD1M in a subject in need thereof.

A wide variety of methods exist to deliver nucleic acid molecules to subjects, as defined herein. For example, the nucleic acid molecule of the present invention can be formulated with cationic polymers including cationic liposomes. Other liposomes also represent effective means to formulate and deliver self-acid nucleic molecule. Alternatively, the DNA can be incorporated into a viral vector, viral particle, or bacterium for pharmacologic delivery. Viral vectors can be infection competent, attenuated (with mutations that reduce capacity to induce disease), or replication-deficient. Methods utilizing DNA to prevent the deposition, accumulation, or activity of pathogenic self-proteins may be enhanced by use of viral vectors or other delivery systems that increase humoral responses against the encoded autoantigen. In some embodiments, the DNA can be conjugated to solid supports including gold particles, polysaccharide-based supports, or other particles or beads that can be injected, inhaled, or delivered by particle bombardment (ballistic delivery). Methods for delivering nucleic acid preparations are known in the art. See, for example, U.S. Pat. Nos. 5,399,346, 5,580,859, and 5,589,466. A number of viral based systems have been developed for transfer into mammalian cells. For example, retroviral systems have been described (U.S. Pat. No. 5,219,740; Miller et al, Biotechniques 7:980-990 (1989); Miller, Human Gene Therapy 1: 5-14, (1990); Scarpa et al, Virology 180:849-852 (1991); Burns et al, Proc. Natl Acad. Sci. USA 90:8033-8037

(1993); and, Boris-Lawrie and Temin, Cur. Opin. Genet. Develop. 3: 102-109 (1993). A number of adenovirus vectors have also been described, see e.g., Haj-Ahmad et al., J. Virol. 57:267-274 (1986); Bett et al., J. Virol. 67:591 1-5921 (1993); Mittereder et al, Human Gene Therapy 5:717-729 (1994); Seth et al., J. Virol. 68:933-940 (1994); Barr et al, Gene Therapy 1:51-58 (1994); Berkner, BioTechniques 6:616-629 (1988); and, Rich et al, Human Gene Therapy 4:461-476 (1993). Adeno-associated virus (AAV) vector systems have also been developed for nucleic acid delivery. AAV vectors can be readily constructed using techniques well known in the art. See, e.g., U.S. Pat. Nos. 5,173,414 and 5,139,941; International Publication Nos. WO 92/01070 and WO 93/03769; Lebkowski et al, Molec. Cell Biol. 8:3988-3996 (1988); Vincent et al, Vaccines 90 (Cold Spring Harbor Laboratory Press) (1990); Carter, Current Opinion in Biotechnology 3:533-539 (1992); Muzyczka, Current Topics in Microbiol. And Immunol. 158:97-129 (1992); Kotin, Human Gene Therapy 5:793-801 (1994); Shelling et al., Gene Therapy 1: 165-169 (1994); and, Zhou et al., J. Exp. Med. 179: 1867-1875 (1994).

In some embodiments, the nucleic acid molecule of the present invention is delivered without a viral vector. For example, the nucleic acid molecule can be packaged in liposomes prior to delivery to the subject. Lipid encapsulation is generally accomplished using liposomes which are able to stably bind or entrap and retain nucleic acid. For a review of the use of liposomes as carriers for delivery of nucleic acids, see, e.g., Hug et al, Biochim. Biophys. Acta. 1097: 1-17 (1991); Straubinger et al., in Methods of Enzymology, 101: 512-527 (1983). Alternatively, the nucleic acid molecule is delivered via electroporation (i.e. muscular delivery by electroporation).

In some embodiments, the nucleic acid molecule is delivered by intramuscular ("IM") injection. In some embodiments, the acid nucleic molecule of the present invention is delivered intranasally, orally, subcutaneously, intradermally, intravenously, mucosally, impressed through the skin, or attached to particles delivered to or through the dermis. Alternatively, nucleic acid molecules can be delivered into skin cells by topical application with or without liposomes or charged lipids. Yet another alternative is to deliver the nucleic acid as an inhaled agent. Typically, the nucleic acid molecule is formulated in solutions containing higher quantities of Ca++, e.g., between 1 mM and 2M. The nucleic acid molecule may be formulated with other cations such as zinc, aluminum, and others. Alternatively, or in addition, the nucleic acid molecule may be formulated either with a cationic polymer, cationic liposome-forming compounds, or in non-cationic liposomes. Examples of cationic liposomes for DNA delivery include liposomes generated using 1,2-bis(oleoyloxy)-3-(trimethylammionio) propane (DOTAP) and other such molecules.

A further object of the present invention relates to an aptamer having specificity for a peptide of the present invention, either alone or complexed with HLA molecules that are permissive for peptide binding.

As used herein, the term "aptamer" has its general meaning in the art and refers to a single-stranded oligonucleotide (single-stranded DNA or RNA molecule) that can bind specifically to its target with high affinity. Typically, the method for screening aptamers is based on the so-called SELEX (Systematic Evolution of Ligands by Exponential Enrichment) process as disclosed in U.S. Pat. No. 5,475,096, which is incorporated herein by reference. The SELEX process is known to the one skilled in the art.

In some embodiments, the aptamer of the present invention may comprise deoxyribonucleotide(s), ribonucleotide(s) or combinations thereof. In some embodiments, the aptamer may comprise a single stranded or a double-stranded aptamer. Typically, the aptamers are single stranded aptamers which exhibit defined secondary structures due to the primary sequence and may thus also form tertiary structures. The aptamer according to the invention may have any length provided that it is still able to bind to the target molecule. In some embodiments, the length is between 15 and 120 nucleotides. In some embodiments, the ranges for the length of the aptamer according to the invention are about 20 to 100 nucleotides, about 20 to 80 nucleotides, about 20 to 60 nucleotides, about 20 to 50 nucleotides, for example 30 to 50 nucleotides.

In some embodiments, the aptamer may be modified. Examples for such modifications are described in, among others, Kusser, W. (2000) J Biotechnol, 74: 27-38; Aurup, H. et al (1994) Nucleic Acids Res, 22, 20-4; Cummins, L. L. et al, (1995) Nucleic Acids Res, 23, 2019-24; Eaton, R E. et al (1995) Chem Biol, 2, 633-8; Green, L. S. et al, (1995) Chem Biol, 2, 683-95; Kawasaki, A. M. et al, (1993) J Med Chem, 36, 831-41; Lesnik, E. A. et al, (1993) Biochemistry, 32, 7832-8; Miller, L. E. et al, (1993) J Physiol, 469, 213-43, which are hereby incorporated by reference. In a further embodiment, the aptamer may also comprise nucleotides that have been chemically derivatised with chemical groups. These chemical groups may serve to increase solubility, improve formulation properties, such as stability, increase in vivo stability, such as enzymatic stability, and decrease renal clearance. Derivatisation may be achieved by attachment of a polymer such as PEG or by attachment of a chemical group that has affinity towards a plasma protein, such as e.g. albumin.

A further object of the present invention relates to an antibody having specificity for a peptide of the present invention, either alone or complexed with HLA molecules that are permissive for peptide binding.

As used herein, the term "specificity" refers to the ability of an antibody to detectably bind the peptide of the present invention (i.e. the epitope), while having relatively little detectable reactivity with other epitopes. Specificity can be relatively determined by binding or competitive binding assays, using, e.g., Biacore instruments, as described elsewhere herein. Specificity can be exhibited by, e.g., an about 10:1, about 20:1, about 50:1, about 100:1, 10.000:1 or greater ratio of affinity/avidity in binding to the specific antigen versus nonspecific binding to other irrelevant molecules. The term "affinity", as used herein, means the strength of the binding of an antibody to an epitope. The affinity of an antibody is given by the dissociation constant Kd, defined as [Ab]×[Ag]/[Ab-Ag], where [Ab-Ag] is the molar concentration of the antibody-antigen complex, [Ab] is the molar concentration of the unbound antibody and [Ag] is the molar concentration of the unbound antigen. The affinity constant Ka is defined by 1/Kd. Preferred methods for determining the affinity of mAbs can be found in Harlow, et al., Antibodies: A Laboratory Manual, Cold Spring Harbor Laboratory Press, Cold Spring Harbor, N.Y., 1988), Coligan et al., eds., Current Protocols in Immunology, Greene Publishing Assoc. and Wiley Interscience, N.Y., (1992, 1993), and Muller, Meth. Enzymol. 92:589-601 (1983), which references are entirely incorporated herein by reference. One preferred and standard method well known in the art for determining the affinity of antibodies is the use of Biacore instruments.

In some embodiments, the antibody is a polyclonal antibody or a monoclonal antibody. Monoclonal antibodies may be generated using the method of Kohler and Milstein (Nature, 256:495, 1975). To prepare monoclonal antibodies useful in the invention, a mouse or other appropriate host animal (e.g. mouse, goat, camelid . . . ) is immunized at suitable intervals (e.g., twice-weekly, weekly, twice-monthly or monthly) with the peptide of the present invention. The animal may be administered a final "boost" of the antigenic form within one week of sacrifice. It is often desirable to use an immunologic adjuvant during immunization. Suitable immunologic adjuvants include Freund's complete adjuvant, Freund's incomplete adjuvant, alum, Ribi adjuvant, Hunter's Titermax, saponin adjuvants such as QS21 or Quil A, or CpG-containing immunostimulatory oligonucleotides. Other suitable adjuvants are well-known in the field. The animals may be immunized by subcutaneous, intraperitoneal, intramuscular, intravenous, intranasal or other routes. Following the immunization regimen, lymphocytes are isolated from the spleen, lymph node or other organ of the animal and fused with a suitable myeloma cell line using an agent such as polyethylene glycol to form a hydridoma. Following fusion, cells are placed in media permissive for growth of hybridomas but not the fusion partners using standard methods, as described (Coding, Monoclonal Antibodies: Principles and Practice: Production and Application of Monoclonal Antibodies in Cell Biology, Biochemistry and Immunology, 3rd edition, Academic Press, New York, 1996). Following culture of the hybridomas, cell supernatants are analyzed for the presence of antibodies of the desired specificity, i.e., that selectively bind the antigen. Suitable analytical techniques include ELISA, immunofluorescence, flow cytometry, immunoprecipitation, and Western blotting. Other screening techniques are well-known in the field. Preferred techniques are those that confirm binding of antibodies to conformationally intact, natively folded antigen, such as non-denaturing ELISA, flow cytometry and immunoprecipitation.

In some embodiments, the antibody of the present invention is a chimeric antibody, typically a chimeric mouse/human antibody. The term "chimeric antibody" refers to a monoclonal antibody which comprises a VH domain and a VL domain of an antibody derived from a non-human animal, a CH domain and a CL domain of a human antibody. As the non-human animal, any animal such as mouse, rat, hamster, rabbit or the like can be used. In particular, said mouse/human chimeric antibody may comprise the heavy chain and the light chain of the N41mab antibody.

In some embodiments, the antibody of the present invention is a humanized antibody. As used herein the term "humanized antibody" refers to antibodies in which the framework or "complementarity determining regions" (CDR) have been modified to comprise the CDR from a donor immunoglobulin of different specificity as compared to that of the parent immunoglobulin.

In some embodiments, the antibody of the present invention is a human antibody. Fully human monoclonal antibodies can be prepared by immunizing mice transgenic for large portions of human immunoglobulin heavy and light chain loci. See, e.g., U.S. Pat. Nos. 5,591,669, 5,598,369, 5,545,806, 5,545,807, 6,150,584, and references cited therein, the contents of which are incorporated herein by reference. These animals have been genetically modified such that there is a functional deletion in the production of endogenous (e.g., murine) antibodies. The animals are further modified to contain all or a portion of the human germ-line immunoglobulin gene locus such that immunization of these animals will result in the production of fully human antibodies to the antigen of interest. Following immunization of these mice (e.g., XenoMouse (Abgenix), HuMAb mice (Medarex/GenPharm)), monoclonal antibodies can be prepared according to standard hybridoma technology. These monoclonal antibodies will have human immunoglobulin amino acid sequences and therefore will not provoke human anti-mouse antibody (KAMA) responses when administered to humans. In vitro methods also exist for producing human antibodies. These include phage display technology (U.S. Pat. Nos. 5,565,332 and 5,573,905) and in vitro stimulation of human B cells (U.S. Pat. Nos. 5,229,275 and 5,567,610). The contents of these patents are incorporated herein by reference.

In some embodiments, the antibody of the present invention is selected from the group of Fab, F(ab')2, Fab' and scFv. As used herein, the term "Fab" denotes an antibody fragment having a molecular weight of about 50,000 and antigen binding activity, in which about a half of the N-terminal side of H chain and the entire L chain, among fragments obtained by treating IgG with a protease, papaine, are bound together through a disulfide bond. The term "F(ab')2" refers to an antibody fragment having a molecular weight of about 100,000 and antigen binding activity, which is slightly larger than the Fab bound via a disulfide bond of the hinge region, among fragments obtained by treating IgG with a protease, pepsin. The term "Fab'" refers to an antibody fragment having a molecular weight of about 50,000 and antigen binding activity, which is obtained by cutting a disulfide bond of the hinge region of the F(ab')2. A single chain Fv ("scFv") polypeptide is a covalently linked VH::VL heterodimer which is usually expressed from a gene fusion including VH and VL encoding genes linked by a peptide-encoding linker. The human scFv fragment of the invention includes CDRs that are held in appropriate conformation, preferably by using gene recombination techniques.

The present invention also provides chimeric antigen receptors (CARs) comprising an antigen binding domain of the antibody of the present invention. Typically, said chimeric antigen receptor comprises at least one VH and/or VL sequence of the antibody of the present invention. The chimeric antigen receptor the present invention also comprises an extracellular hinge domain, a transmembrane domain, and an intracellular T cell signaling domain.

As used herein, the term "chimeric antigen receptor" or "CAR" has its general meaning in the art and refers to an artificially constructed hybrid protein or polypeptide containing the antigen binding domains of an antibody (e.g., scFv) linked to T-cell signaling domains. Characteristics of CARs include their ability to redirect T-cell specificity and reactivity toward a selected target in a non-MHC-restricted manner, exploiting the antigen-binding properties of monoclonal antibodies. Moreover, when expressed in T-cells, CARs advantageously do not dimerize with endogenous T cell receptor (TCR) alpha and beta chains.

In some embodiments, the invention provides CARs comprising an antigen-binding domain comprising, consisting of, or consisting essentially of, a single chain variable fragment (scFv) of the antibody of the present invention. In some embodiments, the antigen binding domain comprises a linker peptide. The linker peptide may be positioned between the light chain variable region and the heavy chain variable region.

In some embodiments, the CAR comprises an extracellular hinge domain, a transmembrane domain, and an intracellular T-cell signaling domain selected from the group consisting of CD28, 4-1BB, and CD3ζ intracellular domains. CD28 is a T cell marker important in T cell co-stimulation. 4-1BB transmits a potent costimulatory signal to T cells, promoting differentiation and enhancing long-term survival of T lymphocytes. CD3ζ associates with TCRs to produce a signal and contains immunoreceptor tyrosine-based activation motifs (ITAMs).

In some embodiments, the chimeric antigen receptor of the present invention can be glycosylated, amidated, carboxylated, phosphorylated, esterified, N-acylated, cyclized via, e.g., a disulfide bridge, or converted into an acid addition salt and/or optionally dimerized or polymerized.

A further object of the present invention relates to a TCR having specificity for a peptide of the present invention.

As used herein, the term "T-cell receptor" or "TCR" has its general meaning in the art and refers to the molecule found on the surface of T cells that is responsible for recognizing antigens bound to MHC molecules. During antigen processing, antigens are degraded inside cells and then carried to the cell surface in the form of peptides bound to major histocompatibility complex (MHC) molecules (human leukocyte antigen HLA molecules in humans). T cells are able to recognize these peptide-MHC complexes at the surface of professional APCs or target tissue cells such as β cells in T1DM. There are two different classes of MHC molecules: MHC Class I and MHC Class II that deliver peptides from different cellular compartments to the cell surface that are recognized by CD8+ and CD4+ T cells, respectively. The TCR is the molecule found on the surface of T cells that is responsible for recognizing antigens bound to MHC molecules. The TCR heterodimer consists of an alpha and beta chain in 95% of T cells, whereas 5% of T cells have TCRs consisting of gamma and delta chains. Engagement of the TCR with antigen and MHC results in activation of its T lymphocyte through a series of biochemical events mediated by associated enzymes, co-receptors, and specialized accessory molecules. Each chain of the TCR is a member of the immunoglobulin superfamily and possesses one N-terminal immunoglobulin (Ig)-variable (V) domain, one Ig-constant (C) domain, a transmembrane region, and a short cytoplasmic tail at the C-terminal end. The constant domain of the TCR consists of short connecting sequences in which a cysteine residue forms a disulfide bond, making a link between the two chains. The structure allows the TCR to associate with other molecules like CD3 which possess three distinct chains (γ, δ, and ε) in mammals and the ζ-chain. These accessory molecules have negatively charged transmembrane regions and are vital to propagating the signal from the TCR into the cell. The CD3 chains, together with the TCR, form what is known as the TCR complex. The signal from the TCR complex is enhanced by simultaneous binding of the MHC molecules by a specific co-receptor. On helper T cells, this co-receptor is CD4 (specific for MHC class II); whereas on cytotoxic T cells, this co-receptor is CD8 (specific for MHC class I). The co-receptor not only ensures the specificity of the TCR for an antigen, but also allows prolonged engagement between the antigen presenting cell and the T cell and recruits essential molecules (e.g., LCK) inside the cell involved in the signaling of the activated T lymphocyte. The term "T-cell receptor" is thus used in the conventional sense to mean a molecule capable of recognizing a peptide when presented by an MHC molecule. The molecule may be a heterodimer of two chains α and β (or optionally γ and δ) or it may be a recombinant single chain TCR construct. The variable domain of both the TCR α-chain and β-chain has three hypervariable or complementarity determining regions (CDRs). CDR3 is the main CDR responsible for recognizing processed antigen. Its hypervariability is determined by recombination events that bring together segments from different gene loci carrying several possible alleles. The genes involved are V and J for the TCR α-chain and V, D and J for the TCR β-chain. Further amplifying the diversity of this CDR3 domain, random nucleotide deletions and additions during recombination take place at the junction of V-J for TCR α-chain, thus giving rise to V(N)J sequences; and V-D and D-J for TCR β-chain, thus giving rise to V(N)D(N)J sequences. Thus, the number of possible CDR3 sequences generated is immense and accounts for the wide capability of the whole TCR repertoire to recognize a number of disparate antigens. At the same time, this CDR3 sequence constitutes a specific molecular fingerprint for its corresponding T cell.

The invention also provides a nucleic acid encoding for a chimeric antigen receptor or TCR of the present invention. In some embodiments, the nucleic acid is incorporated in a vector such as those described above.

The present invention also provides a host cell comprising a nucleic acid encoding for a chimeric antigen receptor or TCR of the present invention. While the host cell can be of any cell type, can originate from any type of tissue, and can be of any developmental stage, the host cell is a T cell, e.g. isolated from peripheral blood lymphocytes (PBL) or peripheral blood mononuclear cells (PBMC). The T cell may be derived from a T-cell isolated from a subject. The T-cell may be part of a mixed cell population isolated from the subject, such as a population of PBL or whole unfractionated blood. T cells within the PBL population may be activated by methods known in the art, such as using anti-CD3 and CD28 antibodies or antigen-specific stimulation with peptide-pulsed antigen presenting cells. The T cell may be a CD4+ helper T cell or a CD8+ cytotoxic T cell. The cell may be in a mixed population of CD4+ helper T cells/CD8+ cytotoxic T cells. Polyclonal activation, for example using anti-CD3 antibodies optionally in combination with anti-CD28 antibodies or mitogens such as phytohemagglutinin together with suitable cytokine cocktails will trigger the proliferation of CD4+ and CD8+ T cells, but may also trigger the proliferation of CD4+CD25+ regulatory T cells.

In some embodiments, the T cell is a Treg cell. As used herein, the term 'Treg' or 'T regulatory cell' denotes a T lymphocyte endowed with a given antigen specificity imprinted by the TCR it expresses and with regulatory properties defined by the ability to suppress the response of conventional T lymphocytes or other immune cells. Such responses are known in the art and include, but are not limited to, cytotoxic activity against antigen-presenting target cells and secretion of different cytokines. Different types of Tregs exist and include, but are not limited to: inducible and thymic-derived Tregs, as characterized by different phenotypes such as CD4+CD25+/high, CD4+CD25+/highCD127−/low alone or in combination with additional markers that include, but are not limited to, FoxP3, neuropilin-1 (CD304), glucocorticoid-induced TNFR-related protein (GITR), cytotoxic T-lymphocyte-associated protein 4 (CTLA-4, CD152); T regulatory type 1 cells; T helper 3 cells. All these Tregs can be transformed with the TCR of the present invention, either upon direct ex vivo purification or upon in vitro expansion or differentiation from different precursor cells. Examples of in vitro amplification protocols can be found in Battaglia et al., J. Immunol. 177:8338-8347 (2006), Putnam et al., Diabetes 58:652-662 (2009), Gregori et al., Blood 116:935-944 (2009). While methods for isolating or amplifying suitable numbers of polyclonal Tregs are well known in the art, isolation and/or in vitro expansion of Tregs specific for an antigen of interest such as a β-cell antigen yields more limited cell numbers. Thus, introduction of the desired antigen specificity by transfection or transduction of the CAR or TCR of the present invention into polyclonal Tregs may be envisaged.

A further object of the present invention relates to a method of producing the cell of the present invention, which comprises the step of transfecting or transducing a cell in vitro or ex vivo with a vector encoding for the CAR or TCR of the present invention.

The term "transformation" means the introduction of a "foreign" (i.e. extrinsic or extracellular) gene, DNA or RNA sequence to a host cell, so that the host cell will express the introduced gene or sequence to produce a desired substance, typically a protein coded by the introduced gene or sequence. A host cell that receives and expresses introduced DNA or RNA has been "transformed".

In some embodiments, gene transfer according to present invention into regulatory T cells (Tregs) is desirable as they can induce immune tolerance.

In some embodiments, the cell is isolated from a subject to whom the genetically modified cell is to be adoptively transferred. In some embodiments, a population of cells of the present invention are obtained by isolating a population of T cells from a subject, optionally expanding said population of T cells in a population of regulatory T cells, and by subsequently proceeding with CAR or TCR gene transfer ex vivo and subsequent immunotherapy of the subject by adoptive transfer of the CAR or TCR-transduced cells. Alternatively, the population of cells is isolated from a different subject, such that it is allogeneic. In some embodiments, the population of cells is isolated from a donor subject. Alternatively the population of cells is, or is derived from, a population of stem cells, such as a haemopoietic stem cells (HSC). Gene transfer into HSCs does not lead to CAR or TCR expression at the cell surface, as stem cells do not express the CD3 molecules. However, when stem cells differentiate into lymphoid precursors that migrate to the thymus, the initiation of CD3 expression leads to the surface expression of the introduced CAR or TCR in thymocytes. An advantage of this approach is that the mature T cells, once produced, express only the introduced CAR or TCR and little or no endogenous TCR chains, because the expression of the introduced CAR or TCR chains suppresses rearrangement of endogenous TCR gene segments to form functional TCR alpha and beta genes. A further benefit is that the gene-modified stem cells are a continuous source of mature T cells with the desired antigen specificity. The cell may therefore be a gene-modified stem cell, which, upon differentiation, produces a T-cell expressing a CAR or TCR of the present invention. The present invention also relates to a method of producing a T-cell expressing a CAR or TCR of the present invention by inducing the differentiation of a stem cell which comprises a nucleotide sequence of the present invention.

The population of cells prepared as described above can be utilized in methods and compositions for adoptive immunotherapy in accordance with known techniques, or variations thereof that will be apparent to those skilled in the art based on the instant disclosure. See, e.g., US Patent Application Publication No. 2003/0170238 to Gruenberg et al; see also U.S. Pat. No. 4,690,915 to Rosenberg. In some embodiments, the cells are formulated by first harvesting them from their culture medium, and then washing and concentrating the cells in a medium and container system suitable for administration (a "pharmaceutically acceptable" carrier) in a treatment-effective amount. Suitable infusion medium can be any isotonic medium formulation, typically normal saline, Normosol R (Abbott) or Plasma-Lyte A (Baxter), but also 5% dextrose in water or Ringer's lactate can be utilized. The infusion medium can be supplemented with human serum albumin. A treatment-effective amount of cells in the composition is dependent on the relative representation of the T cells with the desired specificity, on the age and weight of the recipient, on the severity of the targeted condition and on the immunogenicity of the targeted antigens. These amounts of cells can be as low as approximately $10^3$/kg, preferably $5 \times 10^3$/kg; and as high as $10^7$/kg, preferably $10^8$/kg. The number of cells will depend upon the ultimate use for which the composition is intended, as will the type of cells included therein. For example, if cells that are specific for a particular antigen are desired, then the population will contain greater than 70%, generally greater than 80%, 85% and 90-95% of such cells. The desired purity can be achieved by introducing a sorting step following introduction of the desired TCR sequence using methods such as HLA multimers and others known in the art. For uses provided herein, the cells are generally in a volume of a liter or less, can be 500 ml or less, even 250 ml or 100 ml or less. The clinically relevant number of immune cells can be apportioned into multiple infusions that cumulatively equal or exceed the desired total amount of cells.

The cells of the present invention, in particular regulatory T cells or stem cells, are thus particularly suitable for the treatment of T1DM. According, a further object of the present invention relates to a method of treating T1DM in a subject in need thereof, comprising administering to the subject a therapeutically effective amount of a population of cells of the present invention.

A further object of the present invention relates to MHC class I or class II multimer loaded with a peptide of the present invention.

Typically MHC class I or class II multimers are well known in the art and include but are not limited to dimers, tetramers, pentamers, streptamers, dextramers and octamers. As used herein, the term "Major Histocompatibility Complex" (MHC) is a generic designation meant to encompass the histo-compatibility antigen systems described in different species including the human leucocyte antigens (HLA). As used herein, the term "MHC/peptide multimer" refers to a stable multimeric complex composed of MHC protein subunits loaded with a peptide of the invention. According to the invention, said MHC/peptide multimer (also called herein MHC/peptide complex) include, but are not limited to, a MHC/peptide dimer, trimer, tetramer, pentamer or higher valency multimer. In humans there are three major different genetic loci that encode MHC class I molecules (the MHC molecules of the human are also designated human leukocyte antigens (HLA)): HLA-A, HLA-B, and HLA-C. HLA-A*01, HLA-A*02, and HLA-A*11 are examples of different MHC class I alleles that can be expressed from these loci. It should be further noted that non-classical human MHC class I molecules such as HLA-E (the functional homolog in mice is called Qa-1b) and MICA/B molecules are also encompassed within the context of the invention. In some embodiments, the MHC/peptide multimer is a HLA/peptide multimer selected from the group consisting of HLA-A/peptide multimer, HLA-B/peptide multimer, HLA-C/peptide multimer, HLA-E/peptide multimer, MICA/peptide multimer and MICB/peptide multimer. In humans there are three major different genetic loci that encode MHC class II molecules: HLA-DR, HLA-DP, and HLA-DQ, each formed of two polypeptides, α and β chains (A and B genes). HLA-DQA1*01, HLA-DRB1*01, and HLA-DRB1*03 are examples of different MHC class II alleles that can be expressed from these loci. It should be further noted that non-classical human MHC class II molecules such as HLA-DM and HL-DOA (the functional homolog in mice is called H2-DM and H2-O) are also encompassed within the context of the invention. In some embodiments, the MHC/peptide multimer is a HLA/peptide multimer selected from the group consisting of HLA-DP/peptide multimer, HLA-DQ/peptide multimer, HLA-DR/peptide multimer, HLA-DM/peptide multimer and HLA-DO/peptide multimer. Methods for obtaining MHC/peptide multimers are described in WO96/26962 and WO01/18053, which are incorporated by reference. The MHC/peptide multimer may be a multimer where the heavy chain of the MHC is biotinylated, which allows combination as a tetramer with streptavidine. Such MHC-peptide tetramer has an increased avidity for the appropriate TCR-carrier T lymphocytes and can therefore be used to visualize reactive populations by immunofluorescence. The multimers can also be attached to paramagnetic particles or magnetic beads to facilitate removal of non-specifically bound reporter and cell sorting. Such particles are readily available from commercial sources (e.g. Beckman Coulter, Inc., San Diego, Calif., USA). Multimer staining does not kill the labelled cells; therefore cell integrity is maintained for further analysis. In some embodiments, the MHC/peptide multimer of the present invention is particularly suitable for isolating or identifying a population of CD8+ T cells having specificity for the peptide of the present invention (in a flow cytometry assay).

The peptides or MHC class I or class II multimer as described herein is particularly suitable for detecting autoreactive T cells specific for a peptide of the present invention. Therefore the peptide or the multimer of the present invention is particularly suitable for diagnosing T1DM or predicting the risk of T1DM in a subject. In some embodiments, the diagnostic method of the present invention is performed as described in WO 2010119307. In some embodiments, the method comprises the steps consisting of culturing a blood or PBMC sample obtained from the subject in an appropriate culture medium which comprises an amount of Granulocyte/Macrophage Colony-Stimulating Factor (GM-CSF) and/or IL-4 and/or FMS-like tyrosine kinase 3 (Flt-3) ligand and/or IL-1beta and an amount of a least peptide of the present invention and detecting at least one T cell displaying a specificity for the peptide. Methods for the detection of stimulated T cells are known to the skilled person (e.g. Enzyme-linked immunospot (ELISpot), proliferation assay, supernatant cytokine assay . . . ). Alternatively, the diagnostic method of the present invention involves the use of a peptide of the present invention that is loaded on multimers as described above, so that the isolated CD8+ T cells from the subject are bringing into contact with said multimers. There is no requirement for in vitro T cell activation or expansion. Following binding, and washing of the T cells to remove unbound or non-specifically bound multimer, the number of CD8+ cells binding specifically to the HLA-peptide multimer may be quantified by standard flow cytometry methods, such as, for example, using a FACS LSR Fortessa flow cytometer (Becton Dickinson). The multimers can also be attached to paramagnetic particles or magnetic beads to facilitate removal of non-specifically bound reporter and cell sorting. Such particles are readily available from commercial sources (eg. Beckman Coulter, Inc., San Diego, Calif., USA).

The peptides or MHC class I or class II multimer as described herein can also be used as therapeutic agents to induce immune tolerance. Therefore the peptide or the multimer of the present invention are suitable for treating or preventing T1DM in a subject. Said MHC class I or class II multimers can be administered in soluble form or loaded on nanoparticles, e.g. as described by Clemente-Casares et al. Nature 530:434-40 (2016).

A further object of the present invention relates to assays that may be developed to detect autoantibodies directed against a peptide of the present invention. These assays are well-known to those skilled in the art and can be obtained by techniques such as radioimmunoassays and enzyme-linked immunosorbent assays. These assays can be used to diagnose T1DM in a subject or to stratify the risk of developing T1DM in a subject, as exemplified by current autoantibody assays developed for insulin, GAD, IA-2 and ZnT8.

The invention will be further illustrated by the following figures and examples. However, these examples and figures should not be interpreted in any way as limiting the scope of the present invention.

Example 1: Conventional and Neo-Antigenic Peptides Presented by Beta Cells are Targeted by Circulating Naïve CD8+ T Cells in Type 1 Diabetic and Healthy Donors Methods Cell Lines The ECN90 cell line (HLA-A*02:01/03:01, -B*40:01/49:01, -C*03:04/07:01) was derived from a human neonatal pancreas using described protocols (Ravassard et al., 2011). Cells were seeded in 15-cm diameter tissue culture dishes (Techno Plastic Products AG) coated with 0.1% fibronectin solution from human plasma (Sigma; 400 ng/cm$^2$) and extracellular matrix from Engelbreth-Holm-Swarm murine sarcoma (Sigma; 1-2.4 mg/cm$^2$). They were maintained in DMEM/F12 medium supplemented with 2% bovine serum albumin, 6.7 ng/ml sodium selenite, 10 mM nicotinamide, 50 µM β-mercaptoethanol and penicillin/streptomycin. IFN-γ (R&D) was added to the cell culture at 80-90% confluence at a final concentration of 500 U/ml for 16-18 h. IFN-γ, TNF-α and IL-1β were added at a final concentration of 2,000 U/ml, 1,100 U/ml, and 1,000 U/ml, respectively.

Primary Human Tissues and PBMCs

For HLA peptidomics experiments, transplantation-grade, undispersed primary human islets (75% purity; HLA-A*02:01/25:01, -B*39:01/51:01, -C*12:03/14:02) were obtained from a brain-dead non-diabetic organ donor (age 49 years, male, BMI 37 kg/m$^2$; protocol approved by the Agence de la Biomédecine) with standard procedures and maintained in CMRL 1066 medium (Sigma) supplemented with 10% fetal bovine serum. For RNAseq analyses, primary human islets from 5 brain-dead non-diabetic organ donors (mean age 50.6±10.2 years, 3 females, 2 males, BMI 25±2 kg/m$^2$; 57±5% β cells; protocol approved by the Ethics Committee of the University of Pisa, Italy) were exposed or not to IFN-γ (1,000 U/ml) and IL-1β (50 U/ml) for 48 h. Primary human HLA Class II$^{lo}$ and Class II$^{hi}$ mTECs were purified as described (Pinto et al., 2014) from the thymi of 3 children (male gender, age 6 days, 4 months and 9 months) undergoing corrective cardiac surgery at the University of Heidelberg, Germany (Ethics approval 367/2002). Cryopreserved PBMCs from T1D and healthy donors (data not shown) were collected under the Ethics approval DC-2015-2536 Ile-de-France I. Informed consent was obtained from all subjects, or next-of-kin for islet donors.

Purification of pHLA Class I Complexes

W6/32 and HC10 anti-HLA Class I mAbs were purified on a protein A Prosep Ultraplus column (Millipore) from hybridoma supernatants. The W6/32 mAb recognizes a conformational epitope formed by the interaction of the HLA Class I heavy chain and β2-microglobulin and was used for purifying pHLA Class I complexes. The HC10 mAb recognizes a linear epitope on the HLA Class I heavy chain and was used for Western blotting.

The HLA class I peptidome of the ECN90 β-cell line was obtained from 5 biological replicates. A single biological replicate was available for primary human islets. Frozen cell pellets (~20×10$^6$/condition for ECN90 cells; ~25,000 islet equivalents/condition for primary islets, corresponding to ~19×10$^6$ (3 cells) were resuspended in a buffer containing 10 mM Tris-HCl pH 8.0, 150 mM NaCl, 5 mM EDTA, 0.1% (v/v) Complete Protease Inhibitor Cocktail (Roche), and 1% (w/v) octyl-β-D glucopyranoside (Sigma). Lysis was carried out at 4° C. for 1 h under rotation, with two sonication steps at 30 and 60 min. Lysates were cleared by centrifugation and pHLA complexes immunoaffinity-purified with the W6/32 mAb covalently bound to Protein A Sepharose CL-4B beads (GE Healthcare) by dimethyl pimelidate cross-linking. Beads were subsequently loaded on GELoader Tips (20 μl; ThermoFisher) and washed before elution of pHLA complexes with 10% acetic acid. Aliquots were collected at each washing and elution step for analysis by 12% SDS-PAGE and Western blot using the HC10 mAb to verify the yield and purity of the eluted HLA Class I.

Eluted peptides and the associated HLA Class I heavy chain and β2-microglobulin obtained from 20×10$^6$ cells were concentrated to 20 μl by vacuum centrifugation, acidified with 10 μl of 1% aqueous formic acid (Normapur) and loaded on C18 stage tips (ThermoFisher) prewashed with 100% methanol and equilibrated with acetonitrile (ACN)/ 0.1% formic acid in LC-MS grade water (aq. formic acid) 2:98 (v/v). After loading, the C18 stage tips were washed with ACN/0.1% aq. formic acid 2:98 (v/v) and peptides separated from the more hydrophobic HLA Class I heavy chain and β2-microglobulin species by eluting them with ACN/0.1% aq. formic acid 1:1 (v/v). The ACN was evaporated by vacuum centrifugation and the peptides resuspended up to 6 μl of volume in a solution of ACN/0.1% aq. formic acid 2:98 (v/v) and spiked with 10 fmol/μl of a cytomegalovirus pp65 495-503 peptide (NLVPMVATV) as internal control. For MS analysis, 5 μl of this peptide solution were used.

LC-MS/MS Peptides were loaded and separated by nano-flow HPLC (RSLC Ultimate 3000, ThermoFisher Scientific) on a reversed phase nanocolumn (C18 Acclaim PepMap 100, 50 cm length, 75 μm i.d. ThermoFisher Scientific) coupled on-line to a nanoESI Q Exactive mass spectrometer (ThermoFisher Scientific). Peptides were eluted with a linear gradient of 2-50% buffer B (ACN, 0.05% aq. formic acid 80:20 v/v) at a flow rate of 220 nl/min over 60 min at 35° C. Data was acquired using a data-dependent "top 10" method, which isolated and fragmented peptides by higher energy collisional dissociation: one survey full scan MS spectra at a resolution of 70,000 at 200 m/z with a AGC target value of 3×106 ions was followed by ten MS/MS spectra at a resolution of 17,500 at 200 m/z, on the 10 most intense ions, sequentially isolated and accumulated with a AGC target value of 1×105 and a maximum injection time of 120 ms. Ions with unassigned charge states or charge states ≥4 were not considered. The peptide match option was disabled. Fragmented m/z species were dynamically excluded from further selection for 20 s. The resulting spectra were analyzed by MaxQuant using a custom database comprising: a) the reference human proteome (Swiss-Prot/UniProt, up000005640, release Dec 2012); b) an in-house database containing 119,305 predicted peptide splice products (Berkers et al., 2015) from major known and candidate β-cell protein Ags (data not shown); and c) the predicted amino acids neo-sequences encoded by mRNA splice variants identified by RNASeq. The following parameters were set: enzyme specificity: unspecific; variable modifications: methionine, tryptophan and histidine oxidation (+15.99 Da), cysteine oxidation to cysteic acid (+47.98 Da) and tryptophan conversion to kynurenine (+3.99 Da); false discovery rate of peptides: 0.05. Since the MS identification was targeted on HLA Class I-eluted peptides rather than on proteins, the protein false discovery rate parameter was set to 100%. The initial allowed mass deviation of the precursor ion was set to 10 ppm and the maximum fragment mass deviation was set to 20 mDa. The "match between runs" option was enabled to match identifications across different replicates in a time window of 0.5 min and an initial alignment time window of 20 min. For conventional peptides, source proteins were selected based on: a) a non-ubiquitous expression pattern, based on the Human Protein Atlas (www.proteinatlas.org) (Uhlen et al., 2015); b) a pancreas- and β-cell-enriched expression pattern, based on the Human Protein Atlas, the Human Protein Reference Database (www.hprd.org) (Keshava Prasad et al., 2009) and the Single-Cell Gene Expression Atlas of Human Pancreatic Islets (http://sandberg.cmb.ki.se/pancreas) (Segerstolpe et al., 2016). For all peptides, the final filter was based on an enrichment in HLA-eluted samples compared with mock-eluted ones based on m/z peak intensity, which verified the specific association of the identified peptides with pHLA complexes.

RNAseq Analysis

RNAs from primary human islets exposed or not to IFN-γ (1,000 U/ml) and IL-1β (50 U/ml) for 48 h and from immature and mature human mTECs were sequenced on an Illumina HiSeq 2000 at high depth (coverage >150×10$^6$ reads). mRNA isoforms were selected based on median RPKM values: a) >5 in islets (either in basal or inflammatory conditions), a cut-off selected based on the median RPKM of known islet Ags; b) <0.1 in mTECs (either HLA Class II$^{lo}$ or Class II$^{hi}$) or with a fold-change >100 vs. islet RPKM; c) a fold-change >10 in islets compared to 12 control tissues (adipose tissue, breast, colon, heart, kidney, liver, lung, lymph node, ovary, prostate, skeletal muscle, white blood cells; the Illumina BodyMap 2.0 dataset, GEO accession number GSE30611), i.e. selecting isoforms that are enriched in islets. Tissues of neuroendocrine origin (brain, testis, adrenal gland and thyroid) were excluded for this filtering. We subsequently focused our analysis on mRNA isoforms, as described (Cnop et al., 2014; Eizirik et al., 2012; Villate et al., 2014). The predicted translation products were aligned using MUSCLE 3.8 (www.ebi.ac.uk/Tools/msa/muscle), and amino acids neo-sequences were defined by comparing the predicted aa sequence of each mRNA isoform with that of the reference mRNA, taking as reference the longest and/or most prevalent mRNA isoform in islets. The neo-sequences thus identified were used to interrogate HLA peptidomics datasets and searched in parallel for potential HLA-A2 binders based on their predicted HLA-A2 binding affinity ($K_D$<100 nM by NetMHC 4.0; www.cbs.dtu.dk/services/NetMHC) (Andreatta and Nielsen, 2016), stability (half-life ≥1.5 h by NetMHC Stab 1.0; www.cbs.dtu.dk/services/NetMHCstab-1.0) (Jorgensen et al., 2014), 9-10 aa length and ≥3 aa neo-sequences.

HLA-A2 MMr Assays

All peptides were synthesized at >90% purity (Synpeptides). HLA-A2 MMrs were produced as described (Leisner et al., 2008) and staining performed in the presence of 50 nM dasatinib (Lissina et al., 2009), as described (Culina et al., 2018). Briefly, cryopreserved PBMCs were magnetically depleted of CD8⁻ cells (StemCell Technologies), stained with the combinatorial MMr panels (Hadrup et al., 2009) and acquired using a FACSAria III cytometer.

In-Situ HLA-A2 MMr Staining on Pancreas Sections.

In-situ staining was performed as described (Culina et al., 2018). Unfixed, frozen sections were dried for 2 h, loaded with 1 μg of MMrs overnight at 4° C., washed gently with phosphate-buffered saline and fixed in 2% paraformaldehyde for 10 min. After a further wash, endogenous peroxidase activity was blocked with 0.3% $H_2O_2$. Sections were then incubated serially with rabbit anti-phycoerythrin, horseradish peroxidase-conjugated swine anti-rabbit and 3,3'-diaminobenzidine tetrahydrochloride substrate (ThermoFisher). After a final wash, sections were counterstained with hematoxylin, dehydrated via sequential passages in 95-100% ethanol and xylene, mounted and analyzed using a Nikon Eclipse Ni microscope with NIS-Elements Analysis D software v4.40.

Quantification and Statistical Analysis

Statistical details of experiments can be found in the legends of each figure. A two-tailed $p<0.05$ cut-off was used to define statistical significance.

Results

The HLA Class I peptidome of human β cells is enriched by cytokine exposure and displays the expected amino-acid length and motifs.

Our first epitope discovery pipeline employed HLA peptidomics experiments on the ECN90 β-cell line (Culina et al., 2018), which carries the HLA Class I haplotype A*02:01/A*03:01/B*40:01/B*49:01/C*03:04/C*07:01 (subsequently referred to as A2/A3/B40/B49/C3/C7). ECN90 0 cells were cultured overnight with or without interferon (IFN)-γ, alone or in combination with tumor necrosis factor (TNF)-α and interleukin (IL)-1β, and lysed to immunopurify pHLA complexes. HLA-bound peptides were then dissociated and run on a liquid chromatography-tandem mass spectrometry (LC-MS/MS) system. Although ECN90 β cells expressed surface HLA Class I under basal conditions, this expression was significantly upregulated upon cytokine treatment (data not shown), without inducing significant cell death (Culina et al., 2018). The 2,997 eluted peptides were mostly (93%) 8-12-mers (data not shown), thus featuring the expected amino acid (aa) length required for HLA Class I binding. The amino acids identities at pHLA anchor position also revealed the preferences expected based on the HLA Class I haplotype of the β cells used (data not shown). In line with the observed HLA Class I upregulation, the number of eluted peptides was significantly higher in the presence of cytokines, and higher in β cells exposed to IFN-γ, TNF-α and IL-1β compared with IFN-γ alone (data not shown).

These peptide datasets were subsequently analyzed using a bioinformatics pipeline comprising several sequential filters (data not shown). First, only peptides that were reproducibly detected in at least 2 of 5 biological replicates (85%; all percentages are given in relation to the number of peptides retained by the previous filter) and that displayed the expected 8-12-aa length (93%) were selected. β-cell-enriched peptides (both conventional and with PTMs, excluding those derived from peptide or mRNA splicing) were subsequently filtered based on an expression of their source proteins reported to be non-ubiquitous (16%) and enriched in β cells (34%). For other non-conventional peptides (i.e. PTM or transcriptional variants), no expression filter was applied, as these species could potentially be β-cell-specific in spite of a ubiquitous expression of the source protein or mRNA. PTM peptides (methionine, tryptophan, histidine and cysteine oxidation and tryptophan conversion to kynurenine) derived from ubiquitous proteins accounted for 8% of the whole dataset. MS species potentially corresponding to peptide splice variants (0.5%) were identified using an in-house script (data not shown) that employed reported peptide splicing preference rules (Berkers et al., 2015) applied to known Ags or to putative ones identified herein.

For peptides derived from mRNA splice variants, the HLA peptidomics dataset was interrogated against RNAseq datasets obtained from primary human islets exposed or not to cytokines and from human mTECs (data not shown). We first reasoned that higher gene expression levels are more likely to result in significant peptide processing and presentation. Hence, mRNA splice variants were selected based on a median Reads Per Kilobase per Million mapped reads (RPKM)>5 in islets (either with or without inflammatory stimulation; 27%), a cut-off based on the median RPKM of known islet Ags (Eizirik et al., 2012). Second, we reasoned that mRNA iso forms that are poorly expressed in mTECs may be more likely to result in T-cell escape from clonal deletion. Thus, only mRNA variants with a RPKM<0.1 in mTECs or with a fold-increase >100 in islets vs. mTECs were selected (6%). Third, we selected mRNA isoforms with >10-fold higher expression in islets compared to other tissues. We then analyzed the predicted aa neo-sequences encoded by these mRNA variants, yielding 88/166 mRNA variants (53%) and 336 peptide neo-sequences that were used to interrogate the HLA peptidomics dataset, with 2 hits found. In all instances, one last filter verified that the peptides identified were enriched in HLA-purified samples compared with mock immunoprecipitation, leading to the overall exclusion of 48% peptides.

Collectively, these results show that inflammatory cytokines increase pHLA presentation and that the peptides identified display the aa signatures required for HLA binding.

pHLA complexes of human β cells are enriched in peptides derived from secretory granule proteins, including known PPI epitopes.

While 42/98 (43%) eluted peptides were shared among basal and cytokine-treated conditions and 34/98 (35%) peptides were shared between the two cytokine-treated conditions, 45/98 (46%) peptides were only detected upon cytokine exposure, with only 2 (2%), 3 (3%) and 8 (8%) peptides specifically detected under basal, IFN-γ- and IFN-γ/TNF-α/IL-1β-treated conditions, respectively (data not shown). Among the 40 source proteins of HLA Class I-eluted peptides (data not shown), the most represented ones were two well-known Ags, namely CHGA (n=15 peptides) and PPI (n=12, plus one derived from an INS-006 mRNA splice variants). Besides the other known islet Ag IA-2 (PTPRN; n=3), the 5 top scoring proteins included two novel putative Ags, namely Kinesin Family Member 1A (KIF1A; n=9) and SCG5 (also known as 7B2; n=3, plus one derived from a SCG5-009 mRNA splice variant). Other proteins included known islet Ags, i.e. GAD2 (GAD65) and SLC30A8 (ZnT8) and several putative ones. Notably, all the HLA-A2-restricted PPI peptides identified, namely $PPI_{2-10}$, $PPI_{6-14}$, $PPI_{15-24}$ (and a $PPI_{15-26}$ length variant), $PPI_{29-38}$ ($PI_{B5-14}$) and $PPI_{34-42}$ ($INS_{B10-18}$) (data not shown), are already described as major CD8⁺ T-cell epitopes, thus validating our discovery strategy. The overall set of source proteins was enriched for insulin granule products (12/40, 30%; data not shown), namely CHGA, INS, SCG5, PTPRN (IA-2), ATP-binding cassette sub-family C member 8 (ABCC8), proprotein convertase 1 (PCSK1/PC1), urocortin-3 (UCN3), chromogranin B (CHGB), carboxypeptidase E (CPE), proprotein convertase 2 (PCSK2/PC2), secretogranin III (SCG3) and SLC30A8 (Suckale and Solimena, 2010). The predicted HLA Class I restrictions of the peptides identified (data not shown) comprised all the alleles expressed by ECN90 0 cells, namely HLA-A2 (32%), -A3 (22%), -B40 (20%), -B49 (3%), -C3 (11%) and -C7 (3%), while 10% of restrictions could not be assigned. Most peptides (67/98; 68%) retained after bioinformatics analysis were found to be exclusively or more presented in cytokine-treated ECN90 0 cells (data not shown). Only 15/98 (15%) peptides were similarly presented in all conditions and 3/98 (3%) peptides exclusively or more presented under basal conditions. For peptides derived from β-cell-enriched proteins, 11/98 (11%) carried PTMs, with most of them (8/11; 73%) representing variants of unmodified peptides identified in this same dataset. Most of these modifications (7/11; 64%) were M(+15.99) methionine oxidations, C(+47.98) cysteine and W(+15.99) tryptophan oxidations, but W(+3.99) tryptophan to kynurenine transitions were also detected.

To validate the results obtained using the ECN90 β-cell line, a similar HLA peptidomics analysis was applied to a preparation of HLA-A2$^+$ primary human islets that did not share other HLA Class I alleles with ECN90 cells. The major source proteins of the HLA-bound peptides identified were largely overlapping with those found in ECN90 cells (data not shown), with INS (n=12 peptides), CHGA (n=4), KIF1A (n=3) and SCG5 (n=3) ranking highest for both cells and CHGB (n=3) and PCSK2 (n=1) also detected in both. When analyzing the identity of individual peptides (including length variants) (data not shown), 16/33 (48%) were shared between ECN90 and primary islet cells. This common repertoire increased to 12/13 (92%) peptides when only those predicted to bind the HLA-A2 molecule shared between ECN90 and primary islet cells were considered, lending support to the validity of the ECN90 β-cell model. Of note, shared peptides included all the PPI species already described as CD8$^+$ T-cell epitopes, the SCG5186-196 peptide along with a shorter SCG5186-195 length variant with higher HLA-A2 affinity and a peptide splice variant possibly derived from the fusion of $IAPP_{15-17}/IAPP_{5-10}$. Although this product could also result from $PTPRN_{596-598}/IAPP_{5-10}$ trans-splicing, the former possibility is more likely because the intra-protein vicinity of the $IAPP_{15-17}$ and $IAPP_{5-10}$ sequences is more favorable for transpeptidation. The new hits identified were mostly predicted to bind to the HLA Class I molecules not shared with ECN90 cells, barring a HLA-A2-restricted $CHGB_{440-448}$ peptide that was retained for further validation. Contrary to ECN90 cells, most peptides were detected at similar levels in the basal and cytokine-treated condition, possibly reflecting a higher sensitivity to cytokine-induced apoptosis of primary human islets or the isolation of some pHLA complexes from non-β cells. Indeed, several pancreatic polypeptide- and glucagon-derived species, most likely eluted from δ and α cells (n=4 and 5, respectively), were also detected (not shown since they were excluded by the filter of β-cell-enriched expression).

The sequence of the identified peptides was confirmed by comparing their MS/MS spectra with those of the corresponding synthetic peptides. Finally, the predicted HLA-A2 binding was experimentally verified (data not shown), leading to the final selection of 18/19 (95%) HLA-eluted peptides for CD8$^+$ T-cell studies.

Collectively, these data show that several known HLA-A2-restricted PPI epitopes are naturally processed and presented by β cells and identify novel candidate β-cell epitopes, several of which are derived from secretory granule proteins.

In silico analysis of mRNA splice variants yields additional predicted neo-Ag peptides.

The RNAseq dataset used for assigning m/z species was further mined in silico, independently of the HLA peptidomics pipeline, to identify other potential HLA Class I-restricted peptides (data not shown). The selection criteria applied were a predicted HLA-A2 binding, a 9-10 aa length and a neo-sequence stretch ≥3 aa. Thirty-nine candidates were thus selected (data not shown), which were splice variants of either known β-cell Ags (GAD2-003, IAPP-002, IAPP-004, PTPRN-021, SLC30A8-002) or candidate ones. Most of the source mRNA splice variants (36/39, 92%) were similarly expressed in untreated and cytokine-treated islets. HLA-A2 binding was experimentally confirmed for 34/39 (87%) of these predicted peptides (data not shown), which were retained for further validation along with the 18 HLA-A2 binders identified in the HLA peptidomics pipeline.

HLA-A2-restricted β-cell peptides are targeted by a circulating naïve CD8$^+$ T-cell repertoire in healthy donors.

Our previous work documented that the great majority of individuals, both type 1 diabetic and healthy, harbor similar frequencies of circulating, predominantly naïve HLA-A2-restricted CD8$^+$ T cells reactive to known PPI, GAD65, IA-2, IGRP and ZnT8 epitopes (Culina et al., 2018). Notwithstanding the possibility that the candidate epitopes here identified may be preferentially recognized in T1D patients, the preliminary requirement for the priming of their cognate CD8$^+$ T cells during the autoimmune process is the presence of a naïve repertoire capable of recognizing them. We therefore started by verifying if the HLA-A2-restricted candidate epitopes identified in the in vitro HLA peptidomics and in silico transcriptomics pipeline (n=52; 18 and 34, respectively) were recognized by circulating CD8$^+$ T cells in HLA-A2$^+$ healthy donors (data not shown), using combinatorial HLA-A2 multimers (MMrs) loaded with the corresponding synthetic peptides as a readout (Culina et al., 2018). We considered these candidates as harboring a cognate naïve CD8$^+$ T-cell repertoire based on i) the frequency of such naïve repertoire, which is typically in the range of 1-50/10$^6$ CD8$^+$ T cells (Alanio et al., 2010; Culina et al., 2018; Yu et al., 2015); and ii) the pattern of HLA MMr staining, which is usually clustered rather than spread in the presence of a specific epitope-reactive population (James et al., 2017). Using these two criteria, several candidate epitopes displayed a cognate naïve CD8$^+$ T-cell repertoire in the expected range in a sizable fraction (≥50%) of the healthy individuals analyzed. The frequency of CD8$^+$ T cells recognizing the known β-cell epitope $PPI_{6-14}$ previously analyzed (Culina et al., 2018) also fell in the same range, with some outliers noted. In total, 9/18 (50%) of HLA-eluted peptides (data not shown) were validated, namely $CHGA_{344-352}$, insulin gene enhancer protein $ISL1_{276-284}$, $KCNK16_{129-137}$, $KIF1A_{1347-1355}$, $PCSK2_{30-38}$, $SCG5_{186-195}$, $SCG5$-$009_{186-194}$ and $UCN3_{1-9}$. Despite recognition in only 1 of 6 donors analyzed, the peptide splice product $IAPP_{15-17}/IAPP_{5-10}$ was also retained, since it was identified in the HLA peptidomics datasets of both ECN90 and primary islet cells. Using the same criteria, 11/34 (32%) candidates selected in silico were validated (data not shown), namely cyclin I (CCNI)-008$_{14\text{-}22}$, GAD2-003$_{179\text{-}187}$, guanine nucleotide-binding protein G(s) subunit a isoforms short (GNAS)-036$_{67\text{-}75}$, GNAS-036$_{124\text{-}132}$, IAPP-002$_{33\text{-}42}$, PTPRN-021$_{392\text{-}402}$, PTPRN-021$_{398\text{-}407}$, phogrin/receptor-type tyrosine-protein phosphatase N2 (PTPRN2)-005$_{11\text{-}19}$, PTPRN2-005$_{19\text{-}27}$, mitochondrial oligoribonuclease (REXO2)-020$_{2\text{-}10}$, and SLC30A8-002$_{16\text{-}25}$. As previously observed for other known β-cell epitopes (Culina et al., 2018), including the PPI$_{6\text{-}14}$ here used as β-cell positive control, only a minority (median 16.4%, interquartile range 8.5-26.7%) of CD8$^+$ T cells recognizing these candidate epitopes were Ag-experienced (CD45RA$^+$CCR7$^-$, CD45RA$^-$ CCR7$^-$ or CD45RA$^-$CCR7$^+$; data not shown). Conversely, the Flu MP$_{58\text{-}66}$ peptide included as viral positive control displayed the expected predominantly Ag-experienced phenotype. All the peptides validated came from source proteins whose gene expression was detected in islets, both under basal and cytokine-treated conditions. One notable exception was SCG5-009, whose expression was negligible under basal condition but strongly upregulated following cytokine treatment. Gene expression in mTECs was also negligible in all cases, with the exception of CHGA, ISL1 and SCG5.

Collectively, these results show that most of the β-cell peptides identified display a cognate naïve CD8$^+$ T-cell repertoire in the blood of healthy individuals, thus making them potential targets of islet autoimmunity.

Circulating CD8$^+$ T cells reactive to HLA-A2-restricted β-cell peptides display similar ex-vivo frequencies and a predominantly naïve phenotype in T1D and healthy subjects.

Thirteen of the 20 β-cell peptides validated for recognition by a naïve CD8$^+$ T-cell repertoire were selected for further ex-vivo combinatorial MMr analyses using blood samples from HLA-A2$^+$ recent-onset T1D and healthy subjects (n=10/each; data not shown). For naturally processed and presented peptides identified by HLA peptidomics, we focused our selection on 6 putative Ags localized in insulin granules, namely IAPP$_{15\text{-}17/5\text{-}10}$, PCSK2$_{30\text{-}38}$, SCG5$_{186\text{-}195}$, SCG5-009$_{186\text{-}194}$ and UCN3$_{1\text{-}9}$, with the addition of the transcription factor ISL1$_{276\text{-}284}$. A more balanced selection was made for 7 predicted mRNA splice peptides, as these may be derived from short-lived, unstable defective ribosomal products (DRiPs) (Anton and Yewdell, 2014). CCNI-008$_{14\text{-}22}$, GAD2-003$_{179\text{-}187}$, GNAS-036$_{67\text{-}75}$, GNAS-036$_{124\text{-}132}$, IAPP-002$_{33\text{-}42}$, PTPRN2-005$_{11\text{-}19}$ and SLC30A8-002$_{16\text{-}25}$ were thus selected. The frequency of circulating CD8$^+$ T cells recognizing these peptides and the control PPI$_{6\text{-}14}$ epitope was similar in T1D and healthy subjects (data not shown), and fell in the same range (1-50/10$^6$ CD8$^+$ T cells) detected in the preliminary screening performed on healthy subjects using different fluorochrome-labeled MMr combinations (data not shown), with the exception of IAPP-002$_{33\text{-}42}$ for which virtually no MMr$^+$ cells were detected, possibly representing a technical failure. As in the screening round, frequencies were particularly high and clustered for 4 CD8$^+$ T-cell specificities, namely SCG5-009$_{186\text{-}194}$, UCN3$_{1\text{-}9}$, CCNI-008$_{14\text{-}22}$ and GAD2-003$_{179\text{-}187}$. As previously reported for PPI$_{6\text{-}14}$ and other known β-cell epitopes (Culina et al., 2018), these MMr$^+$ cells displayed a predominantly naïve phenotype in both T1D and healthy subjects (data not shown; median 8.3%, interquartile range 0-20%).

Collectively, these results show that the β-cell peptides identified are targeted by similar frequencies of predominantly naïve circulating CD8$^+$ T cells in both T1D and healthy subjects.

Pancreas-infiltrating cells of T1D patients recognize the HLA-A2-restricted IAPP$_{15\text{-}17/5\text{-}10}$ and ISL1$_{276\text{-}284}$ peptides.

Given the lack of difference in frequency or markers of prior Ag encounter observed for circulating islet-reactive CD8$^+$ T cells between T1D and healthy donors, we verified whether these reactivities were present in the pancreas-infiltrating cells of HLA-A2$^+$ T1D patients by in-situ MMr staining of tissue sections from the Network for Pancreatic Organ Donors (nPOD) repository. To this end, we selected two peptides, namely IAPP$_{15\text{-}17/5\text{-}10}$ and ISL1$_{276\text{-}284}$, representative of the low-medium frequency range detected in peripheral blood (median frequency $1.6 \times 10^{-6}$ and $7.2 \times 10^{-6}$ in T1D patients, respectively; median frequency across all peptides studied $7.6 \times 10^{-6}$, interquartile range $2.0 \times 10^{-6}$-$2.7 \times 10^{-5}$). MMr$^+$ cells could be detected in the pancreas of the 2 T1D cases selected for both IAPP$_{15\text{-}17/5\text{-}10}$ and ISL1$_{276\text{-}284}$ (data not shown), similar to what observed for the ZnT8$_{186\text{-}184}$ positive control islet peptide, while the MelanA$_{26\text{-}35}$ negative control melanocyte peptide did not give any appreciable staining. The presence of these reactivities in pancreatic immune infiltrates lends further support to their relevance in T1D.

Discussion

We here provide a first catalogue of the HLA Class I peptidome of human β cells, using an immortalized β-cell line expressing the most common HLA Class I variant HLA-A2. This cellular model proved informative, since several of the HLA-A2-restricted peptides identified were also found to be naturally processed and presented by primary human islets. The technical strengths of our approach are the combined HLA peptidomics and transcriptomics pipelines implemented; the use of small cell numbers (20×10$^6$) for HLA purification, despite its low expression in β cells compared with professional Ag-presenting cells; and the use of a mock immunopurification condition to exclude peptides not bound to HLA. One limitation is the lower sensitivity of the LC-MS/MS discovery mode used compared with targeted strategies. Indeed, previous studies on mouse NIT-1 β cells (Dudek et al., 2012) detected low numbers of the immunodominant IGRP$_{206\text{-}214}$ peptide only with a targeted approach on IFN-γ-treated cells. Nonetheless, our sensitivity proved sufficient to detect several known β-cell Ags. Although this did not allow a precise quantitation of pHLA complexes, it afforded the invaluable advantage of detecting HLA-bound peptides without a priori hypotheses. Expectedly, only ~5% of the HLA peptidome originated from proteins preferentially expressed in β cells. Multiple PPI peptides previously described as major CD8$^+$ T-cell epitopes were detected, lending validation to our discovery approach and adding new information about their natural processing and presentation by human β cells. Peptides derived from all the other known β-cell Ags were also identified, namely CHGA, PTPRN, GAD2, SLC30A8 and IAPP. The only known Ag missing was IGRP, which may reflect low amounts of IGRP pHLA complexes, as reported for murine NIT-1 β cells (Dudek et al., 2012). More importantly, several new peptides were identified, many of which were derived from proteins expressed in secretory granules, namely CHGA, INS, SCG5, PTPRN, ABCC8, PCSK1, UCN3, CHGB, CPE, PCSK2, SCG3, SCL30A8 and IAPP. This is not surprising considering that granule proteins are abundantly synthesized by β cells, thus increasing their odds of providing peptides for HLA presentation (Bassani-Sternberg et al., 2015). Their fast turnover also increases the chance of producing misfolded proteins, which are rapidly routed toward proteasomal degradation and HLA Class I presentation (Anton and Yewdell, 2014). mRNA alternative splicing is another mechanism frequently leading to unstable DRiPs, which are rapidly degraded through different pathways (Anton and Yewdell, 2014). Moreover, these mRNA isoforms may translate aa neo-sequences when exons are either added or skipped compared to the canonical mRNA (Juan-Mateu et al., 2016). We therefore performed a parallel in silico prediction of mRNA-translated peptide neo-sequences. Although no proof of natural processing and presentation could be provided for most of these theoretical peptide products, the finding of a naïve CD8$^+$ T-cell repertoire capable of recognizing them supports their potential relevance as autoimmune T-cell targets. Of note, peptides derived from the alternative open reading frame INS mRNA (Kracht et al., 2017) were not detected.

Despite presentation by HLA Class I molecules, peptides may still be ignored by CD8$^+$ T cells, thus not triggering an autoimmune response. This primarily reflects the absence of a cognate naïve repertoire available for priming (Alanio et al., 2010). We therefore first screened healthy individuals for the presence of cognate naïve CD8$^+$ T cells, which were found for several of these peptides. Although the poor expression of the genes encoding these proteins in mTECs may exert a facilitating effect, this is not an absolute requirement for peripheral CD8$^+$ T-cell recognition. Indeed, CHGA, ISL1 and SCG5 were expressed in mTECs, and yet targeted by CD8$^+$ T cells at frequencies comparable to those of T cells recognizing Ags not expressed in mTECs, in line with the increasing appreciation that thymic clonal deletion is rather incomplete (Culina et al., 2018; Yu et al., 2015).

Based on our previous findings on known β-cell epitopes (Culina et al., 2018), we did not expect differences in circulating CD8$^+$ T cells between T1D and healthy subjects, because the Ag-experienced fraction is rather limited, likely reflecting sequestration in the target tissue. This was also the case for the novel candidates studied herein. Together with the reactivity against some of these peptides detected in the pancreatic infiltrates of T1D patients, these findings provide a first validation of their disease relevance. Indeed, the well-described PPI$_{6-14}$ epitope was also eluted from pHLA complexes and behaved in a similar manner. The degree of evidence for a relevance to T1D is higher for those peptides targeted by CD8$^+$ T cells and naturally processed and presented by β cells (Di Lorenzo et al., 2007), i.e. SCG5$_{186-195}$, PCSK2$_{30-38}$, UCN3$_{1-9}$ and ISL1$_{276-284}$. These also include the neo-antigenic peptides SCG-009$_{186-194}$ and IAPP$_{15-17/5-10}$ generated by mRNA splicing and transpeptidation, respectively. Complementary analyses of the current HLA peptidomics dataset will yield additional information. First, only few PTMs were searched and a dedicated analysis is required. This should include the distinction between biological and experimentally induced PTMs, since some of them, e.g. the tryptophan to kinurenin conversion of the PPI$_{15-24}$ peptide, were similarly detected in the corresponding synthetic peptides. Second, an unbiased analysis of transpeptidation beyond the described aa preference rules (Berkers et al., 2015) will likely yield additional fusion peptides, which may account for up to one third of the HLA Class I peptidome (Liepe et al., 2016). Nonetheless, we were able to pinpoint a naturally processed and presented IA-PP$_{15-17/5-10}$ splice peptide recognized by CD8$^+$ T cells. Third, only HLA-A2-restricted peptides were analyzed for T-cell recognition, leaving several candidates available for follow-up studies, i.e. restricted for HLA-A3 and -B39. The latter was expressed by the primary islets analyzed and, although rare, is the Class I allotype most strongly associated with T1D (Nejentsev et al., 2007).

Finally, the HLA Class I peptidome obtained allows to formulate hypotheses about the Ag-processing pathways employed by β cells. Some peptides (UCN3$_{1-9}$, IA-PP$_{15-17/5-10}$, PPI$_{2-10}$, PPI$_{6-14}$, PPI$_{15-24}$) are located in the leader sequence. These proteins are abundantly produced by β cells, and the leader sequence is cleaved in the ER at each protein synthesis. These byproducts may therefore provide a rich source of peptides for HLA Class I presentation and likely follow alternative Ag-processing pathways within the ER, independent of proteasome cleavage (El Hage et al., 2008; Oliveira and van Hall, 2015; Skowera et al., 2008). It is also noteworthy that several proteins identified as sources of HLA-bound peptides, i.e. CHGA, INS, SCG5, PCSK1, UCN3, CHGB, CPE, PCSK2, SCG3 and IAPP are synthesized as precursors and incorporated into β-cell granules, where they undergo intermediate processing by proconvertases to yield bioactive products. A notable example is SCG5, a PCSK2 chaperone that is gradually degraded along the secretory pathway to competitively prevent the premature activation of PCSK2 by autocatalytic cleavage (Mbikay et al., 2001). This continuous degradation may explain the abundance of HLA-bound SCG5 peptides. In this respect, the SCG5186-195 peptide is located at the protein C-terminus, between furin and PCSK2 cleavage sites and, similar to leader sequence peptides, may behave as a byproduct of the intermediate SCG5 processing (Bartolomucci et al., 2011). The same is true for several CHGA peptides, e.g. CHGA$_{344-352}$, which maps to the WE-14 neuropeptide produced by CHGA cleavage at dibasic KR motifs (Bartolomucci et al., 2011). These peptides may access the HLA Class I pathway following crinophagy, i.e. the disposal of unused secretory granules through fusion with lysosomes (Goginashvili et al., 2015; Weckman et al., 2014). In this scenario, islet inflammation may provide a key switch for progression of the 'benign' autoimmunity of healthy individuals toward T1D at two levels: on T cells, by impairing peripheral immunoregulation; and on β cells, by making pHLA complexes increasingly available for T-cell recognition.

In conclusion, the HLA Class I peptidome of human β cells described herein provides information about the Ag processing features of β cells, the targets amenable to autoimmune recognition and a valuable tool for developing T-cell biomarkers and tolerogenic vaccines.

Example 2: In Silico Selection of T-Cell and Antibody Candidate Epitopes

Methods:

Peptides identified as potential CD8+ T-cell epitopes were selected using NetMHC 4.0 Server (www.cbs.dtu.dk/services/NetMHC) based on restriction for HLA-A*01:01 (A1), HLA-A*02:01 (A2), HLA-A*03:01 (A3), HLA-A*24:01 (A24), HLA-B*08:01 (B8) and HLA-B*40:01 (B40). Peptides identified as potential CD4+ T-cell epitopes were selected using NetMHCpan 3.1 Server (www.cbs.dtu.dk/services/NetMHCIIpan) based on restriction for HLA-DRB1*01:01 (DR1), HLA-DRB1*03:01 (DR3), HLA-DRB1*04:01 (DR4), HLA-DQA1*01:01/DQB1*02:01 (DQ2) and HLA-DQA1*03:01/DQB1*0302 (DQ8). Antibody epitope predictions were performed using the BepiPred Linear Epitope Prediction tool available through the Immune Epitope DataBase (IEDB; www.iedb.org). Peptides 8-11 aa- and 15 aa-long were selected for CD8+ and CD4+ T-cell epitope predictions, respectively, using a predicted HLA binding affinity cutoff of ≤250 nM. These analyses were applied to the aa sequence of UCN3. Hotspot regions within each of these aa sequences were defined based on the density of predicted epitopes and on described protease cleavage sites.

Results:
The results are depicted in Tables A.

Example 3: HLA-A3-Restricted Peptides Naturally Processed and Presented by Beta Cells are Recognized by Circulating CD8+ T Cells in Type 1 Diabetic and Healthy Donors Methods:
Blood Donors and Peripheral Blood Mononuclear Cell (PBMC) Processing HLA-A3$^+$ type 1 diabetic and healthy donors gave written informed consent and the study was approved by the local Ethics committees. Blood was drawn into 9 ml sodium heparin tubes and processed, counted and frozen as described (Gonzalez-Duque, Cell Metab 2018).

HLA-A3 Peptide Binding Assays

Experimental binding to HLA-A3 was measured by flow cytometry using biotin-tagged HLA-A*03:01 monomers (immunAware). Briefly, biotinylated monomers were folded as described (Gonzalez-Duque, Cell Metab 2018), and captured on streptavidin-coated beads (Spherotech). Beads were subsequently incubated with a primary anti-β2-microglobulin BBM.1 mAb (Santa Cruz) followed by a secondary Goat IgG anti-mouse IgG (H+L)-Alexa Fluor 488 (Interchim). The bead-associated fluorescence is only detected if the test peptide supports the folding of the HLA-A3 complex. Each peptide candidate-HLA-A3 complex was tested at a final concentration of 1.2 nM. The HLA-A3-binding peptide Flu NP265-273 (ILRGSVAHK), and a non-binding peptide CHGA$_{382-390}$ (HPVGEADYF) were included as positive and negative controls, respectively. Following acquisition on a BD Fortessa cytometer, results were analyzed by gating on single beads and Alexa-Fluor 488$^+$ events, and expressed as the median fluorescence intensity fold increase of the test peptide-HLA complex compared with the negative control complex at the same concentration.

Ex Vivo HLA-A3 Multimer (MMr) Staining

HLA-A3 MMrs were produced and used as described (Gonzalez-Duque, Cell Metab 2018). Each peptide-HLA-A3 complex was used at a final concentration of 8-27 nM and conjugated with fluorochrome-labeled streptavidin at a 1:4 ratio. The concentration of each fluorescent MMr was corrected for the variable staining index of each streptavidin, in order to obtain a distinct double-MMr$^+$ population for each fluorochrome pair. Compensations were set using fluorescence-minus-one samples (i.e. omitting one streptavidin at a time). The combinatorial MMr panel was first set up by staining HLA-A3$^+$ PBMCs with the same set of fluorescent streptavidin-labeled MMrs, all loaded with the Flu NP$_{265-273}$ epitope, which yielded a similar MMr$^+$CD8$^+$ T-cell frequency for all the 15 MMr combination pairs. The same MMr$^+$ population was identified for all combinations, except for the BV711$^+$BV786$^+$ population which displayed a lower staining intensity and was therefore subsequently used to detect the higher frequency population of positive control Flu NP265-273-reactive CD8$^+$ T cells.

PBMCs were thawed at 37° C. and immediately diluted in pre-warmed AIM-V medium. Following centrifugation and one additional wash in AIM-V, PBMCs were counted and rested in the presence of 50 nM dasatinib for 30 min at 37° C. to prevent internalization of T-cell receptors before magnetic depletion of CD8$^-$ cells (StemCell Technologies). Staining was performed for 20 min at 20° C. in 20 ml PBS-dasatinib for 10$^7$ cells with combinatorial double-coded MMr panels, followed, without washing, by CD3-APC-H7 (RRID AB_1645475), CD8-PE-Cy7 (AB_396852), CD45RA-FITC (AB_395879), CCR7-BV421 (AB_2728119) monoclonal antibodies and Live/Dead Aqua (ThermoFisher) staining at 4° C. for 20 min. After one wash, cells were acquired using a FACSAria III cytometer. Candidate epitopes binding to HLA-A3 that did not yield any appreciable MMr staining provided negative controls for each panel. Flow cytometry data were analyzed with FlowJo v10 and Graphpad Prism 7.0 software. Cells were sequentially gated on small lymphocytes, singlets, live cells (Live/Dead Aqua 1, CD3$^+$CD8$^+$ T cells and total PE$^+$, PE-CF594$^+$, APC$^+$, BV650$^+$, BV711$^+$ and BV786$^+$ MMr$^+$ T cells. Using Boolean operators, these latter gates allowed to selectively visualize each double-MMr$^+$ population by including only those events positive for the corresponding fluorochrome pair. For example, SCG3166-174 MMr$^+$ cells (PE$^+$PE-CF594$^+$) were visualized by gating on events that were PE$^+$PE-CF594$^+$APC$^-$BV650$^-$BV711$^-$BV786$^-$. Events negative for all MMr fluorochromes (PE$^-$PE-CF594$^-$APC$^-$BV650$^-$BV711$^-$BV786$^-$) were represented in the same PE/PE-CF-594 dot plot to set the double-MMr$^+$ gate. CD45RA and CCR7 staining was subsequently visualized by gating on these MMr$^+$ cells. Each dot plot displays a color-coded overlay of each double-MMr$^+$ fraction and of the MMr population to visualize the separation of each epitope-reactive CD8$^+$ T-cell fraction relative to the others (data not shown).

Results:
Peptides identified by in vitro HLA-A3 peptidomics and in silico pipelines bind HLA-A3.

Peptides predicted to be restricted for HLA-A3 identified by in vitro HLA-A3 peptidomics (and in silico pipelines for those predicted to be derived from mRNA alternative splicing) were available from our previous study (Gonzalez-Duque et al, *Cell Metab* 2018). A first selection was performed based on a novel HLA Class I binding assay that we set up. Briefly, the same biotinylated recombinant HLA-A3 monomeric molecules that are used for MMr production are folded with the test peptides and captured on streptavidin-coated beads. A fluorescently labeled anti-β2-microglobulin is then added, which gives a positive signal by flow cytometry only if the complex has folded around the peptide, i.e. if the peptide has a significant binding to HLA-A3. This assay is rapid and high throughput and further allows to verify that the HLA-A3 MMrs that are subsequently used for CD8$^+$ T-cell assays are viable. Based on this assay, all the peptides available were confirmed to be HLA-A3 binders and moved into T-cell validation studies (data not shown).

HLA-A3-restricted islet peptides are recognized by a similar frequency of largely naïve CD8$^+$ T cells in the blood of T1D and healthy donors.

Since the first requirement for a peptide to qualify as a T-cell epitope is the existence of a naïve T-cell repertoire capable of recognizing it, we performed a first screening round on 7 HLA-A3$^+$ healthy donors (data not shown). The 20 islet peptides recognized by circulating CD8$^+$ T cells displaying the expected frequency for naïve T-cell precursors (1-50/10$^6$ CD8$^+$ T cells) and a clustered MMr staining pattern (indicative of specific staining compared to spread staining patterns) were thus validated, and 12 of them were retained for further comparison between new-onset T1D and healthy adult donors. As expected, these MMr$^+$CD8$^+$ cells recognizing islet peptides were largely naïve.

In the second validation round on PBMC samples from T1D and healthy donors, eleven of the 12 peptides studied were validated as CD8$^+$ T-cell epitopes, with the single exception of PNMA2$_{50\text{-}58}$. These results confirm our previous observations on circulating CD8$^+$ T cells recognizing HLA-A2-restricted islet peptides, i.e. a similar frequency in T1D and healthy donors falling into the expected relatively narrow range of 1-50/10$^6$ CD8$^+$ T cells) and a largely naïve phenotype irrespective of disease status (although larger fractions of antigen-experienced cells were observed in this case).

Moreover, it is noted that several proteins previously identified as sources of HLA-A2-restricted epitopes gave positive hits also for the HLA-A3 restriction, namely KIF1A$_{860\text{-}868}$, secretogranins (SCG3$_{166\text{-}174}$ and the mRNA splice variant SCG5-009$_{193\text{-}201}$), UCN3$_{46\text{-}56}$, GNAS-036$_{74\text{-}83}$, GNAS-036$_{477\text{-}485}$). A spliced peptides derived from the fusion of two non-contiguous IA-2 sequences (PTPRN$_{576\text{-}580/708\text{-}711}$) was also identified.

The HLA-A3 restricted SCG5-009$_{193\text{-}201}$ peptide (RLKPSLVGK) maps to the same region of the HLA-A2-restricted epitope SCG5-009$_{186\text{-}194}$ previously identified (FLSGAVNRL; Gonzalez-Duque et al, Cell Metab 2018). UCN3$_{46\text{-}56}$ (GQWEDASLLSK) corresponds to SEQ ID NO: 33.

Discussion:

Collectively, these data provide another example that the islet peptides identified, e.g. those derived from SCG5-009 and UCN3, are recognized by circulating CD8$^+$ T cells. Their targeting by CD8$^+$ T cells is therefore not restricted to HLA-A2 but also applies to HLA-A3.

Example 4: Recognition of Murine UCN3 and PCSK2 Peptides by ISLET-Infltrating CD8+ T Cells of NOD Mice Methods:

Peptides predicted to be restricted by the murine MHC Class I K$^d$ molecule were identified using prediction algorithms and scanning of the whole murine protein sequence. Peptides were first tested in pools, and positive pools subsequently deconvoluted for reactivity against individual peptides. To this end, islets were isolated from 12-16-week-old NOD mice by collagenase digestion and put in culture with recombinant human IL-2 (Proleukin, Novartis) for 5 days as described (Brezar et al, Eur J Immunol 2012). Cells exiting the islets were subsequently collected and subjected to recall assays against K$^{d+}$ L antigen-presenting cells pulsed with the indicated peptides for 6 h in the presence of brefeldin-A, followed by intracellular staining for IFN-γ. The TUM, Ins B15-23 and IGRP 206-214 peptides were included as negative control and positive controls, respectively.

Results:

We performed experiments in 12-16-week-old NOD females by analyzing the reactivity of islet-infiltrating CD8$^+$ T cells to peptides derived from murine Ucn3 and Pcsk2 and predicted to be restricted by the murine MHC molecule K$^d$. A positive response was defined as a percentage of IFN-γ$^+$ CD8$^+$ cells >1.8%, which was the median response observed for the negative control TUM peptide. A significant recognition was observed for some of these peptides in the NOD mouse: Ucn3 5-13 (TYFLLPLLL; 8/12 positive mice, 67%; median value 2.3%, positive range 2.1-8.6%), Ucn3 32-40 (VFSCLNTAL; 8/12 positive mice, 67%; median 1.9%, positive range 1.9-3.3%), Pcsk2 109-118 (GYRDINEIDI; 6/8 positive mice, 50%; median 1.8%, positive range 1.9-4.3%), Pcsk2 341-350 (LYDESCSSTL; 6/8 positive mice, 75%; median 3.3%, positive range 1.9-5.2%), Pcsk2 501-510 (RYLEHVQAVI; 5/8 positive mice, 63%; median 2.7%, range 2.1-8.0%) and the positive controls Ins B15-23 (6/7 positive mice, 86%; median 2.0%, range 1.9-7.2%) and IGRP 206-214 (13/13 positive mice, 100%; median 12.5%, range 4.5-25.3%).

Of note, murine Ucn3 5-13 (TYFLLPLLL) maps to the same UCN3 1-21 immunogenic region identified in the human, with significant overlap with peptides UCN3 6-15 (HFLLLLLLLL; SEQ ID 10, UCN3 7-14 (FLLLLLLL; SEQ ID 11), UCN3 7-15 (FLLLLLLLL; SEQ ID 6 and UCN3 7-16 (FLLLLLLLLG; SEQ ID 12.

Similarly, murine Ucn3 32-40 (VFSCLNTAL) maps to the same UCN3 22-71 immunogenic region identified in the human, with significant overlap with peptides UCN3 27-36 (YKAKPIFSCL; SEQ ID 38), UCN3 27-41 (YKAKPIFSCLNTALS; SEQ ID 55), UCN3 25-33 (KFYKAKPIF; SEQ ID 37) and UCN3 25-39 (KFYKAKPIFSCLNTA; SEQ ID 44).

Discussion:

The finding of Ucn3- and PCsk2-reactive CD8+ T cells in the autoimmune infiltrates of pancreatic islets in the NOD mouse suggests a role for these antigens in disease pathogenesis. The sequences targeted here were, expectedly, different than those found in the human, given the incomplete homology between the mouse and the human protein isoforms and the use of a different MHC Class I restriction element, namely K$^d$, in the mouse. Nonetheless, significant overlaps with the immunogenic regions and peptides identified in the human were noted for Ucn3. Moreover, several proteins described in example 1, namely SCG5 (and its mRNA splice variant SCG5-009), UCN3 and PCSK2 gave positive hits for multiple HLA Class I restrictions and, in some cases, even across the human and mouse species. Several of these proteins share some interesting features with the major islet antigen preproinsulin: they are soluble proteins contained in the secretory granules of β cells and they are produced as precursors which undergo cleavage of their leader sequence and intermediate processing by enzymes such as proconvertases to give raise to their bioactive products. An impairment of proinsulin processing is increasingly described in T1D islets (Rodriguez-Calvo et al, Diabetes 2017; Wasserfall et al, Cell Metab 2017). Since these proteins pass through the same processing pathways, it is possible that they may be affected by a similar impairment, possibly explaining their immunogenicity.

TABLE A in silico selection of T-cell and antibody candidate epitopes for UCN3.

| Region | | Aa position | Sequence | Predicted restriction | Predicted affinity (nM) | Comments |
|---|---|---|---|---|---|---|
| UCN3 1-21 | CD8+ T-cell epitopes | | | HLA-A*0101 | | |
| | | 1-8 | MLMPVHFL | HLA-A*0201 | 22.7 | Overlap with peptides identified by MS |
| | | 1-9 | MLMPVHFLL | | 3.2 | Peptide identified by MS |
| | | 1-10 | MLMPVHFLLL | | 9.8 | Overlap with peptides identified by MS |
| | | 1-11 | MLMPVHFLLLL | | 27.4 | Overlap with peptides identified by MS |
| | | 7-15 | FLLLLLLLL | | 19.3 | Overlap with peptides identified by MS |
| | | 2-9 | LMPVHFLL | | 115.6 | Overlap with peptides identified by MS |
| | | 2-10 | LMPVHFLLL | | 214.6 | Overlap with peptides identified by MS |
| | | 2-11 | LMPVHFLLLL | | 88.8 | Overlap with peptides identified by MS |
| | | 6-15 | HFLLLLLLL | | 64.5 | Overlap with peptides identified by MS |
| | | 7-14 | FLLLLLLL | | 104.0 | Overlap with peptides identified by MS |
| | | 7-16 | FLLLLLLLLG | | 123.4 | Overlap with peptides identified by MS |
| | | 13-22 | LLLGGPRTGL | | 243.5 | |
| | | 18-28 | PRTGLPHKFYK | HLA-A*0301 | 244.6 | |
| | | 19-28 | RTGLPHKFYK | | 16.0 | |
| | | 21-30 | GLPHKFYKAK | | 211.6 | |
| | | | | HLA-A*2402 | | |
| | | 1-8 | MLMPVHFL | HLA-B*0801 | 125.6 | Overlap with peptides identified by MS |
| | | 1-9 | MLMPVHFLL | | 158.9 | Overlap with peptides identified by MS |
| | | 1-10 | MLMPVHFLLL | | 15.9 | Overlap with peptides identified by MS |
| | | 3-10 | MPVHFLLL | | 67.9 | Overlap with peptides identified by MS |
| | | | | HLA-B*4001 | | |
| | CD4+ T-cell epitopes | 7-21 | FLLLLLLLLGGPRTG | HLA-DRB1*0101 | 7.9 | Overlap with peptides identified by MS |
| | | 8-22 | LLLLLLLLGGPRTGL | | 6.0 | Overlap with peptides identified by MS |
| | | 9-23 | LLLLLLLGGPRTGLP | | 6.5 | Overlap with peptides identified by MS |
| | | 10-24 | LLLLLLGGPRTGLPH | | 7.6 | |
| | | 21-35 | GLPHKFYKAKPIFSC | | 7.1 | |
| | | 22-36 | LPHKFYKAKPIFSCL | | 5.2 | |
| | | | | HLA-DRB1*0301 | | |
| | | 21-35 | GLPHKFYKAKPIFSC | HLA-DRB1*0401 | 67.6 | |
| | | 22-36 | LPHKFYKAKPIFSCL | | 44.7 | |
| | | | | HLA-DQA1*0101-DQB1*0201 | | |
| | | | | HLA-DQA1*0301-DQB1*0302 | | |
| | Antibody epitopes | 18-27 | PRTGLPHKFY | | | |
| UCN3 22-71 | CD8+ T-cell epitopes | | | HLA-A*0101 | | |
| | | 46-54 | GQWEDASLL | HLA-A*0201 | 153.6 | Overlap with peptides identified by MS |
| | | 52-62 | SLLSKRSFHYL | | 233.2 | Overlap with peptides identified by MS |
| | | 53-62 | LLSKRSFHYL | | 115.5 | Overlap with peptides identified by MS |
| | | 46-56 | GQWEDASLLSK | HLA-A*0301 | 1970.9 | Peptide identified by MS |
| | | 52-61 | SLLSKRSFHY | | 121.4 | Overlap with peptides identified by MS |
| | | 53-61 | LLSKRSFHY | | 130.6 | Overlap with peptides identified by MS |

TABLE A-continued in silico selection of T-cell and antibody candidate epitopes for UCN3.

| Region | Aa position | Sequence | Predicted restriction | Predicted affinity (nM) | Comments |
|---|---|---|---|---|---|
| | 57-65 | RSFHYLRSR | | 183.4 | |
| | 25-33 | KFYKAKPIF | HLA-A*2402 | 196.0 | Overlap with peptides identified by MS |
| | 27-36 | YKAKPIFSCL | HLA-B*0801 | 221.5 | |
| | 52-59 | SLLSKRSF | | 156.0 | Overlap with peptides identified by MS |
| | 53-62 | LLSKRSFHYL | | 61.1 | Overlap with peptides identified by MS |
| | 61-69 | YLRSRDASS | | 95.0 | |
| | | | HLA-B*4001 | | |
| CD4+ T-cell epitopes | 23-37 | PHKFYKAKPIFSCLN | HLA-DRB1*0101 | 5.3 | |
| | 24-38 | HKFYKAKPIFSCLNT | | 5.7 | |
| | 25-39 | KFYKAKPIFSCLNTA | | 8.0 | |
| | 54-68 | LSKRSFHYLRSRDAS | | 7.8 | Overlap with peptides identified by MS |
| | 55-69 | SKRSFHYLRSRDASS | | 6.0 | Overlap with peptides identified by MS |
| | 56-70 | KRSFHYLRSRDASSG | | 5.7 | Overlap with peptides identified by MS |
| | 57-71 | RSFHYLRSRDASSGE | | 6.4 | |
| | 58-72 | SFHYLRSRDASSGEE | | 8.8 | |
| | 49-63 | EDASLLSKRSFHYLR | HLA-DRB1*0301 | 183.1 | Overlap with peptides identified by MS |
| | 50-64 | DASLLSKRSFHYLRS | | 175.2 | Overlap with peptides identified by MS |
| | 51-65 | ASLLSKRSFHYLRSR | | 168.9 | Overlap with peptides identified by MS |
| | 23-37 | PHKFYKAKPIFSCLN | HLA-DRB1*0401 | 47.2 | |
| | 24-38 | HKFYKAKPIFSCLNT | | 53.5 | |
| | 27-41 | YKAKPIFSCLNTALS | | 72.0 | |
| | 28-42 | KAKPIFSCLNTALSE | | 49.8 | |
| | 29-43 | AKPIFSCLNTALSEA | | 40.9 | |
| | 30-44 | KPIFSCLNTALSEAE | | 42.5 | |
| | 31-45 | PIFSCLNTALSEAEK | | 56.6 | |
| | 54-68 | LSKRSFHYLRSRDAS | | 62.2 | Overlap with peptides identified by MS |
| | 55-69 | SKRSFHYLRSRDASS | | 43.3 | Overlap with peptides identified by MS |
| | 56-70 | KRSFHYLRSRDASSG | | 40.5 | Overlap with peptides identified by MS |
| | 57-71 | RSFHYLRSRDASSGE | | 47.4 | |
| | 58-72 | SFHYLRSRDASSGEE | | 70.9 | |
| | | | HLA-DQA1*0101-DQB1*0201 | | |
| | | | HLA-DQA1*0301-DQB1*0302 | | |
| Antibody epitopes | 18-27 | PRTGLPHKFY | | | |
| | 40-53 | LSEAEKGQWEDASL | | | Overlap with peptides identified by MS |
| | 64-119 | SRDASSGEEEEGKEKKTFPISGARGGARGTRYRYVSQAQPRGKPRQDTAKSPHRTK | | | |
| UCN3 119-162 | CD8+ T-cell epitopes | | HLA-A*0101 | | |
| | 121-130 | TLSLDVPTNI | HLA-A*0201 | 234.1 | |
| | 128-137 | TNIMNLLFNI | | 84.8 | |
| | 129-137 | NIMNLLFNI | | 14.0 | |
| | 130-137 | IMNLLFNI | | 188.2 | |
| | 130-139 | IMNLLFNIAK | HLA-A*0301 | 47.2 | |
| | 131-141 | MNLLFNIAKAK | | 194.9 | |
| | 132-141 | NLLFNIAKAK | | 174.4 | |
| | 133-141 | LLFNIAKAK | | 24.5 | |
| | 151-160 | AHLMAQIGRK | | 21.3 | |
| | 152-160 | HLMAQIGRK | | 11.2 | |
| | 152-161 | LMAQIGRKK | | 18.2 | |
| | 153-161 | LMAQIGRKK | | 157.6 | |
| | | | HLA-A*2402 | | |
| | | | HLA-B*0801 | | |
| | | | HLA-B*4001 | | |

TABLE A-continued in silico selection of T-cell and antibody candidate epitopes for UCN3.

| Region | Aa position | Sequence | Predicted restriction | Predicted affinity (nM) | Comments |
|---|---|---|---|---|---|
| CD4+ T-cell epitopes | 130-144 | IMNLLFNIAKAKNLR | HLA-DRB1*0101 | 5.4 | |
| | 131-145 | MNLLFNIAKAKNLRA | | 4.5 | |
| | 132-146 | NLLFNIAKAKNLRAQ | | 4.3 | |
| | 133-147 | LLFNIAKAKNLRAQA | | 4.5 | |
| | 134-148 | LFNIAKAKNLRAQAA | | 5.9 | |
| | 138-152 | AKAKNLRAQAAANAH | | 9.1 | |
| | 139-153 | KAKNLRAQAAANAHL | | 6.2 | |
| | 140-154 | AKNLRAQAAANAHLM | | 5.7 | |
| | 141-155 | KNLRAQAAANAHLMA | | 6.2 | |
| | 120-134 | FTLSLDVPTNIMNLL | HLA-DRB1*0301 | 124.3 | |
| | 121-135 | TLSLDVPTNIMNLLF | | 213.5 | |
| | 130-144 | IMNLLFNIAKAKNLR | | 184.5 | |
| | 131-145 | MNLLFNIAKAKNLRA | | 129.3 | |
| | 132-146 | NLLFNIAKAKNLRAQ | | 112.7 | |
| | 133-147 | LLFNIAKAKNLRAQA | | 119.4 | |
| | 134-148 | LFNIAKAKNLRAQAA | | 157.5 | |
| | 131-145 | MNLLFNIAKAKNLRA | HLA-DRB1*0401 | 66.0 | |
| | 132-146 | NLLFNIAKAKNLRAQ | | 54.9 | |
| | 133-147 | LLFNIAKAKNLRAQA | | 52.8 | |
| | 134-148 | LFNIAKAKNLRAQAA | | 68.0 | |
| | 139-153 | KAKNLRAQAAANAHL | | 64.6 | |
| | 140-154 | AKNLRAQAAANAHLM | | 58.4 | |
| | 141-155 | KNLRAQAAANAHLMA | | 70.0 | |
| | | | HLA-DQA1*0101-DQB1*0201 | | |
| | | | HLA-DQA1*0301-DQB1*0302 | | |
| Antibody epitopes | 142-149 | NLRAQAAA | | | |

REFERENCES

Throughout this application, various references describe the state of the art to which this invention pertains. The disclosures of these references are hereby incorporated by reference into the present disclosure.

Alanio, C., Lemaitre, F., Law, H. K., Hasan, M., and Albert, M. L. (2010). Enumeration of human antigen-specific naive CD8+ T cells reveals conserved precursor frequencies. Blood 115, 3718-3725.

Andersen, R. S., Kvistborg, P., Frosig, T. M., Pedersen, N. W., Lyngaa, R., Bakker, A. H., Shu, C. J., Staten, P., Schumacher, T. N., and Hadrup, S. R. (2012). Parallel detection of antigen-specific T cell responses by combinatorial encoding of MHC multimers. Nat. Protoc. 7, 891-902.

Andreatta, M., and Nielsen, M. (2016). Gapped sequence alignment using artificial neural networks: application to the MHC class I system. Bioinformatics 32, 511-517.

Anton, L. C., and Yewdell, J. W. (2014). Translating DRiPs: MHC class I immunosurveillance of pathogens and tumors. J. Leukoc. Biol. 95, 551-562.

Babon, J. A., DeNicola, M. E., Blodgett, D. M., Crevecoeur, I., Buttrick, T. S., Maehr, R., Bottino, R., Naji, A., Kaddis, J., Elyaman, W., et al. (2016). Analysis of self-antigen specificity of islet-infiltrating T cells from human donors with type 1 diabetes. Nat. Med. 22, 1482-1487.

Bartolomucci, A., Possenti, R., Mahata, S. K., Fischer-Colbrie, R., Loh, Y. P., and Salton, S. R. (2011). The extended granin family: structure, function, and biomedical implications. Endocr. Rev. 32, 755-797.

Bassani-Sternberg, M., Pletscher-Frankild, S., Jensen, L. J., and Mann, M. (2015). Mass spectrometry of human leukocyte antigen class I peptidomes reveals strong effects of protein abundance and turnover on antigen presentation. Mol. Cell. Proteomics 14, 658-673.

Berkers, C. R., de Jong, A., Schuurman, K. G., Linnemann, C., Meiring, H. D., Janssen, L., Neefjes, J. J., Schumacher, T. N., Rodenko, B., and Ovaa, H. (2015). Definition of proteasomal peptide splicing rules for high-efficiency spliced peptide presentation by MHC Class I molecules. J. Immunol. 195, 4085-4095.

Caron, E., Espona, L., Kowalewski, D. J., Schuster, H., Ternette, N., Alpizar, A., Schittenhelm, R. B., Ramarathinam, S. H., Lindestam Arlehamn, C. S., Chiek Koh, C., et al. (2015). An open-source computational and data resource to analyze digital maps of immunopeptidomes. eLife 4.

Cnop, M., Abdulkarim, B., Bottu, G., Cunha, D. A., Igoillo-Esteve, M., Masini, M., Turatsinze, J. V., Griebel, T., Villate, O., Santin, I., et al. (2014). RNA sequencing identifies dysregulation of the human pancreatic islet transcriptome by the saturated Fatty Acid palmitate. Diabetes 63, 1978-1993.

Coppieters, K. T., Dotta, F., Amirian, N., Campbell, P. D., Kay, T. W., Atkinson, M. A., Roep, B. O., and von Herrath, M. G. (2012). Demonstration of islet-autoreactive CD8 T cells in insulitic lesions from recent onset and long-term type 1 diabetes patients. J. Exp. Med. 209, 51-60.

Culina, S., Lalanne, A. I., Afonso, G., Cerosaletti, K., Pinto, S., Sebastiani, G., Kuranda, K., Nigi, L., Eugster, A., Osterbye, T., et al. (2018). Islet-reactive CD8+ T-cell frequencies in the pancreas but not blood distinguish type 1 diabetes from healthy donors. Sci. Immunol. in press.

Delong, T., Wiles, T. A., Baker, R. L., Bradley, B., Barbour, G., Reisdorph, R., Armstrong, M., Powell, R. L., Reisdorph, N., Kumar, N., et al. (2016). Pathogenic CD4 T cells in type 1 diabetes recognize epitopes formed by peptide fusion. Science 351, 711-714.

Di Lorenzo, T. P., Peakman, M., and Roep, B. O. (2007). Translational mini-review series on type 1 diabetes: Systematic analysis of T cell epitopes in autoimmune diabetes. Clin. Exp. Immunol. 148, 1-16.

Dudek, N. L., Tan, C. T., Gorasia, D. G., Croft, N. P., Illing, P. T., and Purcell, A. W. (2012). Constitutive and inflammatory immunopeptidome of pancreatic beta-cells. Diabetes 61, 3018-3025.

Eizirik, D. L., Colli, M. L., and Ortis, F. (2009). The role of inflammation in insulitis and beta-cell loss in type 1 diabetes. Nat. Rev. Endocrinol. 5, 219-226.

Eizirik, D. L., Sammeth, M., Bouckenooghe, T., Bottu, G., Sisino, G., Igoillo-Esteve, M., Ortis, F., Santin, I., Colli, M. L., Barthson, J., et al. (2012). The human pancreatic islet transcriptome: expression of candidate genes for type 1 diabetes and the impact of pro-inflammatory cytokines. PLoS Genet. 8, e1002552.

El Hage, F., Stroobant, V., Vergnon, I., Baurain, J. F., Echchakir, H., Lazar, V., Chouaib, S., Coulie, P. G., and Mami-Chouaib, F. (2008). Preprocalcitonin signal peptide generates a cytotoxic T lymphocyte-defined tumor epitope processed by a proteasome-independent pathway. Proc. Natl. Acad. Sci. U.S.A. 105, 10119-10124.

Goginashvili, A., Zhang, Z., Erbs, E., Spiegelhalter, C., Kessler, P., Mihlan, M., Pasquier, A., Krupina, K., Schieber, N., Cinque, L., et al. (2015). Insulin granules. Insulin secretory granules control autophagy in pancreatic beta cells. Science 347, 878-882.

Gubin, M. M., Zhang, X., Schuster, H., Caron, E., Ward, J. P., Noguchi, T., Ivanova, Y., Hundal, J., Arthur, C. D., Krebber, W. J., et al. (2014). Checkpoint blockade cancer immunotherapy targets tumour-specific mutant antigens. Nature 515, 577-581.

Hadrup, S. R., Bakker, A. H., Shu, C. J., Andersen, R. S., van, V. J., Hombrink, P., Castermans, E., Thor, S. P., Blank, C., Haanen, J. B., et al. (2009). Parallel detection of antigen-specific T-cell responses by multidimensional encoding of MHC multimers. Nat. Methods 6, 520-526.

James, E. A., Abreu, J. R. F., McGinty, J. W., Odegard, J. M., Fillie, Y. E., Hocter, C. N., Culina, S., Ladell, K., Price, D. A., Alkanani, A., et al. (2017). Combinatorial detection of autoreactive CD8(+) T cells with HLA-A2 multimers: a multi-centre study by the Immunology of Diabetes Society T Cell Workshop. Diabetologia doi: 10.1007/s00125-017-4508-8.

Jorgensen, K. W., Rasmussen, M., Buus, S., and Nielsen, M. (2014). NetMHCstab-predicting stability of peptide-MHC-I complexes; impacts for cytotoxic T lymphocyte epitope discovery. Immunology 141, 18-26.

Juan-Mateu, J., Villate, O., and Eizirik, D. L. (2016). MECHANISMS IN ENDOCRINOLOGY: Alternative splicing: the new frontier in diabetes research. Eur. J. Endocrinol. 174, R225-238.

Keshava Prasad, T. S., Goel, R., Kandasamy, K., Keerthikumar, S., Kumar, S., Mathivanan, S., Telikicherla, D., Raju, R., Shafreen, B., Venugopal, A., et al. (2009). Human Protein Reference Database—2009 update. Nucleic Acids Res. 37, D767-772.

Khodadoust, M. S., Olsson, N., Wagar, L. E., Haabeth, O. A., Chen, B., Swaminathan, K., Rawson, K., Liu, C. L., Steiner, D., Lund, P., et al. (2017). Antigen presentation profiling reveals recognition of lymphoma immunoglobulin neoantigens. Nature 543, 723-727.

Kracht, M. J., van Lummel, M., Nikolic, T., Joosten, A. M., Laban, S., van der Slik, A. R., van Veelen, P. A., Carlotti, F., de Koning, E. J., Hoeben, R. C., et al. (2017). Autoimmunity against a defective ribosomal insulin gene product in type 1 diabetes. Nat. Med. 23, 501-507.

Leisner, C., Loeth, N., Lamberth, K., Justesen, S., Sylvester-Hvid, C., Schmidt, E. G., Claesson, M., Buus, S., and Stryhn, A. (2008). One-pot, mix-and-read peptide-MHC tetramers. PLoS One 3, e1678.

Li, Y., Zhou, L., Li, Y., Zhang, J., Guo, B., Meng, G., Chen, X., Zheng, Q., Zhang, L., Zhang, M., et al. (2015). Identification of autoreactive CD8+ T cell responses targeting chromogranin A in humanized NOD mice and type 1 diabetes patients. Clin. Immunol. 159, 63-71.

Liepe, J., Marino, F., Sidney, J., Jeko, A., Bunting, D. E., Sette, A., Kloetzel, P. M., Stumpf, M. P., Heck, A. J., and Mishto, M. (2016). A large fraction of HLA class I ligands are proteasome-generated spliced peptides. Science 354, 354-358.

Lissina, A., Ladell, K., Skowera, A., Clement, M., Edwards, E., Seggewiss, R., van den Berg, H. A., Gostick, E., Gallagher, K., Jones, E., et al. (2009). Protein kinase inhibitors substantially improve the physical detection of T-cells with peptide-MHC tetramers. J. Immunol. Methods 340, 11-24.

Mallone, R., Martinuzzi, E., Blancou, P., Novelli, G., Afonso, G., Dolz, M., Bruno, G., Chaillous, L., Chatenoud, L., Bach, J. M., et al. (2007). CD8+ T-cell responses identify beta-cell autoimmunity in human type 1 diabetes. Diabetes 56, 613-621.

Marroqui, L., Dos Santos, R. S., Floyel, T., Grieco, F. A., Santin, I., Op de Beeck, A., Marselli, L., Marchetti, P., Pociot, F., and Eizirik, D. L. (2015). TYK2, a candidate gene for type 1 diabetes, modulates apoptosis and the innate immune response in human pancreatic beta-cells. Diabetes 64, 3808-3817.

Marroqui, L., Dos Santos, R. S., Op de Beeck, A., Coomans de Brachene, A., Marselli, L., Marchetti, P., and Eizirik, D. L. (2017). Interferon-alpha mediates human beta cell HLA class I overexpression, endoplasmic reticulum stress and apoptosis, three hallmarks of early human type 1 diabetes. Diabetologia 60, 656-667.

Marroqui, L., Santin, I., Dos Santos, R. S., Marselli, L., Marchetti, P., and Eizirik, D. L. (2014). BACH2, a candidate risk gene for type 1 diabetes, regulates apoptosis in pancreatic beta-cells via JNK1 modulation and crosstalk with the candidate gene PTPN2. Diabetes 63, 2516-2527.

Martinuzzi, E., Novelli, G., Scotto, M., Blancou, P., Bach, J. M., Chaillous, L., Bruno, G., Chatenoud, L., van, E. P., and Mallone, R. (2008). The frequency and immunodominance of islet-specific CD8+ T-cell responses change after type 1 diabetes diagnosis and treatment. Diabetes 57, 1312-1320.

Mbikay, M., Seidah, N. G., and Chretien, M. (2001). Neuroendocrine secretory protein 7B2: structure, expression and functions. Biochem. J. 357, 329-342.

McGinty, J. W., Chow, I. T., Greenbaum, C., Odegard, J., Kwok, W. W., and James, E. A. (2014). Recognition of post-translationally modified glutamic acid decarboxylase 65 epitopes in subjects with type 1 diabetes. Diabetes 63, 3033-3040.

Moore, F., Colli, M. L., Cnop, M., Esteve, M. I., Cardozo, A. K., Cunha, D. A., Bugliani, M., Marchetti, P., and Eizirik, D. L. (2009). PTPN2, a candidate gene for type 1 diabetes, modulates interferon-gamma-induced pancreatic beta-cell apoptosis. Diabetes 58, 1283-1291.

Nejentsev, S., Howson, J. M., Walker, N. M., Szeszko, J., Field, S. F., Stevens, H. E., Reynolds, P., Hardy, M., King, E., Masters, J., et al. (2007). Localization of type 1 diabetes susceptibility to the MHC class I genes HLA-B and HLA-A. Nature 450, 887-892.

Oliveira, C. C., and van Hall, T. (2015). Alternative antigen processing for MHC Class I: multiple roads lead to Rome. Front. Immunol. 6, 298.

Op de Beeck, A., and Eizirik, D. L. (2016). Viral infections in type 1 diabetes mellitus—why the beta cells? Nat. Rev. Endocrinol. 12, 263-273.

Ortis, F., Naamane, N., Flamez, D., Ladriere, L., Moore, F., Cunha, D. A., Colli, M. L., Thykjaer, T., Thorsen, K., Orntoft, T. F., et al. (2010). Cytokines interleukin-1beta and tumor necrosis factor-alpha regulate different transcriptional and alternative splicing networks in primary beta-cells. Diabetes 59, 358-374.

Pinto, S., Sommermeyer, D., Michel, C., Wilde, S., Schendel, D., Uckert, W., Blankenstein, T., and Kyewski, B. (2014). Misinitiation of intrathymic MART-1 transcription and biased TCR usage explain the high frequency of MART-1-specific T cells. Eur. J. Immunol. 44, 2811-2821.

Ravassard, P., Hazhouz, Y., Pechberty, S., Bricout-Neveu, E., Armanet, M., Czernichow, P., and Scharfmann, R. (2011). A genetically engineered human pancreatic beta cell line exhibiting glucose-inducible insulin secretion. J. Clin. Invest. 121, 3589-3597.

Rondas, D., Crevecoeur, I., D'Hertog, W., Bomfim Ferreira, G., Staes, A., Garg, A. D., Eizirik, D. L., Agostinis, P., Gevaert, K., Overbergh, L., et al. (2015). Citrullinated glucose-regulated protein 78 is an autoantigen in type 1 diabetes. Diabetes 64, 573-586.

Scotto, M., Afonso, G., Larger, E., Raverdy, C., Lemonnier, F. A., Carel, J. C., Dubois-Laforgue, D., Baz, B., Levy, D., Gautier, J. F., et al. (2012). Zinc transporter (ZnT)8(186-194) is an immunodominant CD8+ T cell epitope in HLA-A2+ type 1 diabetic patients. Diabetologia 55, 2026-2031.

Segerstolpe, A., Palasantza, A., Eliasson, P., Andersson, E. M., Andreasson, A. C., Sun, X., Picelli, S., Sabirsh, A., Clausen, M., Bjursell, M. K., et al. (2016). Single-cell transcriptome profiling of human pancreatic islets in health and type 2 diabetes. Cell Metab. 24, 593-607.

Skowera, A., Ellis, R. J., Varela-Calvino, R., Arif, S., Huang, G. C., Van-Krinks, C., Zaremba, A., Rackham, C., Allen, J. S., Tree, T. I., et al. (2008). CTLs are targeted to kill beta cells in patients with type 1 diabetes through recognition of a glucose-regulated preproinsulin epitope. J. Clin. Invest. 118, 3390-3402.

Standifer, N. E., Ouyang, Q., Panagiotopoulos, C., Verchere, C. B., Tan, R., Greenbaum, C. J., Pihoker, C., and Nepom, G. T. (2006). Identification of novel HLA-A*0201-restricted epitopes in recent-onset type 1 diabetic subjects and antibody-positive relatives. Diabetes 55, 3061-3067.

Suckale, J., and Solimena, M. (2010). The insulin secretory granule as a signaling hub. Trends in endocrinology and metabolism: Trends Endocrinol. Metab. 21, 599-609.

Uhlen, M., Fagerberg, L., Hallstrom, B. M., Lindskog, C., Oksvold, P., Mardinoglu, A., Sivertsson, A., Kampf, C., Sjostedt, E., Asplund, A., et al. (2015). Proteomics. Tissue-based map of the human proteome. Science 347, 1260419.

Villate, O., Turatsinze, J. V., Mascali, L. G., Grieco, F. A., Nogueira, T. C., Cunha, D. A., Nardelli, T. R., Sammeth, M., Salunkhe, V. A., Esguerra, J. L., et al. (2014). Noval is a master regulator of alternative splicing in pancreatic beta cells. Nucleic Acids Res. 42, 11818-11830.

Vomund, A. N., Zinselmeyer, B. H., Hughes, J., Calderon, B., Valderrama, C., Ferris, S. T., Wan, X., Kanekura, K., Carrero, J. A., Urano, F., et al. (2015). Beta cells transfer vesicles containing insulin to phagocytes for presentation to T cells. Proc. Natl. Acad. Sci. U.S.A. 112, E5496-5502.

Weckman, A., Di Ieva, A., Rotondo, F., Syro, L. V., Ortiz, L. D., Kovacs, K., and Cusimano, M. D. (2014). Autophagy in the endocrine glands. J. Mol. Endocrinol. 52, R151-163.

Yadav, M., Jhunjhunwala, S., Phung, Q. T., Lupardus, P., Tanguay, J., Bumbaca, S., Franci, C., Cheung, T. K., Fritsche, J., Weinschenk, T., et al. (2014). Predicting immunogenic tumour mutations by combining mass spectrometry and exome sequencing. Nature 515, 572-576.

Yu, W., Jiang, N., Ebert, P. J., Kidd, B. A., Muller, S., Lund, P. J., Juang, J., Adachi, K., Tse, T., Birnbaum, M. E., et al. (2015). Clonal deletion prunes but does not eliminate self-specific alphabeta CD8(+) T lymphocytes. Immunity 42, 929-941.

---

The invention claimed is:

1. A fusion protein comprising a peptide fused to a heterologous polypeptide or an immunoconjugate comprising an antibody fused or conjugated to the peptide, wherein the peptide comprises at least 8 consecutive amino acids of urocortin 3 (UCN3), and wherein:
   the at least 8 consecutive amino acids comprise the sequence ranging from the amino acid residue at position 1 to the amino acid residue at position 21 in SEQ ID NO:1 (UCN3), or
   the at least 8 consecutive amino acids comprise the sequence ranging from the amino acid residue at position 22 to the amino acid residue at position 71 in SEQ ID NO:1 (UCN3), or
   the at least 8 consecutive amino acids comprise the sequence ranging from the amino acid residue at position 119 to the amino acid residue at position 162 in SEQ ID NO:1 (UCN3);
   and wherein the peptide is not SEQ ID NO: 2 (MLMPVHFL), SEQ ID NO: 3 (MLMPVHFLL) or SEQ ID NO: 7 (LMPVHFLL).

2. The fusion protein or the immunoconjugate of claim 1, wherein the peptide consists of the amino acid sequence as set forth in SEQ ID NO: 4 (MPVHFLLL) or SEQ ID NO: 34 (SLLSKRSFHY).

3. The fusion protein or the immunoconjugate of claim 1, wherein the peptide consists of the amino acid sequence as set forth in SEQ ID NO: 4 (MLMPVHFLLL), SEQ ID NO: 5 (MLMPVHFLLLL), SEQ ID NO: 6 (FLLLLLLLL), SEQ ID NO: 8 (LMPVHFLLL), SEQ ID NO: 9 (LMPVHFLLLL), SEQ ID NO: 10 (HFLLLLLLLL), SEQ ID NO: 11 (FLLLLLLL), SEQ ID NO: 12 (FLLLLLLLLG), SEQ ID NO: 13 (LLLGGPRTGL), SEQ ID NO: 14 (PRTGLPHKFYK), SEQ ID NO: 15 (RTGLPHKFYK), SEQ ID NO: 16 (GLPHKFYKAK), SEQ ID NO: 20 (MPVHFLLL), SEQ ID NO: 21 (FLLLLLLLLGGPRTG), SEQ ID NO: 22 (LLLLLLLLGGPRTGL), SEQ ID NO: 23 (LLLLLLLGGPRTGLP), SEQ ID NO: 24 (LLLLLLGGPRTGLPH), SEQ ID NO: 25 (GLPHKFYKAKPIFSC), SEQ ID NO: 26 (LPHKFYKAKPIFSCL), SEQ ID NO: 27 (GLPHKFYKAKPIFSC), SEQ ID NO: 28 (LPHKFYKAKPIFSCL), SEQ ID NO: 29 (PRTGLPHKFY), SEQ ID NO: 30 (GQWEDASLL), SEQ ID NO: 31 (SLLSKRSFHYL), SEQ ID NO: 32 (LLSKRSFHYL), SEQ ID NO: 33 (GQWEDASLLSK), SEQ ID NO: 34 (SLLSKRSFHY), SEQ ID NO: 35 (LLSKRSFHY), SEQ ID NO: 36 (RSFHYLRSR), SEQ ID NO: 37 (KFYKAKPIF), SEQ ID NO: 38 (YKAKPIFSCL), SEQ ID NO: 39 (SLLSKRSF), SEQ ID NO: 40 (LLSKRSFHYL), SEQ ID NO: 41 (YLRSRDASS), SEQ ID NO: 42 (PHKFYKAKPIFSCLN), SEQ ID NO: 43 (HKFYKAKPIFSCLNT), SEQ ID NO: 44 (KFYKAKPIFSCLNTA), SEQ ID NO: 45 (LSKRSFHYLRSRDAS), SEQ ID NO: 46 (SKRSFHYLRSRDASS), SEQ ID NO: 47 (KRSFHYLRSRDASSG), SEQ ID NO: 48 (RSFHYLRSRDASSGE), SEQ ID NO: 49 (SFHYLRSRDASSGEE), SEQ ID NO: 50 (EDASLLSKRSFHYLR), SEQ ID NO: 51 (DASLLSKRSFHYLRS), SEQ ID NO: 52 (ASLLSKRSFHYLRSR), SEQ ID NO: 53 (PHKFYKAKPIFSCLN), SEQ ID NO: 54 (HKFYKAKPIFSCLNT), SEQ ID NO: 55 (YKAKPIFSCLNTALS), SEQ ID NO: 56 (KAKPIFSCLNTALSE), SEQ ID NO: 57 (AKPIFSCLNTALSEA), SEQ ID NO: 58 (KPIFSCLNTALSEAE), SEQ ID NO: 59 (PIFSCLNTALSEAEK), SEQ ID NO: 60 (LSKRSFHYLRSRDAS), SEQ ID NO: 61 (SKRSFHYLRSRDASS), SEQ ID NO: 62 (KRSFHYLRSRDASSG), SEQ ID NO: 63 (RSFHYLRSRDASSGE), SEQ ID NO: 64 (SFHYLRSRDASSGEE), SEQ ID NO: 65 (PRTGLPHKFY), SEQ ID NO: 66 (LSEAEKGQWEDASL), SEQ ID NO: 67 (SRDASSGEEEEGKEKKTFPISGARG-GARGTRYRYVSQAQPRGKPRQDTAKSPHR TK), SEQ ID NO: 68 (TLSLDVPTNI), SEQ ID NO: 69 (TNIMNLLFNI), SEQ ID NO: 70 (NIMNLLFNI), SEQ ID NO: 71 (IMNLLFNI), SEQ ID NO: 72 (IMNLLFNIAK), SEQ ID NO: 73 (MNLLFNIAKAK), SEQ ID NO: 74 (NLLFNIAKAK), SEQ ID NO: 75 (LLFNIAKAK), SEQ ID NO: 76 (AHLMAQIGRK), SEQ ID NO: 77 (HLMAQIGRK), SEQ ID NO: 78 (HLMAQIGRKK), SEQ ID NO: 79 (LMAQIGRKK), SEQ ID NO: 80 (IMNLLFNIAKAKNLR), SEQ ID NO: 81 (MNLLFNIAKAKNLRA), SEQ ID NO: 82 (NLLFNIAKAKNLRAQ), SEQ ID NO: 83 (LLFNIAKAKNLRAQA), SEQ ID NO: 84 (LFNIAKAKNLRAQAA), SEQ ID NO: 85 (AKAKNLRAQAAANAH), SEQ ID NO: 86 (KAKNLRAQAAANAHL), SEQ ID NO: 87 (AKNLRAQAAANAHLM), SEQ ID NO: 88 (KNLRAQAAANAHLMA), SEQ ID NO: 89 (FTLSLDVPTNIMNLL), SEQ ID NO: 90 (TLSLDVPTNIMNLLF), SEQ ID NO: 91 (IMNLLFNIAKAKNLR), SEQ ID NO: 92 (MNLLFNIAKAKNLRA), SEQ ID NO: 93 (NLLFNIAKAKNLRAQ), SEQ ID NO: 94 (LLFNIAKAKNLRAQA), SEQ ID NO: 95 (LFNIAKAKNLRAQAA), SEQ ID NO: 96 (MNLLFNIAKAKNLRA), SEQ ID NO: 97 (NLLFNIAKAKNLRAQ), SEQ ID NO: 98 (LLFNIAKAKNLRAQA), SEQ ID NO: 99 (LFNIAKAKNLRAQAA), SEQ ID NO: 100 (KAKNLRAQAAANAHL), SEQ ID NO: 101 (AKNLRAQAAANAHLM), SEQ ID NO: 102 (KNLRAQAAANAHLMA), or SEQ ID NO: 103 (NLRAQAAA).

4. The immunoconjugate of claim 1, wherein the antibody is directed against a surface antigen of an antigen presenting cell so that the peptide is targeted to said antigen presenting cell to elicit an immune response.

5. A pharmaceutical or vaccine composition comprising the fusion protein or the immunoconjugate of claim 1.

6. The immunoconjugate of claim 4, wherein the immune response is tolerance.

7. A composition comprising a peptide and an adjuvant, wherein the peptide comprises at least 8 consecutive amino acids of urocortin 3 (UCN3), and wherein:
  the at least 8 consecutive amino acids comprise the sequence ranging from the amino acid residue at position 1 to the amino acid residue at position 21 in SEQ ID NO:1 (UCN3), or
  the at least 8 consecutive amino acids comprise the sequence ranging from the amino acid residue at position 22 to the amino acid residue at position 71 in SEQ ID NO:1 (UCN3), or
  the at least 8 consecutive amino acids comprise the sequence ranging from the amino acid residue at position 119 to the amino acid residue at position 162 in SEQ ID NO:1 (UCN3);
  and wherein the peptide is not SEQ ID NO: 2 (MLMPVHFL), SEQ ID NO: 3(MLMPVHFLL) or SEQ ID NO: 7 (LMPVHFLL).

* * * * *

SEQUENCE LISTING

```
<160> NUMBER OF SEQ ID NOS: 103

<210> SEQ ID NO 1
<211> LENGTH: 161
<212> TYPE: PRT
<213> ORGANISM: Homo sapiens

<400> SEQUENCE: 1

Met Leu Met Pro Val His Phe Leu Leu Leu Leu Leu Leu Leu Leu Gly
1               5                   10                  15

Gly Pro Arg Thr Gly Leu Pro His Lys Phe Tyr Lys Ala Lys Pro Ile
            20                  25                  30

Phe Ser Cys Leu Asn Thr Ala Leu Ser Glu Ala Glu Lys Gly Gln Trp
        35                  40                  45

Glu Asp Ala Ser Leu Leu Ser Lys Arg Ser Phe His Tyr Leu Arg Ser
    50                  55                  60

Arg Asp Ala Ser Ser Gly Glu Glu Glu Gly Lys Glu Lys Lys Thr
65                  70                  75                  80

Phe Pro Ile Ser Gly Ala Arg Gly Gly Ala Arg Gly Thr Arg Tyr Arg
```

85                  90                  95
Tyr Val Ser Gln Ala Gln Pro Arg Gly Lys Pro Arg Gln Asp Thr Ala
                100                 105                 110

Lys Ser Pro His Arg Thr Lys Phe Thr Leu Ser Leu Asp Val Pro Thr
            115                 120                 125

Asn Ile Met Asn Leu Leu Phe Asn Ile Ala Lys Ala Lys Asn Leu Arg
        130                 135                 140

Ala Gln Ala Ala Asn Ala His Leu Met Ala Gln Ile Gly Arg Lys
145                 150                 155                 160

Lys

<210> SEQ ID NO 2
<211> LENGTH: 8
<212> TYPE: PRT
<213> ORGANISM: Homo sapiens

<400> SEQUENCE: 2

Met Leu Met Pro Val His Phe Leu
1               5

<210> SEQ ID NO 3
<211> LENGTH: 9
<212> TYPE: PRT
<213> ORGANISM: Homo sapiens

<400> SEQUENCE: 3

Met Leu Met Pro Val His Phe Leu Leu
1               5

<210> SEQ ID NO 4
<211> LENGTH: 10
<212> TYPE: PRT
<213> ORGANISM: Homo sapiens

<400> SEQUENCE: 4

Met Leu Met Pro Val His Phe Leu Leu Leu
1               5                   10

<210> SEQ ID NO 5
<211> LENGTH: 11
<212> TYPE: PRT
<213> ORGANISM: Homo sapiens

<400> SEQUENCE: 5

Met Leu Met Pro Val His Phe Leu Leu Leu Leu
1               5                   10

<210> SEQ ID NO 6
<211> LENGTH: 9
<212> TYPE: PRT
<213> ORGANISM: Homo sapiens

<400> SEQUENCE: 6

Phe Leu Leu Leu Leu Leu Leu Leu Leu
1               5

<210> SEQ ID NO 7
<211> LENGTH: 8
<212> TYPE: PRT
<213> ORGANISM: Homo sapiens

<400> SEQUENCE: 7

Leu Met Pro Val His Phe Leu Leu
1               5

<210> SEQ ID NO 8
<211> LENGTH: 9
<212> TYPE: PRT
<213> ORGANISM: Homo sapiens

<400> SEQUENCE: 8

Leu Met Pro Val His Phe Leu Leu Leu
1               5

<210> SEQ ID NO 9
<211> LENGTH: 10
<212> TYPE: PRT
<213> ORGANISM: Homo sapiens

<400> SEQUENCE: 9

Leu Met Pro Val His Phe Leu Leu Leu Leu
1               5                   10

<210> SEQ ID NO 10
<211> LENGTH: 10
<212> TYPE: PRT
<213> ORGANISM: Homo sapiens

<400> SEQUENCE: 10

His Phe Leu Leu Leu Leu Leu Leu Leu Leu
1               5                   10

<210> SEQ ID NO 11
<211> LENGTH: 8
<212> TYPE: PRT
<213> ORGANISM: Homo sapiens

<400> SEQUENCE: 11

Phe Leu Leu Leu Leu Leu Leu Leu
1               5

<210> SEQ ID NO 12
<211> LENGTH: 10
<212> TYPE: PRT
<213> ORGANISM: Homo sapiens

<400> SEQUENCE: 12

Phe Leu Leu Leu Leu Leu Leu Leu Leu Gly
1               5                   10

<210> SEQ ID NO 13
<211> LENGTH: 10
<212> TYPE: PRT
<213> ORGANISM: Homo sapiens

<400> SEQUENCE: 13

Leu Leu Leu Gly Gly Pro Arg Thr Gly Leu
1               5                   10

<210> SEQ ID NO 14
<211> LENGTH: 11
<212> TYPE: PRT
<213> ORGANISM: Homo sapiens

<400> SEQUENCE: 14

Pro Arg Thr Gly Leu Pro His Lys Phe Tyr Lys
1               5                   10

<210> SEQ ID NO 15
<211> LENGTH: 10
<212> TYPE: PRT
<213> ORGANISM: Homo sapiens

<400> SEQUENCE: 15

Arg Thr Gly Leu Pro His Lys Phe Tyr Lys
1               5                   10

<210> SEQ ID NO 16
<211> LENGTH: 10
<212> TYPE: PRT
<213> ORGANISM: Homo sapiens

<400> SEQUENCE: 16

Gly Leu Pro His Lys Phe Tyr Lys Ala Lys
1               5                   10

<210> SEQ ID NO 17
<211> LENGTH: 8
<212> TYPE: PRT
<213> ORGANISM: Homo sapiens

<400> SEQUENCE: 17

Met Leu Met Pro Val His Phe Leu
1               5

<210> SEQ ID NO 18
<211> LENGTH: 9
<212> TYPE: PRT
<213> ORGANISM: Homo sapiens

<400> SEQUENCE: 18

Met Leu Met Pro Val His Phe Leu Leu
1               5

<210> SEQ ID NO 19
<211> LENGTH: 10
<212> TYPE: PRT
<213> ORGANISM: Homo sapiens

<400> SEQUENCE: 19

Met Leu Met Pro Val His Phe Leu Leu Leu
1               5                   10

<210> SEQ ID NO 20
<211> LENGTH: 8
<212> TYPE: PRT
<213> ORGANISM: Homo sapiens

<400> SEQUENCE: 20

Met Pro Val His Phe Leu Leu Leu
1               5

<210> SEQ ID NO 21
<211> LENGTH: 15
<212> TYPE: PRT
<213> ORGANISM: Homo sapiens

<400> SEQUENCE: 21

Phe Leu Leu Leu Leu Leu Leu Leu Leu Gly Gly Pro Arg Thr Gly
1               5                   10                  15

```
<210> SEQ ID NO 22
<211> LENGTH: 15
<212> TYPE: PRT
<213> ORGANISM: Homo sapiens

<400> SEQUENCE: 22

Leu Leu Leu Leu Leu Leu Leu Gly Gly Pro Arg Thr Gly Leu Leu
1               5                   10                  15

<210> SEQ ID NO 23
<211> LENGTH: 15
<212> TYPE: PRT
<213> ORGANISM: Homo sapiens

<400> SEQUENCE: 23

Leu Leu Leu Leu Leu Leu Gly Gly Pro Arg Thr Gly Leu Leu Pro
1               5                   10                  15

<210> SEQ ID NO 24
<211> LENGTH: 15
<212> TYPE: PRT
<213> ORGANISM: Homo sapiens

<400> SEQUENCE: 24

Leu Leu Leu Leu Leu Gly Gly Pro Arg Thr Gly Leu Pro His
1               5                   10                  15

<210> SEQ ID NO 25
<211> LENGTH: 15
<212> TYPE: PRT
<213> ORGANISM: Homo sapiens

<400> SEQUENCE: 25

Gly Leu Pro His Lys Phe Tyr Lys Ala Lys Pro Ile Phe Ser Cys
1               5                   10                  15

<210> SEQ ID NO 26
<211> LENGTH: 15
<212> TYPE: PRT
<213> ORGANISM: Homo sapiens

<400> SEQUENCE: 26

Leu Pro His Lys Phe Tyr Lys Ala Lys Pro Ile Phe Ser Cys Leu
1               5                   10                  15

<210> SEQ ID NO 27
<211> LENGTH: 15
<212> TYPE: PRT
<213> ORGANISM: Homo sapiens

<400> SEQUENCE: 27

Gly Leu Pro His Lys Phe Tyr Lys Ala Lys Pro Ile Phe Ser Cys
1               5                   10                  15

<210> SEQ ID NO 28
<211> LENGTH: 15
<212> TYPE: PRT
<213> ORGANISM: Homo sapiens

<400> SEQUENCE: 28

Leu Pro His Lys Phe Tyr Lys Ala Lys Pro Ile Phe Ser Cys Leu
1               5                   10                  15

<210> SEQ ID NO 29
<211> LENGTH: 10
```

```
<212> TYPE: PRT
<213> ORGANISM: Homo sapiens

<400> SEQUENCE: 29

Pro Arg Thr Gly Leu Pro His Lys Phe Tyr
1               5                   10

<210> SEQ ID NO 30
<211> LENGTH: 9
<212> TYPE: PRT
<213> ORGANISM: Homo sapiens

<400> SEQUENCE: 30

Gly Gln Trp Glu Asp Ala Ser Leu Leu
1               5

<210> SEQ ID NO 31
<211> LENGTH: 11
<212> TYPE: PRT
<213> ORGANISM: Homo sapiens

<400> SEQUENCE: 31

Ser Leu Leu Ser Lys Arg Ser Phe His Tyr Leu
1               5                   10

<210> SEQ ID NO 32
<211> LENGTH: 10
<212> TYPE: PRT
<213> ORGANISM: Homo sapiens

<400> SEQUENCE: 32

Leu Leu Ser Lys Arg Ser Phe His Tyr Leu
1               5                   10

<210> SEQ ID NO 33
<211> LENGTH: 11
<212> TYPE: PRT
<213> ORGANISM: Homo sapiens

<400> SEQUENCE: 33

Gly Gln Trp Glu Asp Ala Ser Leu Leu Ser Lys
1               5                   10

<210> SEQ ID NO 34
<211> LENGTH: 10
<212> TYPE: PRT
<213> ORGANISM: Homo sapiens

<400> SEQUENCE: 34

Ser Leu Leu Ser Lys Arg Ser Phe His Tyr
1               5                   10

<210> SEQ ID NO 35
<211> LENGTH: 9
<212> TYPE: PRT
<213> ORGANISM: Homo sapiens

<400> SEQUENCE: 35

Leu Leu Ser Lys Arg Ser Phe His Tyr
1               5

<210> SEQ ID NO 36
<211> LENGTH: 9
<212> TYPE: PRT
<213> ORGANISM: Homo sapiens
```

```
<400> SEQUENCE: 36

Arg Ser Phe His Tyr Leu Arg Ser Arg
1               5

<210> SEQ ID NO 37
<211> LENGTH: 9
<212> TYPE: PRT
<213> ORGANISM: Homo sapiens

<400> SEQUENCE: 37

Lys Phe Tyr Lys Ala Lys Pro Ile Phe
1               5

<210> SEQ ID NO 38
<211> LENGTH: 10
<212> TYPE: PRT
<213> ORGANISM: Homo sapiens

<400> SEQUENCE: 38

Tyr Lys Ala Lys Pro Ile Phe Ser Cys Leu
1               5                   10

<210> SEQ ID NO 39
<211> LENGTH: 8
<212> TYPE: PRT
<213> ORGANISM: Homo sapiens

<400> SEQUENCE: 39

Ser Leu Leu Ser Lys Arg Ser Phe
1               5

<210> SEQ ID NO 40
<211> LENGTH: 10
<212> TYPE: PRT
<213> ORGANISM: Homo sapiens

<400> SEQUENCE: 40

Leu Leu Ser Lys Arg Ser Phe His Tyr Leu
1               5                   10

<210> SEQ ID NO 41
<211> LENGTH: 9
<212> TYPE: PRT
<213> ORGANISM: Homo sapiens

<400> SEQUENCE: 41

Tyr Leu Arg Ser Arg Asp Ala Ser Ser
1               5

<210> SEQ ID NO 42
<211> LENGTH: 15
<212> TYPE: PRT
<213> ORGANISM: Homo sapiens

<400> SEQUENCE: 42

Pro His Lys Phe Tyr Lys Ala Lys Pro Ile Phe Ser Cys Leu Asn
1               5                   10                  15

<210> SEQ ID NO 43
<211> LENGTH: 15
<212> TYPE: PRT
<213> ORGANISM: Homo sapiens

<400> SEQUENCE: 43
```

His Lys Phe Tyr Lys Ala Lys Pro Ile Phe Ser Cys Leu Asn Thr
1               5                   10                  15

<210> SEQ ID NO 44
<211> LENGTH: 15
<212> TYPE: PRT
<213> ORGANISM: Homo sapiens

<400> SEQUENCE: 44

Lys Phe Tyr Lys Ala Lys Pro Ile Phe Ser Cys Leu Asn Thr Ala
1               5                   10                  15

<210> SEQ ID NO 45
<211> LENGTH: 15
<212> TYPE: PRT
<213> ORGANISM: Homo sapiens

<400> SEQUENCE: 45

Leu Ser Lys Arg Ser Phe His Tyr Leu Arg Ser Arg Asp Ala Ser
1               5                   10                  15

<210> SEQ ID NO 46
<211> LENGTH: 15
<212> TYPE: PRT
<213> ORGANISM: Homo sapiens

<400> SEQUENCE: 46

Ser Lys Arg Ser Phe His Tyr Leu Arg Ser Arg Asp Ala Ser Ser
1               5                   10                  15

<210> SEQ ID NO 47
<211> LENGTH: 15
<212> TYPE: PRT
<213> ORGANISM: Homo sapiens

<400> SEQUENCE: 47

Lys Arg Ser Phe His Tyr Leu Arg Ser Arg Asp Ala Ser Ser Gly
1               5                   10                  15

<210> SEQ ID NO 48
<211> LENGTH: 15
<212> TYPE: PRT
<213> ORGANISM: Homo sapiens

<400> SEQUENCE: 48

Arg Ser Phe His Tyr Leu Arg Ser Arg Asp Ala Ser Ser Gly Glu
1               5                   10                  15

<210> SEQ ID NO 49
<211> LENGTH: 15
<212> TYPE: PRT
<213> ORGANISM: Homo sapiens

<400> SEQUENCE: 49

Ser Phe His Tyr Leu Arg Ser Arg Asp Ala Ser Ser Gly Glu Glu
1               5                   10                  15

<210> SEQ ID NO 50
<211> LENGTH: 15
<212> TYPE: PRT
<213> ORGANISM: Homo sapiens

<400> SEQUENCE: 50

Glu Asp Ala Ser Leu Leu Ser Lys Arg Ser Phe His Tyr Leu Arg

-continued

```
1               5                   10                  15
```

<210> SEQ ID NO 51
<211> LENGTH: 15
<212> TYPE: PRT
<213> ORGANISM: Homo sapiens

<400> SEQUENCE: 51

```
Asp Ala Ser Leu Leu Ser Lys Arg Ser Phe His Tyr Leu Arg Ser
1               5                   10                  15
```

<210> SEQ ID NO 52
<211> LENGTH: 15
<212> TYPE: PRT
<213> ORGANISM: Homo sapiens

<400> SEQUENCE: 52

```
Ala Ser Leu Leu Ser Lys Arg Ser Phe His Tyr Leu Arg Ser Arg
1               5                   10                  15
```

<210> SEQ ID NO 53
<211> LENGTH: 15
<212> TYPE: PRT
<213> ORGANISM: Homo sapiens

<400> SEQUENCE: 53

```
Pro His Lys Phe Tyr Lys Ala Lys Pro Ile Phe Ser Cys Leu Asn
1               5                   10                  15
```

<210> SEQ ID NO 54
<211> LENGTH: 15
<212> TYPE: PRT
<213> ORGANISM: Homo sapiens

<400> SEQUENCE: 54

```
His Lys Phe Tyr Lys Ala Lys Pro Ile Phe Ser Cys Leu Asn Thr
1               5                   10                  15
```

<210> SEQ ID NO 55
<211> LENGTH: 15
<212> TYPE: PRT
<213> ORGANISM: Homo sapiens

<400> SEQUENCE: 55

```
Tyr Lys Ala Lys Pro Ile Phe Ser Cys Leu Asn Thr Ala Leu Ser
1               5                   10                  15
```

<210> SEQ ID NO 56
<211> LENGTH: 15
<212> TYPE: PRT
<213> ORGANISM: Homo sapiens

<400> SEQUENCE: 56

```
Lys Ala Lys Pro Ile Phe Ser Cys Leu Asn Thr Ala Leu Ser Glu
1               5                   10                  15
```

<210> SEQ ID NO 57
<211> LENGTH: 15
<212> TYPE: PRT
<213> ORGANISM: Homo sapiens

<400> SEQUENCE: 57

```
Ala Lys Pro Ile Phe Ser Cys Leu Asn Thr Ala Leu Ser Glu Ala
1               5                   10                  15
```

```
<210> SEQ ID NO 58
<211> LENGTH: 15
<212> TYPE: PRT
<213> ORGANISM: Homo sapiens

<400> SEQUENCE: 58

Lys Pro Ile Phe Ser Cys Leu Asn Thr Ala Leu Ser Glu Ala Glu
1               5                   10                  15

<210> SEQ ID NO 59
<211> LENGTH: 15
<212> TYPE: PRT
<213> ORGANISM: Homo sapiens

<400> SEQUENCE: 59

Pro Ile Phe Ser Cys Leu Asn Thr Ala Leu Ser Glu Ala Glu Lys
1               5                   10                  15

<210> SEQ ID NO 60
<211> LENGTH: 15
<212> TYPE: PRT
<213> ORGANISM: Homo sapiens

<400> SEQUENCE: 60

Leu Ser Lys Arg Ser Phe His Tyr Leu Arg Ser Arg Asp Ala Ser
1               5                   10                  15

<210> SEQ ID NO 61
<211> LENGTH: 15
<212> TYPE: PRT
<213> ORGANISM: Homo sapiens

<400> SEQUENCE: 61

Ser Lys Arg Ser Phe His Tyr Leu Arg Ser Arg Asp Ala Ser Ser
1               5                   10                  15

<210> SEQ ID NO 62
<211> LENGTH: 15
<212> TYPE: PRT
<213> ORGANISM: Homo sapiens

<400> SEQUENCE: 62

Lys Arg Ser Phe His Tyr Leu Arg Ser Arg Asp Ala Ser Ser Gly
1               5                   10                  15

<210> SEQ ID NO 63
<211> LENGTH: 15
<212> TYPE: PRT
<213> ORGANISM: Homo sapiens

<400> SEQUENCE: 63

Arg Ser Phe His Tyr Leu Arg Ser Arg Asp Ala Ser Ser Gly Glu
1               5                   10                  15

<210> SEQ ID NO 64
<211> LENGTH: 15
<212> TYPE: PRT
<213> ORGANISM: Homo sapiens

<400> SEQUENCE: 64

Ser Phe His Tyr Leu Arg Ser Arg Asp Ala Ser Ser Gly Glu Glu
1               5                   10                  15

<210> SEQ ID NO 65
```

```
<211> LENGTH: 10
<212> TYPE: PRT
<213> ORGANISM: Homo sapiens

<400> SEQUENCE: 65

Pro Arg Thr Gly Leu Pro His Lys Phe Tyr
1               5                   10

<210> SEQ ID NO 66
<211> LENGTH: 14
<212> TYPE: PRT
<213> ORGANISM: Homo sapiens

<400> SEQUENCE: 66

Leu Ser Glu Ala Glu Lys Gly Gln Trp Glu Asp Ala Ser Leu
1               5                   10

<210> SEQ ID NO 67
<211> LENGTH: 56
<212> TYPE: PRT
<213> ORGANISM: Homo sapiens

<400> SEQUENCE: 67

Ser Arg Asp Ala Ser Ser Gly Glu Glu Glu Gly Lys Glu Lys Lys
1               5                   10                  15

Thr Phe Pro Ile Ser Gly Ala Arg Gly Gly Ala Arg Gly Thr Arg Tyr
                20                  25                  30

Arg Tyr Val Ser Gln Ala Gln Pro Arg Gly Lys Pro Arg Gln Asp Thr
                35                  40                  45

Ala Lys Ser Pro His Arg Thr Lys
            50                  55

<210> SEQ ID NO 68
<211> LENGTH: 10
<212> TYPE: PRT
<213> ORGANISM: Homo sapiens

<400> SEQUENCE: 68

Thr Leu Ser Leu Asp Val Pro Thr Asn Ile
1               5                   10

<210> SEQ ID NO 69
<211> LENGTH: 10
<212> TYPE: PRT
<213> ORGANISM: Homo sapiens

<400> SEQUENCE: 69

Thr Asn Ile Met Asn Leu Leu Phe Asn Ile
1               5                   10

<210> SEQ ID NO 70
<211> LENGTH: 9
<212> TYPE: PRT
<213> ORGANISM: Homo sapiens

<400> SEQUENCE: 70

Asn Ile Met Asn Leu Leu Phe Asn Ile
1               5

<210> SEQ ID NO 71
<211> LENGTH: 8
<212> TYPE: PRT
<213> ORGANISM: Homo sapiens
```

```
<400> SEQUENCE: 71

Ile Met Asn Leu Leu Phe Asn Ile
1               5

<210> SEQ ID NO 72
<211> LENGTH: 10
<212> TYPE: PRT
<213> ORGANISM: Homo sapiens

<400> SEQUENCE: 72

Ile Met Asn Leu Leu Phe Asn Ile Ala Lys
1               5                   10

<210> SEQ ID NO 73
<211> LENGTH: 11
<212> TYPE: PRT
<213> ORGANISM: Homo sapiens

<400> SEQUENCE: 73

Met Asn Leu Leu Phe Asn Ile Ala Lys Ala Lys
1               5                   10

<210> SEQ ID NO 74
<211> LENGTH: 10
<212> TYPE: PRT
<213> ORGANISM: Homo sapiens

<400> SEQUENCE: 74

Asn Leu Leu Phe Asn Ile Ala Lys Ala Lys
1               5                   10

<210> SEQ ID NO 75
<211> LENGTH: 9
<212> TYPE: PRT
<213> ORGANISM: Homo sapiens

<400> SEQUENCE: 75

Leu Leu Phe Asn Ile Ala Lys Ala Lys
1               5

<210> SEQ ID NO 76
<211> LENGTH: 10
<212> TYPE: PRT
<213> ORGANISM: Homo sapiens

<400> SEQUENCE: 76

Ala His Leu Met Ala Gln Ile Gly Arg Lys
1               5                   10

<210> SEQ ID NO 77
<211> LENGTH: 9
<212> TYPE: PRT
<213> ORGANISM: Homo sapiens

<400> SEQUENCE: 77

His Leu Met Ala Gln Ile Gly Arg Lys
1               5

<210> SEQ ID NO 78
<211> LENGTH: 10
<212> TYPE: PRT
<213> ORGANISM: Homo sapiens

<400> SEQUENCE: 78
```

```
His Leu Met Ala Gln Ile Gly Arg Lys Lys
1               5                  10
```

<210> SEQ ID NO 79
<211> LENGTH: 9
<212> TYPE: PRT
<213> ORGANISM: Homo sapiens

<400> SEQUENCE: 79

```
Leu Met Ala Gln Ile Gly Arg Lys Lys
1               5
```

<210> SEQ ID NO 80
<211> LENGTH: 15
<212> TYPE: PRT
<213> ORGANISM: Homo sapiens

<400> SEQUENCE: 80

```
Ile Met Asn Leu Leu Phe Asn Ile Ala Lys Ala Lys Asn Leu Arg
1               5                  10                  15
```

<210> SEQ ID NO 81
<211> LENGTH: 15
<212> TYPE: PRT
<213> ORGANISM: Homo sapiens

<400> SEQUENCE: 81

```
Met Asn Leu Leu Phe Asn Ile Ala Lys Ala Lys Asn Leu Arg Ala
1               5                  10                  15
```

<210> SEQ ID NO 82
<211> LENGTH: 15
<212> TYPE: PRT
<213> ORGANISM: Homo sapiens

<400> SEQUENCE: 82

```
Asn Leu Leu Phe Asn Ile Ala Lys Ala Lys Asn Leu Arg Ala Gln
1               5                  10                  15
```

<210> SEQ ID NO 83
<211> LENGTH: 15
<212> TYPE: PRT
<213> ORGANISM: Homo sapiens

<400> SEQUENCE: 83

```
Leu Leu Phe Asn Ile Ala Lys Ala Lys Asn Leu Arg Ala Gln Ala
1               5                  10                  15
```

<210> SEQ ID NO 84
<211> LENGTH: 15
<212> TYPE: PRT
<213> ORGANISM: Homo sapiens

<400> SEQUENCE: 84

```
Leu Phe Asn Ile Ala Lys Ala Lys Asn Leu Arg Ala Gln Ala Ala
1               5                  10                  15
```

<210> SEQ ID NO 85
<211> LENGTH: 15
<212> TYPE: PRT
<213> ORGANISM: Homo sapiens

<400> SEQUENCE: 85

```
Ala Lys Ala Lys Asn Leu Arg Ala Gln Ala Ala Asn Ala His
1               5                  10                  15
```

```
<210> SEQ ID NO 86
<211> LENGTH: 15
<212> TYPE: PRT
<213> ORGANISM: Homo sapiens

<400> SEQUENCE: 86

Lys Ala Lys Asn Leu Arg Ala Gln Ala Ala Asn Ala His Leu
1               5                   10                  15

<210> SEQ ID NO 87
<211> LENGTH: 15
<212> TYPE: PRT
<213> ORGANISM: Homo sapiens

<400> SEQUENCE: 87

Ala Lys Asn Leu Arg Ala Gln Ala Ala Ala Asn Ala His Leu Met
1               5                   10                  15

<210> SEQ ID NO 88
<211> LENGTH: 15
<212> TYPE: PRT
<213> ORGANISM: Homo sapiens

<400> SEQUENCE: 88

Lys Asn Leu Arg Ala Gln Ala Ala Ala Asn Ala His Leu Met Ala
1               5                   10                  15

<210> SEQ ID NO 89
<211> LENGTH: 15
<212> TYPE: PRT
<213> ORGANISM: Homo sapiens

<400> SEQUENCE: 89

Phe Thr Leu Ser Leu Asp Val Pro Thr Asn Ile Met Asn Leu Leu
1               5                   10                  15

<210> SEQ ID NO 90
<211> LENGTH: 15
<212> TYPE: PRT
<213> ORGANISM: Homo sapiens

<400> SEQUENCE: 90

Thr Leu Ser Leu Asp Val Pro Thr Asn Ile Met Asn Leu Leu Phe
1               5                   10                  15

<210> SEQ ID NO 91
<211> LENGTH: 15
<212> TYPE: PRT
<213> ORGANISM: Homo sapiens

<400> SEQUENCE: 91

Ile Met Asn Leu Leu Phe Asn Ile Ala Lys Ala Lys Asn Leu Arg
1               5                   10                  15

<210> SEQ ID NO 92
<211> LENGTH: 15
<212> TYPE: PRT
<213> ORGANISM: Homo sapiens

<400> SEQUENCE: 92

Met Asn Leu Leu Phe Asn Ile Ala Lys Ala Lys Asn Leu Arg Ala
1               5                   10                  15
```

```
<210> SEQ ID NO 93
<211> LENGTH: 15
<212> TYPE: PRT
<213> ORGANISM: Homo sapiens

<400> SEQUENCE: 93

Asn Leu Leu Phe Asn Ile Ala Lys Ala Lys Asn Leu Arg Ala Gln
1               5                   10                  15

<210> SEQ ID NO 94
<211> LENGTH: 15
<212> TYPE: PRT
<213> ORGANISM: Homo sapiens

<400> SEQUENCE: 94

Leu Leu Phe Asn Ile Ala Lys Ala Lys Asn Leu Arg Ala Gln Ala
1               5                   10                  15

<210> SEQ ID NO 95
<211> LENGTH: 15
<212> TYPE: PRT
<213> ORGANISM: Homo sapiens

<400> SEQUENCE: 95

Leu Phe Asn Ile Ala Lys Ala Lys Asn Leu Arg Ala Gln Ala Ala
1               5                   10                  15

<210> SEQ ID NO 96
<211> LENGTH: 15
<212> TYPE: PRT
<213> ORGANISM: Homo sapiens

<400> SEQUENCE: 96

Met Asn Leu Leu Phe Asn Ile Ala Lys Ala Lys Asn Leu Arg Ala
1               5                   10                  15

<210> SEQ ID NO 97
<211> LENGTH: 15
<212> TYPE: PRT
<213> ORGANISM: Homo sapiens

<400> SEQUENCE: 97

Asn Leu Leu Phe Asn Ile Ala Lys Ala Lys Asn Leu Arg Ala Gln
1               5                   10                  15

<210> SEQ ID NO 98
<211> LENGTH: 15
<212> TYPE: PRT
<213> ORGANISM: Homo sapiens

<400> SEQUENCE: 98

Leu Leu Phe Asn Ile Ala Lys Ala Lys Asn Leu Arg Ala Gln Ala
1               5                   10                  15

<210> SEQ ID NO 99
<211> LENGTH: 15
<212> TYPE: PRT
<213> ORGANISM: Homo sapiens

<400> SEQUENCE: 99

Leu Phe Asn Ile Ala Lys Ala Lys Asn Leu Arg Ala Gln Ala Ala
1               5                   10                  15

<210> SEQ ID NO 100
<211> LENGTH: 15
```

```
<212> TYPE: PRT
<213> ORGANISM: Homo sapiens

<400> SEQUENCE: 100

Lys Ala Lys Asn Leu Arg Ala Gln Ala Ala Ala Asn Ala His Leu
1               5                   10                  15

<210> SEQ ID NO 101
<211> LENGTH: 15
<212> TYPE: PRT
<213> ORGANISM: Homo sapiens

<400> SEQUENCE: 101

Ala Lys Asn Leu Arg Ala Gln Ala Ala Ala Asn Ala His Leu Met
1               5                   10                  15

<210> SEQ ID NO 102
<211> LENGTH: 15
<212> TYPE: PRT
<213> ORGANISM: Homo sapiens

<400> SEQUENCE: 102

Lys Asn Leu Arg Ala Gln Ala Ala Ala Asn Ala His Leu Met Ala
1               5                   10                  15

<210> SEQ ID NO 103
<211> LENGTH: 8
<212> TYPE: PRT
<213> ORGANISM: Homo sapiens

<400> SEQUENCE: 103

Asn Leu Arg Ala Gln Ala Ala Ala
1               5
```